(12) United States Patent
Boyse et al.

(10) Patent No.: US 6,569,427 B1
(45) Date of Patent: *May 27, 2003

(54) ISOLATION AND PRESERVATION OF FETAL AND NEONATAL HEMATOPOIETIC STEM AND PROGENITOR CELLS OF THE BLOOD

(75) Inventors: Edward A. Boyse, Tucson, AZ (US); Hal E. Broxmeyer, Indianapolis, IN (US); Gordon W. Douglas, New York, NY (US)

(73) Assignee: PharmaStem Therapeutics, Inc., Del Mar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/442,277

(22) Filed: May 16, 1995

Related U.S. Application Data

(63) Continuation of application No. 07/950,356, filed on Sep. 24, 1992, now abandoned, which is a continuation of application No. 07/269,926, filed on Nov. 10, 1988, now Pat. No. 5,192,553, which is a continuation-in-part of application No. 07/119,746, filed on Nov. 12, 1987, now Pat. No. 5,004,681.

(51) Int. Cl.$^7$ ................................................. C12N 5/00
(52) U.S. Cl. ..................... 424/93.7; 424/529; 424/530; 424/531; 435/240.2
(58) Field of Search .............................. 424/529, 530, 424/531, 93.21; 435/240.2

(56) References Cited

U.S. PATENT DOCUMENTS

| | | | |
|---|---|---|---|
| 3,177,117 A | 4/1965 | Saunders et al. ............ | 424/529 |
| 3,344,617 A | 10/1967 | Rinfret et al. ................. | 62/322 |
| 3,753,357 A | 8/1973 | Schwartz .................... | 435/1.3 |
| 3,758,382 A | 9/1973 | Knorpp ......................... | 435/2 |
| 4,004,975 A | 1/1977 | Lionetti et al. ................ | 435/2 |
| 4,059,967 A | 11/1977 | Rowe et al. ................... | 62/64 |
| 4,199,022 A | 4/1980 | Senkan et al. ................. | 435/2 |
| 4,224,404 A | 9/1980 | Viza et al. ...................... | 435/2 |
| 4,396,601 A | 8/1983 | Salser et al. ............... | 424/94.5 |
| 4,714,680 A | 12/1987 | Civin .......................... | 435/347 |
| 4,721,096 A | 1/1988 | Naughton et al. .......... | 128/898 |
| 4,812,310 A | 3/1989 | Sato et al. ................... | 424/529 |
| 4,980,277 A | 12/1990 | Junnilla ......................... | 435/2 |
| 5,004,681 A | 4/1991 | Boyse et al. .................... | 435/2 |
| 5,192,553 A | 3/1993 | Boyse et al. ................. | 424/529 |

FOREIGN PATENT DOCUMENTS

| | | |
|---|---|---|
| DE | 29 29 278 A1 | 1/1981 |
| EP | 0 241 578 | 10/1987 |
| WO | WO 89/04168 | 5/1989 |

OTHER PUBLICATIONS

Barr et al., 1975, Hemopoietic stem cells in human peripheral blood. Science 190(4211):284–285.

Douay et al.,1986, Recovery of CFU–GM from cryopreserved marrow and in vivo evaluation after autologous bone marrow transplantation are predictive of engraftment. Exp Hematol. 14(5):358–365.

Fliedner, 1978, Advances in hematopoietic stem cell research: Their significance for clinical hematology. In: Proc. of the XIIth Congress of the Internat. Society of Hematology, pp. 63–68.

Exner et al., 1999, Clinical Applications of Mixed Chimerism. Ann. N. Y. Acad. Sci. 872–377–386.

Soper et al., 2001, Nonablative neonatal marrow transplantation attenuates functional and physical defects of β–glucuronidase deficiency. Blood 97:1498–1504.

Brecher et al., 1982, Special proliferative sites are not needed for seeding and proliferation of transfused bone marrow cells in normal syngeneic mice. Proc. Natl. Acad. Sci. USA 79:5085–5087.

McCarthy et al.,1985, Characterization of host lymphoid cells in antibody–facilitated bone marrow chimeras. Transplantation 40:12–17.

Wood et al., 1971, Use of homozygous allogeneic bone marrow for induction of tolerance with antilymphocyte serum: Does and Timing. Transplantation Proceedings, 3(1):676–79.

Stiff et al., 1986, Autologous transplantation using peripheral blood stem cells. Exp. Hematology. International Society for Experimental Hematology 5$^{th}$ Annual Meeting, Buffalo, NY. Abstract #311.

U.S. patent application Ser. No. 07/525,428, Boyse et al., filed May 16, 1990.

U.S. patent application Ser. No. 08/443,221, Boyse et al., filed May 17, 1995.

"CellPro starts SCID gene therapy", *Biotech Bussiness News*, May 21, 1993.

"New ADA Gene Therapy Trial Begins in US", *SCRIP*, Jun. 15, 1993, p. 26.

Ballantyne, 1993, "A Cord Linking Life and Life", *The Times*, May 6, 1993.

(List continued on next page.)

*Primary Examiner*—Jean C. Witz
(74) *Attorney, Agent, or Firm*—Pennie & Edmonds LLP

(57) ABSTRACT

The present invention relates to hematopoietic stem and progenitor cells of neonatal or fetal blood that are cryopreserved, and the therapeutic uses of such stem and progenitor cells upon thawing. In particular, the present invention relates to the therapeutic use of fetal or neonatal stem cells for hematopoietic (or immune) reconstitution. Hematopoietic reconstitution with the cells of the invention can be valuable in the treatment or prevention of various diseases and disorders such as anemias, malignancies, autoimmune disorders, and various immune dysfunctions and deficiencies. In another embodiment, fetal or neonatal hematopoietic stem and progenitor cells which contain a heterologous gene sequence can be used for hematopoietic reconstitution in gene therapy. In a preferred embodiment of the invention, neonatal or fetal blood cells that have been cryopreserved and thawed can be used for autologous (self) reconstitution.

56 Claims, 5 Drawing Sheets

OTHER PUBLICATIONS

Figure 1:
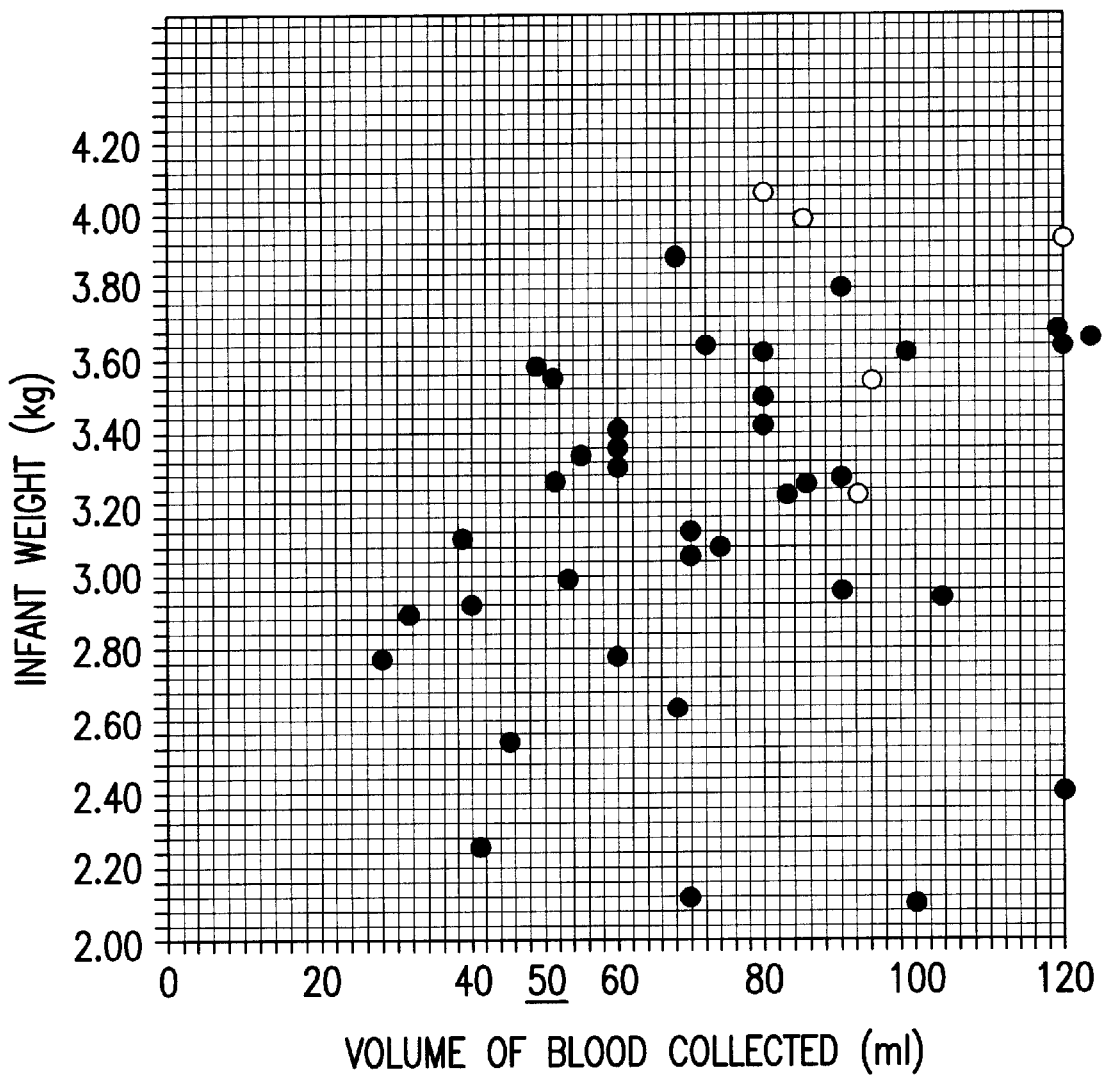

Broxmeyer et al., 1989, *Proc. Natl. Acad. Sci. USA 86:* 3828–3832.
Cain et al., 1986, *Transplantation 41(1):* 21–25.
Gluckman et al., 1985, *The Cancer Bulletin 37(5):* 238–242.
Gluckman et al., 1983, *Brit. J. Haematol. 54:* 431–440.
Hirokawa et al., 1982, *Clin. Immunol. Immunopathol. 22:* 297–304.
Lemischka et al., 1986, *Cell 45:* 917–927.
Mazur, 1970, *Science 168:* 939–949.
Moretti et al., 1985, in *Fetal Liver Transplantation,* Alan R. Liss, Inc., Prog. Clin. Biol. 193: 121–133.
Reiffers et al., 1986, *Exp. Hematol. 14:* 312–315.
Rowe and Fellig, 1962, *Fed. Proc. 21:* 157.
*The Lancet,* "Transplantation of Stem Cells from Fetal Liver", May 30, 1981, pp. 1193–1194.
Linner et al., 1986, *J. Histochem. Cytochem.* 34(9):1123–1135.
The HLB Newsletter, Jun. 23, 1994, 10(9), pp. 1, 73 and 74.
Jul. 6, 1995, N. Engl. J. Med. 333(1):67–69.
Abboud et al., 1992, Exp. Hematol. 20:1043–1047.
Andrews et al., 1986, Blood 68(5):1030–1035.
Andrews et al., 1990, J. Exp. Med. 172:355–358.
Apperley, 1994, Bone Marrow Transp. 14:187–196.
Bell et al., 1987, Br. J. Haematol. 67:252–253.
Boyum, 1968, Scand. J. Clin. Lab. Invest. 21(Suppl. 97):77–89.
Broxmeyer, 1983, CRC Critical Reviews in Oncology/Hematology 1(3):227–257.
Broxmeyer et al., 1994, abstract to be presented Aug., 1994 at The Meeting of Intl. Soc. Exp. Hematol.
Chang et al., 1989, Bone Marrow Transplantation 4:5–9.
Charbord et al., 1992, Bone Marrow Transplantation 9(Suppl. 1):109–110.
Clifford et al., 1961, The Lancet :687–690.
Coulombel et al., 1985, J. Clin. Invest. 75:961–969.
Falkenburg et al., 1993, Ann. Hematol. 67:231–236.
Gale, Feb. 9, 1995, N. Engl. J. Med. 332(6):392–394.
Gluckman et al., 1989, N. Engl. J. Med. 321(17):1174–1178.
Gordon et al., 1985, Leukemia Research 9:1017–1021.
Harris et al., 1994, Bone Marrow Transp. 13:135–143.
Issaragrisil, 1994, Blood Cells 20(2–3):259–262.
Jacobsen et al., 1979, Cell Tissue Kinet. 12:213–226.
Kaizer et al., 1985, Blood 65(6):1504–1510.
Kernan et al., 1994, Blood Cells 20(2–3):245–248.
King, 1961, J.A.M.A. 177(9):610–613.
Kurnick et al., 1958, Ann. Int. Med. 49(5):973–986.
Kurnick, 1962, Transfusion 2:178–187.
Kurtzberg et al., 1994, Blood Cells 20(2–3):275–283.
Lorenz et al., 1951, J. Natl. Cancer Inst. 12:197–201.
Löwenberg, 1975, Radiobiological Institute of the Organization for Health TNH, Rejswijk (Z.H.), The Netherlands, Table of Contents, and pp. 11–36 and 115–123.
McFarland et al., 1959, Blood 14(5):503–521.
McGann et al., 1981, Cryobiology 18:469–472.
McGovern et al., 1959, New Engl. J. Med. 260(14):675–683.
Migliaccio et al., 1992, Blood 79:2620–2627.
Nathan, 1989, N. Engl. J. Med. 321(17):1190–1191.
Newton et al., 1959, Br. Med. J. 1:531–535.
Pegg et al., 1962, Br. J. Cancer 16:417–435.
Richman et al., 1976, Blood 47(6):1031–1039.
Robertson et al., 1992, Blood 79(9):2229–2236.
Rowley et al., 1985, Exp. Hematol. 13:295–298.
Siena et al., 1985, Blood 65(3):655–662.
Socie et al., 1994, Blood 83(2):340–344.
Stephenson, Jun. 21, 1995, Journal of the American Medical Association 273(23):1813–1815.
Stone, 1992, Science 257:615.
Thierry et al., 1992, Bone Marrow Transplantation 9(Suppl. 1):101–104.
Thomas et al., 1957, N. Engl. J. Med. 257(11):491–496.
Thomas and Storb, 1970, Blood 36(4):507–515.
Thomas et al., 1977, Blood 49(4):511–533.
Thomas, Sep./Oct. 1995, Scientific American Science & Medicine, pp. 38–47.
Thompson, May 12, 1995, Science 268:805–806.
Valeri, 1976, in Blood anking and the use of frozen blood, CRC Press, Inc., pp. 1–7.
Van Brunt, 1993, BioWorld Today, Nov. 19, pp. 1–5.
Vowels et al., 1994, Blood Cells 20(2–3):249–255.
Wagner, 1994, Blood Cells 20(2–3):227–233.
Wagner et al., Jul. 23, 1995, The Lancet 346:214–219.
Yeager et al., 1986, N. Engl. J. Med. 315(3):141–147.
Besalduch, May 1985, Thesis, Naturaleza Y Characteristicas De Los Precusors Granulocitico–Macrofagicos En Sangre De Cordon, presented at the University of Valencia (in Spanish with English translation of pp. 100–101).
Butler, 1996, Nature News 382:99.
Fernandez–Delgado et al., 1986, An. Esp. Pediatr. 24:221–226.
Gabutti et al., 1975, Haematologica 60(4):60.
Harris Supplemental Declaration, Mar. 15, 1994.
Harris Declaration, Aug. 27, 1993.
Hows et al., 1981, The Lancet pp. 1193–1194.
Knight, 1980, Preservation of Leukocytes in Low Temperature Preservation in Medicine and Biology, Ch. 6, Ashwood–Smith and Farrant (University Park Press, Baltimore) pp. 121–137.
Koike, 1983, Acta. Paediatr. Japan 25:275–283.
Lemischka et al. Cell 1986 45:917–927.
Linner et al., 1986, J.Histochem. Cytochem. 34(9):1123–1135.
Papayannopoulou et al., 1986, Blood 67:99–104.
Radvany et al., Tissue Antigens 24:265–269.
Rubenstein, 1997, Declaration Under Article 117(1) In Support of the Opposition By Thermogenesis Corporation, with Exhibits A–F.
Smith and Broxmeyer, 1986, Br. J. Haematol. 63:29–34.
Wagner et al., 1987, Blood 82(10) Suppl. 1:Abstract 330.
Williams et al., 1986, Hum. Immunol. 17:302–310.
Wintrobe, 1980, Exposition and Glossary in *Blood, Pure and Eloquent,* Wintrobe, M. (ed.), McGraw–Hill Book Co., pp. 727–736.
42 Ashwood–smith, 1961, *Nature 190:* 1204–1205.
Alby, 1992, *Bone Marrow Transplantation 9(Suppl. 1):* 95–96.
Alink et al., 1976, *Cryobiology 13:* 295–304.
Auerbach et al., 1990, *Transfusion 30(8):* 682–687.
Ballantyne, 1993, "A Cord Linking Life and Life", *The Times,* May 6, 1993.
Bernstein et al., 1985, in *Genetic Engineering: Principles and Methods,* Setklow and Hollaender, eds., 7: 235–261.
Broxmeyer et al., 1990, *Int. J. Cell Cloning 8(Suppl. 1):*76–91.
Broxmeyer et al., 1992, *Bone Marrow Transplantation 9 (Suppl. 1):* 7–10.

Broxmeyer et al., 1989, *Proc. Natl. Acad. Sci. USA 86:* 3828–2832.
Broxmeyer et al., 1992, *Proc. Natl. Acad. Sci. USA 89:* 4109–4113.
Broxmeyer et al., 1991, *Blood Cells 17:* 313–329.
Cairo et al., 1992, *Pediatric Res. 32:* 277–281.
Castaigne et al., 1986, *Brit. J. Haematol.* 63(1):.
Champlin et al., 1983, *J. Cell. Biochem. Suppl. 7A:* 78 (abstract 0200).
Chang et al., 1986, *The Lancet* (Feb. 8, 1986): 294–295.
Cline, 1985, *Pharmac. Ther. 29:* 69–92.
Dick et al., 1986, in *Trends in Genetics: DNA Differentiation and Development,* Elsevier Publications, Stewart, ed., pp. 165–170.
Dick, 1987, in *Biological Approaches to the Controlled Delivery of Drugs,* New York Academy of Sciences, pp. 242–251.
Dick et al., 1985, *Cell 42:* 71–79.
Dicke et al., 1984, *Sem. Hematol. 21*(2): 109–122.
Eglitis et al., 1988, in *Molecular Biology of Hemopoiesis,* Plenum Press, New York, p. 19–27.
Eglitis et al., 1987, in *Molecular Approaches to Human Polygenic Disease,* Wiley, Chichester(Ciba Foundation Symposium 130), 229–246.
Ekhterae et al., 1988, *Blood 72*(5), Suppl. 1, 386a, Abstr. 1453.
Ekhterae et al., 1990, *Blood 75*(2): 365–369.
Ende, M., 1966, *Pac. Med. & Surg. 74:* 80–82.
Fabian et al., 1982, *Exp. Hematol. 10:* 119–122.
Fauser and Messner, 1978, *Blood 52*(6): 1243–1248.
Fliedner and Calvo, 1979, *Proceedings of the First International Symposium on Fetal Liver Transplantation,* Pesaro, Italy, Sep., 1979, pp. 305–309.
Gluckman et al., 1992, *Bone Marrow Transplantation 9 (suppl. 1):* 114–117.
Gluckman et al., 1980, *Brit. J. Haematol. 45:* 557–564.
Gluckman et al., 1990, *Bone Marrow Transplant 5 (Suppl. 2):* 42.
Gluckman et al., 1984, *Sem. Haematol. 21*(1): 20–26.
Goldman et al., 1980, *Brit. J. Haematol. 45:* 223–231.
Good et al., 1983, *Cellular Immunol. 82:* 36–54.
Gorin, 1986, *Clinics in Haematology 15*(1): 19–48.
Gruber et al., 1985, *Science 230:* 1057–1061.
Hassan et al., 1979, *British J. Haematol. 41:* 477–484.
Hermonat and Muzyczka, 1984, *Proc. Natl. Acad. Sci. USA 81:* 6466–6470.
Hershko et al., 1979, *The Lancet 1:* 945–947.
Herzig, 1983, in *Bone Marrow Transplantation,* Weiner et al., eds., The Committee on Technical Workshops, American Association of Blood Banks, Arlington, Virginia.
Hock and Miller, 1986, *Nature 320:* 275–277.
Hogge and Humphries, 1987, *Blood 69:* 611–617.
Hows et al., 1992, *The Lancet 340:* 73–76.
Hull, 1983, in *American Type Culture Collection,* Quartery Newsletter 3(4): 1.
Jaroff, 1993, "Brave New Babies: In Three Experiments Involving Gene Therapy, Doctors try to Cure a Hereditary Disease", *Time Magazine,* May 31, 1993.
Juttner et al., 1986, *Exp. Hematol. 14*(6): 465.
Juttner et al., 1985, *Brit. J. Haematol. 61:* 739–745.
Karp et al., 1985, *Biological Abstracts 80*(2): AB–624.
Karson et al., 1987, *Arch. AIDS Res. 1*(2–3): 148.
Karson et al., 1992, *J. Reprod. Med. 37*(6): 508–514.
Keller et al., 1985, *Nature 318:* 149–154.

Kemp et al., 1978, *Transplantation 26*(4): 260–264.
Knudtzon, 1974, *Blood 43*(3): 357–361.
Kohli–Kumar et al., 1993, *Brit. J. Haematol. 85:* 419–422.
Kohn et al., 1987, *Blood Cells 13:* 285–298.
Koizumi et al., 1982, *Blood 60*(4): 1046–1049.
Korbling et al., 1986, *Blood 67*(2): 529–532.
Lewis et al., 1967, *Transfusion 7*(1): 17–32.
Linch et al., 1982, *Blood 59*(5): 976–979.
Linch and Brent, 1989, *Nature 340:* 676.
Lovelock and Bishop, 1969, *Nature 183:* 1394–1395.
Lowenburg, 1975, *Uitgeverij Waltman–Delft,* Section 1.3.6, pp. 25–28, 36.
Lu et al., 1993, *Blood 81:* 41–48.
Mazur, 1977, *Cryobiology 14:* 251–272.
McGlave, 1991, *Blood Cells 17:* 330–337.
McGlave, 1985, in *Recent Advances in Hematology,* Hoffbrand, A.V., ed., Churchill Livingstone, London, pp. 171–197.
Miller et al., 1984, *Science 255:* 630.
Moritz et al., 1993, *J. Exp. Med. 178:* 529–536.
Nakahata and Ogawa, 1982, *J. Clin. Invest. 70:* 1324–1328.
Newton et al., 1993, *Exp. Hematol. 21:* 671–674.
Nothdurft et al., 1977, *Scand. J. Haematol. 19:* 470–481.
O'Reilly et al., 1984, *Sem. Hematol. 21*(3): 188–221.
O'Reilly et al., 1985, in *Fetal Liver Transplantation,* Gale R.P. et al., (eds.), Alan R. Liss, Inc., NY, pp. 327–342.
Ochs et al., 1981, *Pediatr. Res. 15 (4 part 2):* 601.
Paige et al., 1981, *J Exp. Med. 153:* 154–165.
Pollack et al., 1991, *Hum. Immunol. 30*(1):45–49.
Prindull et al., 1978, *Acta Paediatr. Scand. 67:* 413–416.
Prummer et al., 1985, *Exp. Hematol. 13:* 891–898.
Raghavachar et al., 1983, *J. Cell. Biochem. Suppl. 7A:* 78 (abstract 0198).
Rapatz et al., 1968, *Cryobiology 5*(1): 18–25.
Robinson and Simpson, 1971, *In Vitro 6*(5): 378.
Rowe and Lenny, 1983, *Cryobiology 20:* 717 (abstract 70).
Rowe, 1966, *Cryobiology 3*(1): 12–18.
Rowe and Rinfret, 1962, *Blood 20:* 636–637.
Rubinstein et al., 1993, *Blood 81:* 1679–1690.
Salser et al., 1981, in *Organization and Expression of Globin Genes,* Alan R. Liss, Inc., New York, pp. 313–334.
Sarpel et al., 1979, *Exp. Hemat. 7*(2): 113–120.
Schaison, 1992, *Bone Marrow Transplantation 9*(Suppl. 1): 93–94.
Shope et al., 1978, *Proc. Soc. Exp. Biol. and Med. 157:* 326–329.
Smith and Broxmeyer, 1986, *Br. J. Hematol. 63:* 29–34.
Spalding, 1987, *Chemical Week* (Jul. 29): 27.
Spitzer et al., 1984, *Cancer 54* (Sep. 15 suppl.): 1216–1225.
Srivasta et al., 1992, *Virology 189:* 456–461.
Stiff et al., 1983, *Cryobiology 20:* 17–24.
Storb and Thomas, 1983, *Immunol. Rev. 71:* 77–102.
Tchernia et al., 1981, *J. Lab. Clin. Med. 97*(3): 322–331.
Thomas et al., 1972, *The Lancet* (Feb. 5): 284–289.
Tilly et al., 1986, *The Lancet* (Jul. 19):154–155.
To and Juttner, 1987, *Brit. J. Haematol. 66:* 285–328.
Toneguzzo et al., *Proc. Natl. Acad. Sci. USA 83:* 3496–3499.
Touraine, 1983, *Birth Defects 19*(3): 139–142.
Touraine, 1980, *Excerpta Medica Intl. 514:* 276–283.
Tulany et al., 1975, *Proc. Natl. Acad. Sci. U.S.A. 72*(10): 4100–4104.
Ueno et al., 1981, *Exp. Hematol. 9:* 716–722.
Vainchecker et al., 1979, *Blood Cells 5:* 25–42.

Van Brunt, 1993, "Storage Banks Established for Cord Blood Stem Cells", *BioWorld Today,* Nov. 19, 1993.
Vickery et al., 1983, *J. Parasitol. 60(3):* 478–485.
Vilmer et al., 1992, *Transplantation 53(5):* 1155–1157.
Vowels et al., 1993, *New Engl. J. Med. 329:* 1623–1625.
Wagner et al., 1992, *Blood 79:* 1874–1881.
Wagner et al., 1993, *Blood 82(10) Suppl. 1:* Abstr. 330.
Wagner and Broxmeyer, 1992, *Blood 80:* 1624.
Williams et al., 1984, *Nature 310:* 476–480.
Zuckerman et al., 1968, *J. Clin. Pathol. (London) 21(1):* 109–110.
Livesy and Linner, 1987, *Nature 327:* 255–256.
Karp et al., 1985, *Am. J. Hemat. 18:*243–249.
Salhuddin et al., 1981, "Long–term suspension cultures of human cord–blood myeloid cells", *Blood 58(5)*:931–938.
Williams et al., 1987, "Characterization of Hematopoietic stem and progenitor cells," *Immunol. Res. 6:*294–307.
Gabutti et al., 1975, "Behaviour of human hematopoietic stem cells in cord and neonatal blood", Haematologica 60–60.
Knight, 1980, "Preservation of Leukocytes" in Low Temperature Preservation in Medecine and Biology, Ch. 6, Ashwood–Smith and Farrant (eds.), University Park Press, Baltimore, MD, pp. 121–137.

ISOLATION AND PRESERVATION OF FETAL AND NEONATAL HEMATOPOIETIC STEM AND PROGENITOR CELLS OF THE BLOOD

This application is a continuation of application Ser. No. 07/950,356, filed Sep. 24, 1992, now abandoned, which is a continuation of application Ser. No. 07/269,926 filed Nov. 10, 1988 now U.S. Pat. No. 5,192,553, which is a continuation-in-part of application Ser. No. 07/119,746, filed Nov. 12, 1987, now U.S. Pat. No. 5,804,601, each of which is incorporated by reference herein in its entirety.

TABLE OF CONTENTS

1. Introduction . . .
2. Background of the Invention . . .
    2.1. Hematopoietic Stem and Progenitor Cells . . .
    2.2. Reconstitution of the Hematopoietic System . . .
    2.3. Cryopreservation of Cells . . .
    2.4. Gene Therapy . . .
3. Summary of the Invention . . .
    3.1. Definitions . . .
4. Description of the Figures . . .
5. Detailed Description of the Invention . . .
    5.1. Isolation of Fetal or Neonatal Hematopoietic Stem and Progenitor Cells . . .
        5.1.1. Collection of Neonatal Blood . . .
            5.1.1.1. Volume . . .
            5.1.1.2. Preferred Aspects . . .
                5.1.1.2.1. Collection Kit . . .
                5.1.1.2.2. Vaginal Delivery of the Term Infant . . .
                5.1.1.2.3. Other Circumstances of Birth and Delivery . . .
                    5.1.1.2.3.1. Premature Birth . . .
                    5.1.1.2.3.2. Multiple Births . . .
                    5.1.1.2.3.3. Caesarian Delivery . . .
                    5.1.1.2.3.4. Complicated Delivery
                    5.1.1.2.3.5. Abnormal Placenta . . .
                    5.1.1.2.3.6. Collection from the Delivered Placenta . . .
                    5.1.1.2.3.7. Medical Conditions of the Mother . . .
                    5.1.1.2.3.8. Unplanned Delivery . . .
                5.1.1.2.4. Recordation of Data . . .
        5.1.2. Inspection and Testing of Neonatal Blood . . .
        5.1.3. Optional Procedures . . .
            5.1.3.1. Enrichment for Hematopoietic Stem and Progenitor Cells: Cell Separation Procedures . . .
            5.1.3.2. In Vitro Cultures of Hematopoietic Stem and Progenitor Cells . . .
    5.2. Cryopreservation . . .
    5.3. Recovering Stem and Progenitor Cells from the Frozen State . . .
        5.3.1. Thawing . . .
        5.3.2. Optional Procedures . . .
    5.4. Examination of Cells Recovered for Clinical Therapy . . .
        5.4.1. Identity Testing . . .
        5.4.2. Assays for Stem and Progenitor Cells . . .
    5.5. Hematopoietic Reconstitution . . .
    5.6. Therapeutic Uses . . .
        5.6.1. Diseases Resulting from a Failure or Dysfunction of Normal Blood Cell Production and Maturation . . .
        5.6.2. Hematopoietic Malignancies . . .
        5.6.3. Malignant Solid Tumors of Non-Hematopoietic Origin . . .
        5.6.4. Autoimmune Disorders . . .
        5.6.5. Gene Therapy . . .
        5.6.6. Miscellaneous Disorders Involving Immune Mechanisms . . .
    5.7 Generation and Use of Hematopoietic Stem and Progenitor Cell Progeny . . .
6. Examples . . .
    6.1. Collection of Human Umbilical Cord Blood and Placental Blood . . .
    6.2. Hematopoietic Stem and Progenitor Cells in Collected Cord Blood . . .
    6.3. Enrichment for Human Hematopoietic Stem and Progenitor Cells: Cell Separation Procedures . . .
        6.3.1. Density Separations . . .
        6.3.2. Adherence/Non-Adherence Separation.
    6.4. Cryopreservation of Cord Blood Stem and Progenitor Cells . . .
    6.5. Cell Thawing . . .
    6.6. Human Hematopoietic Stem and Progenitor Cell Assays . . .
        6.6.1. CFU-GM Assay . . .
            6.6.1.1. Preparation of McCoy's 5A Medium . . .
            6.6.1.2. Preparation of Human 5637 Urinary Bladder Carcinoma Cell Line Conditioned Medium . . .
            6.6.1.3. Preparation of Murine Pokeweed Mitogen Spleen Cell Conditioned Medium . . .
        6.6.2. BFU-E-2 and BFU-E-1/CFU-GEMM Assay . . .
            6.6.2.1. Preparation of 2.1
Methyl Cellulose . . .
            6.6.2.2. Preparation of Hemin . . .
            6.6.2.3. Preparation of Iscove's Modified Dulbecco's Medium . . . .
        6.6.3. Stem Cell Colony Forming Unit Assay . . .
        6.6.4. Assay of the Proliferative Status of Stem and Progenitor Cells . . .
    6.7. Recovery After Freeze-Thawing of Human Hematopoietic Progenitor Cells Derived from Cord Blood . . .
    6.8. Calculations of the Reconstituting Potential of Cord Blood . . .
    6.9. In Vitro Culture Conditions for Hematopoietic Stem and Progenitor Cells . . .
    6.10. Mouse Dissection Protocols . . . 6.10.1. Bone Marrow Dissection . . . 6.10.2. Spleen Dissection . . .
    6.11. Hematopoietic Reconstitution of Adult Mice with Syngeneic Fetal or Neonatal Stem Cells . . .
        6.11.1. Hematopoietic Reconstitution of Lethally-Irradiated Mice with Stem Cells in Blood of the Near-Term Fetus . . .
        6.11.2. Hematopoietic Reconstitution of Mice with a Lesser Volume of Near-Term Fetal Blood But Not with Adult Blood . . .
        6.11.3. Hematopoietic Reconstitution with Blood of Newborn Mice in Volumes as Low as Ten Microliters . . .
        6.11.4. Hematopoietic Reconstitution with Blood of Newborn Mice in Volumes of 10 or 15 Microliters . . .
    6.12 Hematopoietic Reconstitution For Treatment of Fanconi's Anemia . . .
    6.13. Flowchart: Description of a Service . . .

1. INTRODUCTION

The present invention is directed to hematopoietic stem and progenitor cells of neonatal or fetal blood, that are cryopreserved, and the therapeutic uses of such stem and progenitor cells upon thawing. Such cells can be therapeutically valuable for hematopoietic reconstitution in patients with various diseases and disorders. In a preferred embodiment, neonatal cells that have been cryopreserved and thawed, can be used for autologous (self) hematopoietic reconstitution.

The invention also relates to methods for collection and cryopreservation of the neonatal and fetal stem and progenitor cells of the invention.

2. BACKGROUND OF THE INVENTION

2.1. Hematopoietic Stem and Progenitor Cells

The morphologically recognizable and functionally capable cells circulating in blood include erythrocytes, neutrophilic, eosinophilic, and basophilic granulocytes, B-, T-, nonB-, non T-lymphocytes, and platelets. These mature cells derive from and are replaced, on demand, by morphologically recognizable dividing precursor cells for the respective lineages such as erythroblasts for the erythrocyte series, myeloblasts, promyelocytes and myelocytes for the granulocyte series, and megakaryocytes for the platelets. The precursor cells derive from more primitive cells that can simplistically be divided into two major subgroups: stem cells and progenitor cells (for review, see Broxmeyer, H. E., 1983, "colony Assays of Hematopoietic Progenitor Cells and Correlations to Clinical Situations," CRC Critical Reviews in Oncology/Hematology 1(3):227–257). The definitions of stem and progenitor cells are operational and depend on functional, rather than on morphological, criteria. Stem cells have extensive self-renewal or self-maintenance capacity (Lajtha, L. G., 1979, Differentiation 14:23), a necessity since absence or depletion of these cells could result in the complete depletion of one or more cell lineages, events that would lead within a short time to disease and death. Some of stem cells differentiate upon need, but some stem cells or their daughter cells produce other stem cells to maintain the precious pool of these cells. Thus, in addition to maintaining their own kind, pluripotential stem cells are capable of differentiation into several sublines of progenitor cells with more limited self-renewal capacity or no self-renewal capacity. These progenitor cells ultimately give rise to the morphologically recognizable precursor cells. The progenitor cells are capable of proliferating and differentiating along one, or more than one, of the myeloid differentiation pathways (Lajtha, L. G. (Rapporteur), 1979, Blood Cells 5:447).

Stem and progenitor cells make up a very small percentage of the nucleated cells in the bone marrow, spleen, and blood. About ten times fewer of these cells are present in the spleen relative to the bone marrow, with even less present in the adult blood. As an example, approximately one in one thousand nucleated bone marrow cells is a progenitor cell; stem cells occur at a lower frequency. These progenitor and stem cells have been detected and assayed for by placing dispersed suspensions of these cells into irradiated mice, and noting those cells that seeded to an organ such as the spleen and which found the environment conducive to proliferation and differentiation. These cells have also been quantified by immobilizing the cells outside of the body in culture plates (in vitro) in a semi-solid support medium such as agar, methylcellulose, or plasma clot in the presence of culture medium and certain defined biomolecules or cell populations which produce and release these molecules. Under the appropriate growth conditions, the stem or progenitor cells will go through a catenated sequence of proliferation and differentiation yielding mature end stage progeny, which thus allows the determination of the cell type giving rise to the colony. If the colony contains granulocytes, macrophages, erythrocytes, and megakaryocytes (the precursors to platelets, then the cell giving rise to them would have been a pluripotential cell. To determine if these cells have self-renewal capacities, or stemness, and can thus produce more of their own kind, cells from these colonies can be replated in vivo or in vitro. Those colonies, which upon replating into secondary culture plates, give rise to more colonies containing cells of multilineages, would have contained cells with some degree of stemness. The stem cell and progenitor cell compartments are themselves heterogeneous with varying degrees of self-renewal or proliferative capacities. A model of the stem cell compartment has been proposed based on the functional capacities of the cell (Hellman, S., et al., 1983, J. Clin. Oncol. 1:227–284). Self-renewal would appear to be greater in those stem cells with the shortest history of cell division, and this self-renewal would become progressively more limited with subsequent division of the cells.

A human hematopoietic colony-forming cell with the ability to generate progenitors for secondary colonies has been identified in human umbilical cord blood (Nakahata, T. and Ogawa, M., 1982, J. Clin. Invest. 70:1324–1328). In addition, hematopoietic stem cells have been demonstrated in human umbilical cord blood, by colony formation, to occur at a much higher level than that found in the adult (Prindull, G., et al., 1978, Acta Paediatr. Scand. 67:413–416; Knudtzon, S., 1974, Blood 43(3):357–361). The presence of circulating hematopoietic progenitor cells in human fetal blood (Linch, D. C., et al., 1982, Blood 59(5):976–979) and in cord blood (Fauser, A. A. and Messner, H. A., 1978, Blood 52(6):1243–1248) has also been shown. Human fetal and neonatal blood has been reported to contain megakaryocyte and burst erythroblast progenitors (Vainchenker, W., et al., 1979, Blood Cells 5:15–42), with increased numbers of erythroid progenitors in human cord blood or fetal liver relative to adult blood (Hassan, M. W., et al., 1979, Br. J. Haematol. 41:477–484; Tchernia, G., et al., 1981, J. Lab. Clin. Med. 97(3):322–331). Studies have suggested some differences between cord blood and bone marrow cells in the characteristics of CFU-GM (colony forming unit-granulocyte, macrophage) which express surface Ia antigens (Koizumi, S., et al., 1982, Blood 60(4):1046–1049).

U.S. Pat. No. 4,714,680 discloses cell suspensions comprising human stem and progenitor cells and methods for isolating such suspensions, and the use of the cell suspensions for hematopoietic reconstitution.

2.2. Reconstitution of the Hematopoietic System

Reconstitution of the hematopoietic system has been accomplished by bone marrow transplantation. Lorenz and coworkers showed that mice could be protected against lethal irradiation by intravenous infusion of bone marrow (Lorenz, E., et al., 1951, J. Natl. Cancer Inst. 12:197–201). Later research demonstrated that the protection resulted from colonization of recipient bone marrow by the infused cells (Lindsley, D. L., et al., 1955, Proc. Soc. Exp. Biol. Med. 90:512–515; Nowell, P. C., et al., 1956, Cancer Res. 16:258–261; Mitchison, N. A., 1956, Br. J. Exp. Pathol. 37:239–247; Thomas, E. D., et al., 1957, N. Engl. J. Med. 257:491–496). Thus, stem and progenitor cells in donated bone marrow can multiply and replace the blood cells responsible for protective immunity, tissue repair, clotting, and other functions of the blood. In a successful bone marrow transplantation, the blood, bone marrow, spleen, thymus and other organs of immunity are repopulated with cells derived from the donor.

U.S. Pat No. 4,721,096 by Naughton et al. discloses a method of hematopoietic reconstitution which comprises obtaining and cryopreserving bone marrow, replicating the bone marrow cells in vitro, and then infusing the cells into a patient.

Bone marrow has been used with increasing success to treat various fatal or crippling diseases, including certain types of anemias such as aplastic anemia (Thomas, E. D., et al., Feb. 5, 1972, The Lancet, pp. 284–289), Fanconi's anemia (Gluckman, E., et al., 1980, Brit. J. Haematol. 45:557–564; Gluckman, E., et al., 1983, Brit. J. Haematol. 54:431–440; Gluckman, E., et al., 1984, Seminars in Hematology:21(1):20–26), immune deficiencies (Good, R. A., et al., 1985, Cellular Immunol. 82:36–54), cancers such as lymphomas or leukemias (Cahn, J. Y., et al., 1986, Brit. J. Haematol. 63:457–470; Blume, K. J. and Forman, S. J., 1982, J. Cell. Physiol. Supp. 1:99–102; Cheever, M. A., et al., 1982, N. Engl. J. Med. 307(8):479–481), carcinomas (Blijham, G., et al., 1981, Eur. J. Cancer 17(4):433–441), various solid tumors (Ekert, H., et al., 1982, Cancer 49:603–609; Spitzer, G., et al., 1980, Cancer 45:3075–3085), and genetic disorders of hematopoiesis. Bone marrow transplantation has also recently been applied to the treatment of inherited storage diseases (Hobbs, J. R., 1981, Lancet 2:735–739), thalassemia major (Thomas, E. D., et al., 1982, Lancet 2:227–229), sickle cell disease (Johnson, F. J., et al., 1984, N. Engl. J. Med. 311:780–783), and osteopetrosis (Coccia, P. F., et al., 1980, N. Engl. J. Med. 302:701–708) (for general discussions, see Storb, R. and Thomas, E. D., 1983, Immunol. Rev. 71:77–102; O'Reilly, R., et al., 1984, Sem. Hematol. 21(3):188–221; 1969, Bone-Marrow Conservation, Culture and Transplantation, Proceedings of a Panel, Moscow, Jul. 22–26, 1968, International Atomic Energy Agency, Vienna; McGlave, P. B., et al., 1985, in Recent Advances in Haematology, Hoffbrand, A. V., ed., Churchill Livingstone, London, pp. 171–197).

Present use of bone marrow transplantation is severely restricted, since it is extremely rare to have perfectly matched (genetically identical) donors, except in cases where an identical twin is available or where bone marrow cells of a patient in remission are stored in a viable frozen state. Even in such an autologous system, the danger due to undetectable contamination with malignant cells, and the necessity of having a patient healthy enough to undergo marrow procurement, present serious limitations. (For reviews of autologous bone marrow transplantation, see Herzig, R. H., 1983, in Bone Marrow Transplantation, Weiner, R. S., et al., eds., The Committee On Technical Workshops, American Association of Blood Banks, Arlington, Va.; Dicke, K. A., et al., 1984, Sem. Hematol. 21(2):109–122; Spitzer, G., et al., 1984, Cancer 54 (September 15 Suppl.):1216–1225). Except in such autologous cases, there is an inevitable genetic mismatch of some degree, which entails serious and sometimes lethal complications. These complications are two-fold. First, the patient is usually immunologically incapacited by drugs beforehand, in order to avoid immune rejection of the foreign bone marrow cells (host versus graft reaction). Second, when and if the donated bone marrow cells become established, they can attack the patient (graft versus host disease), who is recognized as foreign. Even with closely matched family donors, these complications of partial mismatching are the cause of substantial mortality and morbidity directly due to bone marrow transplantation from a genetically different individual.

Peripheral blood has also been investigated as a source of stem cells for hematopoietic reconstitution (Nothdurtt, W., et al., 1977, Scand. J. Haematol. 19:470–481; Sarpel, S. C., et al., 1979, Exp. Hematol. 7:113–120; Ragharachar, A., et al., 1983, J. Cell. Biochem. Suppl. 7A:78; Juttner, C. A., et al., 1985, Brit. J. Haematol. 61:739–745; Abrams, R. A., et al., 1983, J. Cell. Biochem. Suppl. 7A:53; Prummer, O., et al., 1985, Exp. Hematol. 13:891–898). In some studies, promising results have been obtained for patients with various leukemias (Reiffers, J., et al., 1986, Exp. Hematol. 14:312–315 (using cryopreserved cells); Goldman, J. M., et al., 1980, Br. J. Haematol. 45:223–231; Ti ly, H., et al., Jul. 19, 1986, The Lancet, pp. 154–155; see also To, L. B. and Juttner, C. A., 1987, Brit. J. Haematol. 66: 285–288, and references cited therein); and with lymphoma (Korbling, M., et al., 1986, Blood 67:529–532). It has been implied that the ability of autologous peripheral adult blood to reconstitute the hematopoietic system, seen in some cancer patients, is associated with the far greater numbers of circulating progenitor cells in the peripheral blood produced after cytoreduction due to intensive chemotherapy and/or irradiation (the rebound phenomenon) (To, L. B. and Juttner, C. A., 1987, Annot., Brit. J. Haematol. 66:285–288; see also 1987, Brit. J. Haematol. 67:252–253, and references cited therein). Other studies using peripheral blood have failed to effect reconstitution (Hershko, C., et al., 1979, The Lancet 1:945–947; Ochs, H. D., et al., 1981, Pediatr. Res. 15(4 Part 2):601).

Studies have also investigated the use of fetal liver cell transplantation (Cain, G. R., et al., 1986, Transplantation 41(1):32–25; Ochs, H. D., et al., 1981, Pediatr. Res. 15(4 part 2):601; Paige, C. J., et al., 1981, J. Exp. Med. 153:154–165; Touraine, J. L., 1980, Excerpta Med. 514:277; Touraine, J. L., 1983, Birth Defects 19:139; see also Good, R. A., et al., 1983, Cellular Immunol. 82:44–45 and references cited therein) or neonatal spleen cell transplantation (Yunis, E. J., et al., 1974, Proc. Natl. Acad. Sci. U.S.A. 72:4100) as stem cell sources for hematopoietic reconstitution. Cells of neonatal thymus have also been transplanted in immune reconstitution experiments (Vickery, A. C., et al., 1983, J. Parasitol. 69(3):478–485; Hirokawa, K., et al., 1982, Clin. Immunol. Immunopathol. 22:297–304).

2.3. Cryopreservation of Cells

Freezing is destructive to most living cells. Upon cooling, as the external medium freezes, cells equilibrate by losing water, thus increasing intracellular, solute concentration. Below about 10–15° C., intracellular freezing will occur. Both intracellular freezing and solution effects are responsible for cell injury (Mazur, P., 1970, Science 168:939–949). It has been proposed that freezing destruction from extracellular ice is essentially a plasma membrane injury resulting from osmotic dehydration of the cell (Meryman, H. T., et al., 1977, Cryobiology 14:287–302).

Cryoprotective agents and optimal cooling rates can protect against cell injury. Cryoprotection by solute addition is thought to occur by two potential mechanisms: colligatively, by penetration into the cell, reducing the amount of ice formed; or kinetically, by decreasing the rate of water flow out of the cell in response to a decreased vapor pressure of external ice (Meryman, H. T., et al., 1977, Cryobiology 14:287–302). Different optimal cooling rates have been described for different cells. Various groups have looked at the effect of cooling velocity or cryopreservatives upon the survival or transplantation efficiency of frozen bone marrow cells or red blood cells (Lovelock, J. E. and Bishop, M. W. H., 1959, Nature 183:1394–1395; Ashwood-Smith, M. J., 1961, Nature 190:1204–1205; Rowe, A. W. and Rinfret, A. P., 1962, Blood 20:636; Rowe, A. W. and Fellig, J., 1962, Fed. Proc. 21:157; Rowe, A. W., 1966, Cryobiology 3(1):12–18; Lewis, J. P., et al., 1967, Transfusion 7(1):17–32; Rapatz, G., et al., 1968, Cryobiology 5(1):18–25; Mazur, P., 1970, Science 168:939–949; Mazur, P., 1977, Cryobiology 14:251–272; Rowe, A. W. and Lenny, L. L., 1983, Cryobiology 20:717; Stiff, P. J., et al., 1983, Cryobiology 20:17–24; Gorin, N. C., 1986, clinics in Haematology 15(1):19–48).

The successful recovery of human bone marrow cells after long-term storage in liquid nitrogen has been described (1983, American Type Culture Collection, Quarterly Newsletter 3(4):1). In addition, stem cells in bone marrow were shown capable of withstanding cryopreservation and thawing without significant cell death, as demonstrated by the ability to form equal numbers of mixed myeloid-erythroid colonies in vitro both before and after freezing (Fabian, I., et al., 1982, Exp. Hematol. 10(1):119–122). The cryopreservation and thawing of human fetal liver cells (Zuckerman, A. J., et al., 1968, J. Clin. Pathol. (London) 21(1):109–110), fetal myocardial cells (Robinson, D. M. and Simpson, J. F., 1971, In Vitro 6(5):378), neonatal rat heart cells (Alink, G. M., et al., 1976, Cryobiology 13:295–304), and fetal rat pancreases (Kemp, J. A., et al., 1978, Transplantation 26(4):260–264) have also been reported.

2.4. Gene Therapy

Gene therapy refers to the transfer and stable insertion of new genetic information into cells for the therapeutic treatment of diseases or disorders. The foreign gene is transferred into a cell that proliferates to spread the new gene throughout the cell population. Thus stem cells, or pluripotent progenitor cells, are usually the target of gene transfer, since they are proliferative cells that produce various progeny lineages which will potentially express the foreign gene.

Most studies in gene therapy have focused on the use of hematopoietic stem cells. High efficiency gene transfer systems for hematopoietic progenitor cell transformation have been investigated for use (Morrow, J. F., 1976, Ann. N.Y. Acad. Sci. 265:13; Salzar, W., et al., 1981, in Organization and Expression of Globin Genes, A. R. Liss, Inc., New York, p. 313; Bernstein, A., 1985, in Genetic Engineering: Principles and Methods, Plenum Press, New York, p. 235; Dick, J. E., et al., 1986, Trends in Genetics 2:165). Reports on the development of viral vector systems indicate a higher efficiency of transformation than DNA-mediated gene transfer procedures (e.g., $CaPO_4$ precipitation and DEAE dextran) and show the capability of integrating transferred genes stably in a wide variety of cell types. Recombinant retrovirus vectors have been widely used experimentally to transduce hematopoietic stem and progenitor cells. Genes that have been successfully expressed in mice after transfer by retrovirus vectors include human hypoxanthine phosphoribosyl transferase (Miller, A., et al., 1984, Science 255:630). Bacterial genes have also been transferred into mammalian cells, in the form of bacterial drug resistance gene transfers in experimental models. The transformation of hematopoietic progenitor cells to drug resistance by eukaryotic virus vectors, has been accomplished with recombinant retrovirus-based vector systems (Hock, R. A. and Miller, A. D., 1986, Nature 320:275–277; Joyner, A., et al., 1983, Nature 305:556–558; Williams, D. A., et al., 1984, Nature 310:476–480; Dick, J. E., et al., 1985, Cell 42:71–79); Keller, G., et al., 1985, Nature 318:149–154; Eglitis, M., et al., 1985, Science 230:1395–1398). Recently, adeno-associated virus vectors have been used successfully to transduce mammalian cell lines to neomycin resistance (Hermonat, P. L. and Muzyczka, N., 1984, supra; Tratschin, J.-D., et al., 1985, Mol. Cell. Biol. 5:3251). Other viral vector systems that have been investigated for use in gene transfer include papovaviruses and vaccinia viruses (see Cline, M. J., 1985, Pharmac. Ther. 29:69–92).

Other methods of gene transfer include microinjection, electroporation, liposomes, chromosome transfer, and transfection techniques (Cline, M. J., 1985, supra). Salser et al. used a calcium-precipitation transfection technique to transfer a methotrexate-resistant dihydrofolate reductase (DHFR) or the herpes simplex virus thymidine kinase gene, and a human globin gene into murine hematopoietic stem cells. In vivo expression of the DHFR and thymidine kinase genes in stem cell progeny was demonstrated (Salser, W., et al., 1981, in Organization and Expression of Globin Genes, Alan R. Liss, Inc., New York, pp. 313–334).

Gene therapy has also been investigated in murine models with the goal of enzyme replacement therapy. Thus, normal stem cells from a donor mouse have been used to reconstitute the hematopoietic cell system of mice lacking beta-glucuronidase (Yatziv, S., et al., 1982, J. Lab. Clin. Med. 90:792–797). Since a native gene was being supplied, no recombinant stem cells (or gene transfer techniques) were necessary.

3. SUMMARY OF THE INVENTION

The present invention is directed to hematopoietic stem and progenitor cells of neonatal or fetal blood, that are cryopreserved, and the therapeutic uses of such stem and progenitor cells upon thawing. In particular, the present invention relates to the therapeutic use of fetal or neonatal stem cells for hematopoietic (or immune) reconstitution. Hematopoietic reconstitution with the cells of the invention can be valuable in the treatment or prevention of various diseases and disorders such as anemias, malignancies, autoimmune disorders, and other immune dysfunctions and deficiencies. In another embodiment, fetal or neonatal hematopoietic stem and progenitor cells which contain a heterologous gene sequence can be used for hematopoietic reconstitution in gene therapy.

In a preferred embodiment of the invention, neonatal or fetal blood cells that have been cryopreserved and thawed can be used for autologous (self) reconstitution.

The invention also relates to methods of collection and cryopreservation of the neonatal and fetal stem and progenitor cells of the invention.

3.1. Definitions

As used herein, the following abbreviations will have the meanings indicated:

| | |
|---|---|
| ACD = | acid-citrate dextrose |
| BFU-E = | burst-forming unit-erythroid. An hematopoietic progenitor cell which is capable of producing a colony of erythroid progeny cells in semi-solid medium. |
| BFU-E-1 = | an early erythroid progenitor cell, capable of producing a colony of erythroid progeny cells in semi-solid medium upon stimulation by erythropoietin, hemin (optional), and a burst-promoting factor. |

-continued

| | |
|---|---|
| BFU-E-2 = | an erythroid progenitor cell, of greater maturity than BFU-E-1, which is capable of producing a colony of erythroid progeny cells in semi-solid medium upon stimulation by erythropoietin and by hemin (optional). |
| CFU = | colony-forming unit. A cell which is capable of producing a colony of progeny cells in semi-solid medium. |
| CFU-GEMM = | colony-forming unit-granulocyte, erythrocyte, monocyte/macrophage, megakaryocyte. A multipotential hematopoietic progenitor cell which is capable of producing a colony composed of granulocyte, erythrocyte, monocyte/macrophage, and megakaryocyte progeny, in semi-solid medium. |
| CFU-GM = | colony-forming unit-granulocyte, macrophage. An hematopoietic progenitor cell which is capable of producing a colony composed of granulocyte and macrophage progeny in semi-solid medium. |
| CFU-S = | colony forming unit-spleen. A multipotential stem cell with self-renewal capacity, which, upon inoculation into lethally-irradiated mice, is capable of producing a colony (nodule) on the spleen(s). |
| CPD = | citrate-phosphate-dextrose |
| CSF = | colony stimulating factor |
| DMSO = | dimethyl sulfoxide |
| DNase = | deoxyribonuclease |
| DPBS = | phosphate buffered saline without magnesium or calcium |
| FCS = | fetal calf serum |
| heterologous gene = | a gene which is not present, or not functionally expressed, in the designated host cell. |
| IMDM = | Iscove's Modified Dulbecco's Medium |
| LD100/30 days = | the minimum or near-minimal Lethal Dosage causing 100% mortality within a 30-day post-irradiation period |
| PHALCM = | medium conditioned by phytohemagglutinin-stimulated leukocytes from patients with hemochromatosis |
| PWMSCM = | pokeweed mitogen spleen cell conditioned medium |
| S-cell = | stem cell |
| SLE = | systemic lupus erythematosus |
| $^3$HTdr = | tritiated thymidine |
| TLI = | total lymphoid irradiation |

4. DESCRIPTION OF THE FIGURES

FIG. 1 presents data for neonatal blood volumes obtained in one series of collections from individual births. The volume (ml) of blood collected is shown along the X-axis, with infant weight (kg) along the Y-axis. Open circles represent births by Caesarian section; closed circles represent vaginal births.

Figure 2:
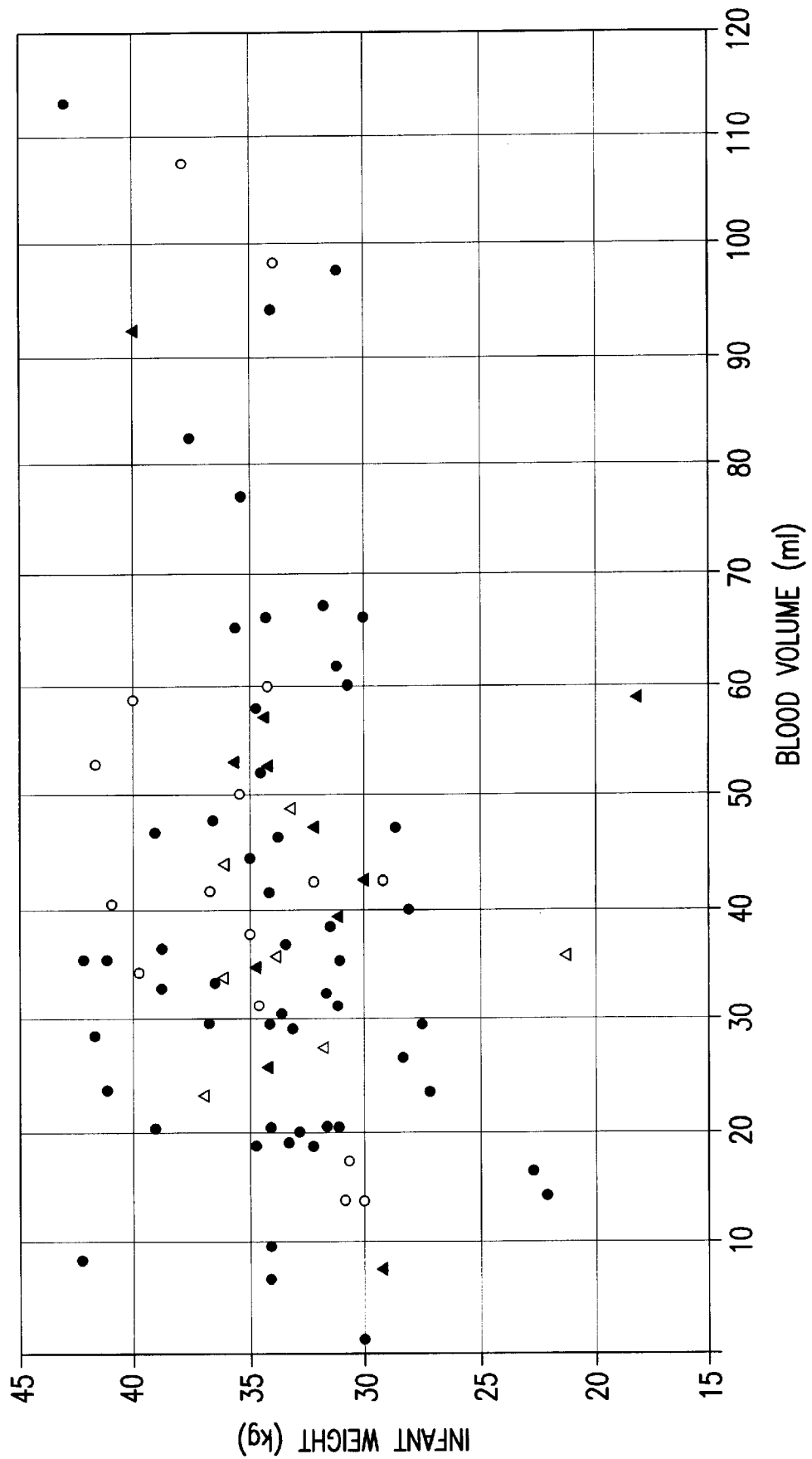

FIG. 2 presents the data from neonatal blood volumes obtained in a second series of collections from individual births. The volume (ml) of blood collected is shown along the X-axis, with the infant weight (kg) along the Y-axis. Closed circles represent vaginal births, with collection by gravity drainage from the umbilical cord. Open circles represent births by Caesarian section, with collection by gravity drainage from the umbilical cord. Closed triangles represent vaginal births, with collection from the delivered placenta. open triangles represent births by Caesarian section, with collection from the delivered placenta.

Figure 3A:
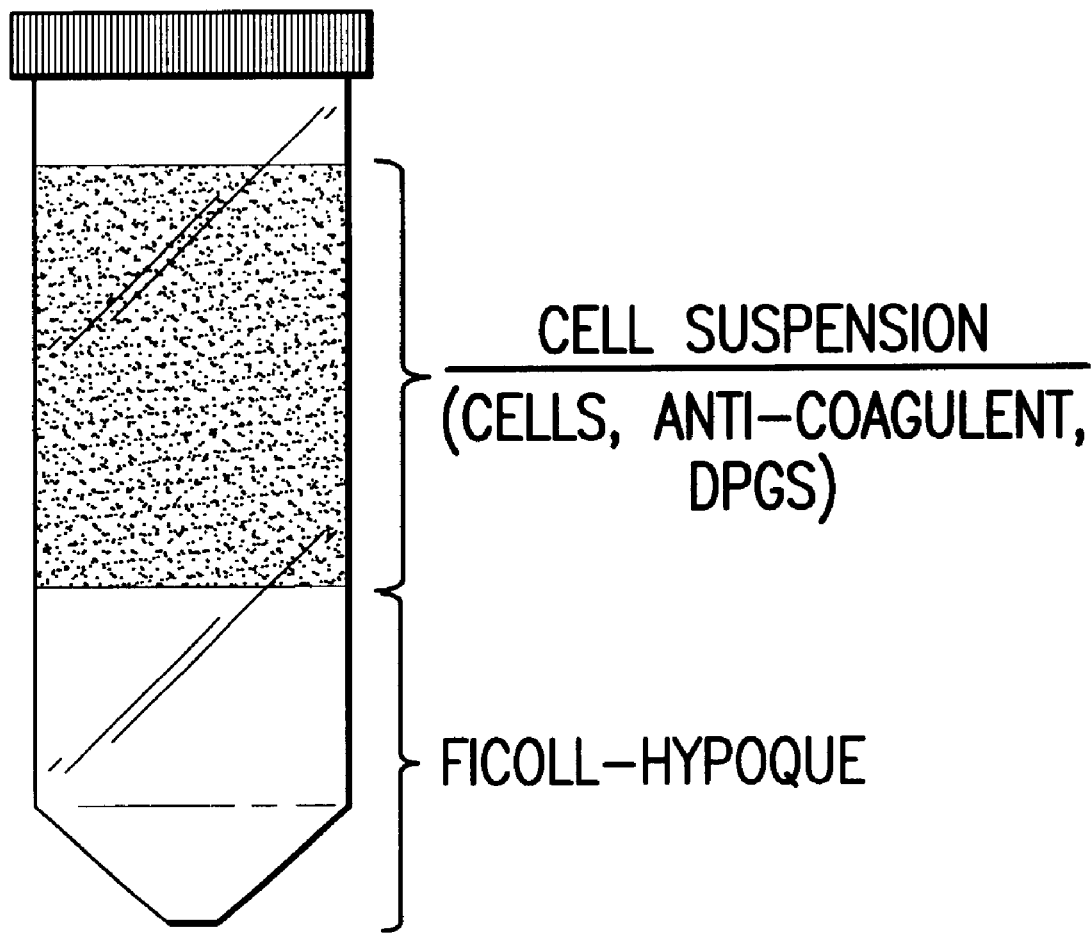
Figure 3B:
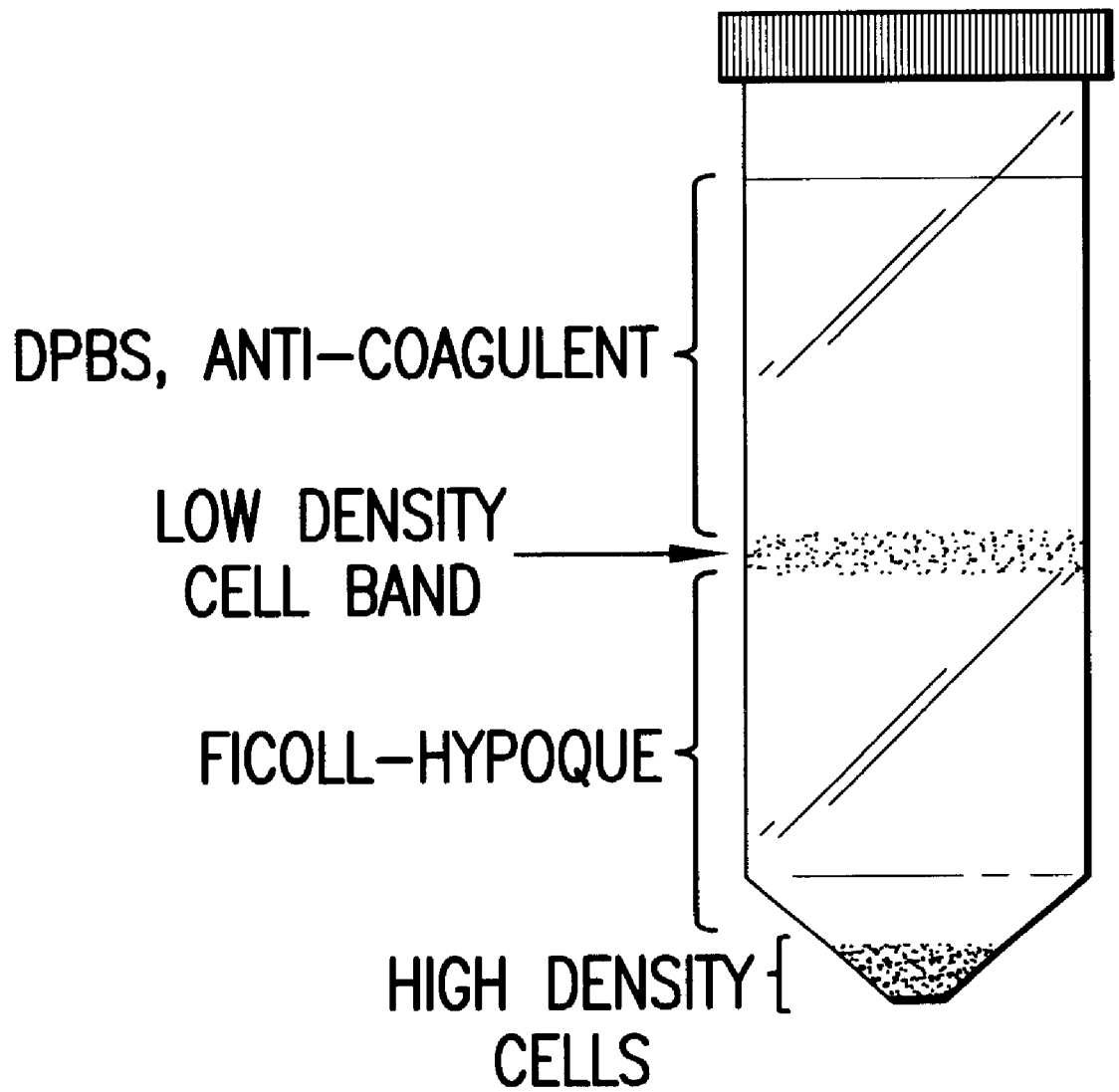

FIGS. 3A and 3B are diagrammatic representations of the composition of centrifuge tubes at different steps in a Ficoll-Hypaque density separation, as described in Section 6.3.1, which can be employed to obtain low density cells that are enriched in hematopoietic stem and progenitor cells. The cord blood cell suspension is layered on Ficoll-Hypaque before centrifugation (FIG. 3A). After centrifugation, the low density cells appear as a sharp band between the Ficoll-Hypaque and the phosphate-buffered saline (FIG. 3B).

Figure 4:
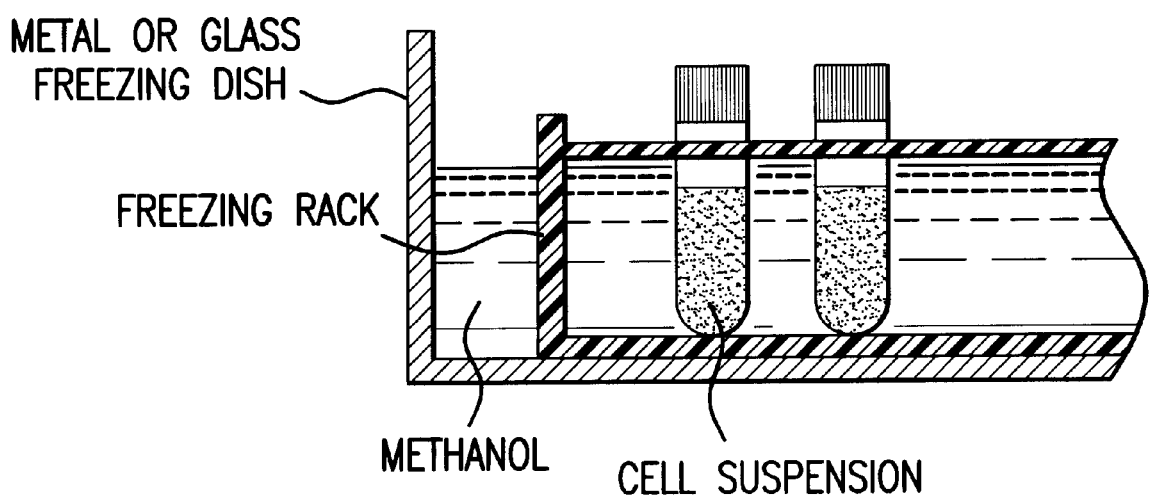

FIG. 4 is a diagrammatic representation of the apparatus described in Section 6.4, which can be used for the cryopreservation of neonatal and fetal hematopoietic stem and progenitor cells. The cryovials containing the cell suspensions are placed in a freezing rack which is in turn placed in a 4° C. methanol bath. The methanol bath (in a metal or glass freezing dish) is in turn placed in a −80° C. freezer. After the cells reach the frozen state, they are transferred to a long-term storage vessel containing liquid nitrogen.

5. DETAILED DESCRIPTION OF THE INVENTION

The present invention is directed to hematopoietic stem and progenitor cells of neonatal or fetal blood, that are cryopreserved, and the therapeutic uses of such stem and progenitor cells upon thawing.

In particular, the present invention relates to the use of fetal or neonatal stem cells for hematopoietic reconstitution. In a preferred embodiment of the invention, the fetal or neonatal stem cells can be used in autologous hematopoietic reconstitution, i.e., in the reconstitution of the hematopoietic system of the same individual from which they were originally derived. In such an embodiment, the invention provides substantial advantages over the present use of bone marrow for hematopoietic reconstitution. Present use of bone marrow transplantation is severely restricted by the fact that there is virtually never a perfectly matched (genetically identical) donor, except in cases where an identical twin is available or where bone marrow cells of, for example, a cancer patient in remission are stored in the viable frozen state in the hope that they will be free of malignant cells and healthy enough to be returned to the patient for treatment of any future relapse. Except in such cases, the inevitable genetic mismatch which results can entail the serious and sometimes lethal complications of host versus graft or graft versus host disease. In order to avoid host rejection of the foreign bone marrow cells (host versus graft reaction), the patient must be immunologically incapacitated. Such immune incapacitation is itself a cause of serious complications. Furthermore, when and if the donated bone marrow cells become established, they can attack the patient (graft versus host disease), who is recognized as foreign. Even with closely matched family donors, these complications of partial mismatching are the cause of substantial mortality and morbidity directly due to bone marrow transplantation from a genetically different individual.

In an embodiment of the invention directed to the use of neonatal stem and progenitor cells for hematopoietic reconstitution, there are several main reasons for preferring the use of such neonatal cells to conventional bone marrow transplantation. First, no donor is required because the cells can be obtained from neonatal blood that would otherwise be discarded. Second, in a preferred autologous system, i.e., involving use of "self" neonatal cells, the complications arising in conventional bone marrow transplantation from the need for pretransplantation drug-induced or irradiation-induced immune incapacitation and from acute and chronic graft-versus-host disease are all eliminated because, in this embodiment, neonatal cells are returned to their original owner and are therefore totally compatible. For these reasons, present restrictions on the use of bone marrow transplantation arising from difficulties in finding even approximately matched donors, and from disease and mortality due to unavoidable genetic incompatibility, do not apply to self-reconstitution with neonatal cells. Third, regarding the preferred autologous embodiment, the efficiency of genetically identical (self) cells in bone marrow transplantation in animals is numerically many times greater than that of cells from a genetically dissimilar donor (Balner, H., 1977, Bone Marrow Transplantation and Other Treatment after Radiation Injury, Martinus Nijhoff Medical Division, The Hague), thus far fewer self cells are required for successful reconstitution in the preferred autologous system.

Furthermore, the prospects of success in bone marrow transplantation decline with age; although it is not clear whether the age of donor or patient is more important, it is proper to infer that younger (neonatal) cells are preferable for hematopoietic reconstitution. Such neonatal or fetal cells have not been subjected to the "environmental outrage" that adult cells have undergone. Also, as an example of novel medical applications which may be feasible with neonatal cells but not with conventional bone marrow transplantation, restoration with self cells taken at birth can be valuable in the treatment of disorders such as declining immune responsiveness and autoimmunity (immune reactions against one's own tissues) which occur in increasing frequency with age.

Many of the relative disadvantages discussed supra of the use of bone marrow cells for hematopoietic reconstitution, also apply to the use of adult peripheral blood for such reconstitution, and thus, the use of neonatal cells for hematopoietic reconstitution according to the present invention provides distinct advantages over the employment of adult peripheral blood. It has been implied that the ability of autologous peripheral adult blood to reconstitute the hematopoietic system, seen in some cancer patients, is associated with the Car greater numbers of circulating progenitor cells in the peripheral blood produced after cytoreduction due to intensive chemotherapy and/or irradiation (the rebound phenomenon) (To, L. B. and Juttner, C. A., 1987, Annot., Brit. J., Haematol. 66:285–288; see also 1987, Brit. J. Haematol. 67:252–253, and references cited therein). There are possible detrimental effects, known or unknown, of prior chemotherapy or irradiation, on the stem and progenitor cell populations found in these patients.

There are additional reasons for preferring the use of neonatal cells for hematopoietic reconstitution as provided by the present invention. Neonatal blood is a preferred source of cells for hematopoietic reconstitution, since it is free from viral and microbial agents, known or unknown, latent or otherwise, that may be encountered in later life, other than those transmitted from the mother or during labor and delivery. In addition, in view of the extent to which the hematopoietic stem cell may possibly share with other cells the limitation in total number of cell divisions that it may undergo before senescence, it is proper to assume that the neonatal hematopoietic stem cell has a self-renewal and reconstituting capacity that is at least as great, and perhaps greater, than that of hematopoietic stem cells obtained at any later time in life.

In adults, stem and progenitor cells are mostly confined to the bone marrow; very few circulate in the blood. In the newborn human or animal, however, stem and progenitor cells circulate in the blood in numbers similar to those found in adult bone marrow. Doubtless this reflects the great demands for blood formation of the growing infant. We calculate that the restorative capacity of neonatal blood contained in the human umbilical cord and placenta, which are customarily discarded at birth, equals or exceeds that of the average donation of an adult's bone marrow. The efficacy of human neonatal blood cells compared with adult bone marrow cells is gauged by laboratory assays for stem cell and progenitor cells. Progenitor cell assays imply that the reconstituting potential of cells from 50 ml of cord blood (readily obtainable) is at least equivalent to the average number of progenitor cells from adult bone marrow that is used in autologous hematopoietic reconstitution (see Section 6.8, infra). 'S-cells', representing probably the earliest developmental form of the stem cell, are demonstrable in human (cord) blood (Nakahata, T. and Ogawa, M., 1982, J. Clin. Invest. 70:1324–1328). Thus, the cells of neonatal blood can be judged an effective clinical substitute for adult bone marrow.

In laboratory animals, the efficacy of neonatal cells can be tested directly. Accordingly we have shown that circulating neonatal cells, in numbers lower than are contained in the cord and placenta, will completely and permanently repopulate the entire blood-forming and immune systems of a lethally irradiated adult animal, promoting complete recovery and return to normal health (see Section 6.11, infra).

The method of the invention may be divided into the following stages solely for the purpose of description: (a) isolation of fetal or neonatal hematopoietic stem and progenitor cells; (b) inspection and testing of fetal or neonatal blood; (c) enrichment for hematopoietic stem and progenitor cells; (d) cryopreservation; (e) recovery of stem and progenitor cells from the frozen state; (f) examination of cells recovered for clinical therapy; and (g) therapeutic uses in reconstitution of the hematopoietic system.

Since both fetal and neonatal hematopoietic cells are envisioned for use in the present invention, descriptions and embodiments of the invention herein described for neonatal cells are meant to apply equally to fetal cells, unless clearly otherwise indicated or apparent.

5.1. Isolation of Fetal or Neonatal Hematopoietic Stem and Progenitor Cells

Fetal or neonatal blood are sources of the hematopoietic stem and progenitor cells of the present invention.

Fetal blood can be obtained by any method known in the art. For example, fetal blood can be taken from the fetal circulation at the placental root with the use of a needle guided by ultrasound (Daffos, F., et al., 1985, Am. J. Obstet. Gynecol. 153:655–660; Daffos, F., et al., 1983, Am. J. Obstet. Gynecol. 146:985), by placentocentesis (Valenti, C., 1973, Am. J. Obstet. Gynecol. 115:851; Cao, A., et al., 1982, J. Med. Genet. 19:81), by fetoscopy (Rodeck, C. H., 1984, in Prenatal Diagnosis, Rodeck, C. H. and Nicolaides, K. H., eds., Royal College of Obstetricians and Gynaecologists, London), etc.

In a preferred embodiment of the invention, neonatal hematopoietic stem and progenitor cells can be obtained from umbilical cord blood and/or placental blood. The use of cord or placental blood as a source of cells to repopulate the hematopoietic system provides numerous advantages. Cord blood can be obtained easily and without trauma to the donor. In contrast, at present, the collection of bone marrow cells for transplantation is a traumatic experience which is costly in terms of time and money spent for hospitalization. Cord blood cells can be used for autologous transplantation, when and if needed, and the usual hematological and immunological problems associated with the use of allogeneic cells, matched only partially at the major histocompatibility complex or matched fully at the major, but only partially at the minor complexes, are alleviated.

Collections should be made under sterile conditions. Immediately upon collection, the neonatal or fetal blood should be mixed with an anticoagulent. Such an anticoagulent can be any known in the art, including but not limited to CPD (citrate-phosphate-dextrose), ACD (acid citrate-dextrose), Alsever's solution (Alsever, J. B. and Ainslie, R. B., 1941, N. Y. St. J. Med. 41:126), De Gowin's Solution (De Gowin, E. L., et al., 1940, J. Am. Med. Ass. 114:850), Edglugate-Mg (Smith, W. W., et al.,. 1959, J. Thorac. Cardiovasc. Surg. 38:573), Rous-Turner Solution (Rous, P. and Turner, J. R., 1916, J. Exp. Med. 23:219), other glucose mixtures, heparin, ethyl biscoumacetate, etc. (See Hurn, B. A. L., 1968, Storage of Blood, Academic Press, New York, pp. 26–160). In a preferred embodiment, ACD can be used.

5.1.1. Collection of Neonatal Blood

The object of this aspect of the invention is to obtain a neonatal blood collection of adequate volume that is free of contamination. Since umbilical cord blood is a rich source of stem and progenitor cells (see Section 6.6, infra; Nakahata, T. and Ogawa, M., 1982, J. Clin. Invest. 70:1324–1328; Prindull, G., et al., 1978, Acta. Paediatr. Scand. 67:413–416; Tchernia, G., et al., 1981, J. Lab. Clin. Med. 97(3):322–331), the preferred source for neonatal blood is the umbilical cord and placenta. The neonatal blood can preferably be obtained by direct drainage from the cord and/or by needle aspiration from the delivered placenta at the root and at distended veins.

5.1.1.1. Volume

In a preferred embodiment, volumes of 50 ml or more of neonatal blood are obtained (see Section 6.1, infra).

Practical experience indicates that volumes of 50 ml or more are easily collected without additional measures in 80% of term births, and that collections of more than 40 ml are obtainable more than 90% of the time. Lower volumes may also be acceptable, and indicated under some circumstances (see Sections 5.1.1.2.3.1 and 5.1.1.2.3.2, infra).

The following information suggests that as little as 50 ml of cord blood contains enough of the appropriate cells to repopulate the hematopoietic system of an adult, and it is possible that even less cord blood would have the same effect:

1. In a small sampling of cases for autologous marrow transplantation (Spitzer, G., et al., 1980, Blood 55:317–323), rapid repopulation of hematopoiesis in patients with acute leukemia was associated with as few as 0.24 million granulocyte-macrophage progenitor cells (CFU-GM).

2. In human cord blood, there are approximately 50–200 CFU-GM per 100,000 low-density cells and at least 5 million low density cord blood cells per milliliter. Thus 50 milliliters of cord blood would contain in the range of 0.1 to greater than 0.5 million CFU-GM (see also Section 6.8, infra). The upper value agrees closely with estimations from the number of CFU-GM in 12.5 to 19 day old fetal blood (Lynch, D. C., et al., 1982, Blood 59:976–979).

3. Importantly, stem and progenitor cells in cord blood appear to have a greater proliferative capacity in culture dishes than those in adult bone marrow (Salahuddin, S. Z., et al., 1981, Blood 58:931–938; Cappellini, M. D., et al., 1984, Brit. J. Haematol. 57:61–70).

Significant to the use of cord blood as a source of stem cells, is that the assay for S-cells has been adapted for the growth of human cord blood (Nakahata, T. and Ogawa, M., 1982, J. Clin. Invest. 70:324–1328). All the known progenitor cells are present in cord blood in high numbers and this includes those progenitors for multilineages, granulocytes, macrophages, erythrocytes, mast cells, and basophils (id.; Fauser, A. A. and Messner, H. A., 1978, Blood 52:1243–1248; Koizumi, S., et al., 1982, Blood 60:1046–1049; Prindull, G., et al., 1978, Acta Paediatr. Scand. 67:413–416).

Furthermore, hematopoietic stem and progenitor cells can potentially be multiplied in culture, before or after cryopreservation, (see Sections 5.1.3.2, 5.3.2, infra), thus expanding the number of stem cells available for therapy.

5.1.1.2. Preferred Aspects

The following subsections provide detailed descriptions of preferred particular embodiments of the invention, and are intended for descriptive purposes only, in no way limiting the scope of the invention.

5.1.1.2.1. Collection Kit

In a preferred aspect, a collection kit, packaged in a sterile container, can be used. In one particular embodiment, the collection kit can consist of:

(i) a wide-mouth, graduated, collection container, with anticoagulant, into which the cut end of the cord may be placed for collection by gravity drainage. A small funnel can be provided for use if needed.

(ii) (optional) a plastic, flexible, sealed collection bag, similar to a donation bag, which has ports for injection of the collected blood, and contains anticoagulant.

(iii) an identification label, which identifies the infant source of the sample and time of collection.

For multiple births, separate collections, each performed with a separate kit, are preferred.

Sterilization of the containers can occur by any technique known in the art, including but not limited to beta-irradiation, autoclaving of suitable materials in a steam sterilizer, etc. For example, in a preferred embodiment, sterilization by beta-irradiation can be carried out by exposure to 2.5 megarads from a tungsten source (see Section 6.1, infra).

The collection kit may be placed in the surgical field in advance of a delivery, to afford ready availability.

5.1.1.2.2. Vaginal Delivery of the Term Infant

Vaginal delivery of the normal infant at term, spontaneously, by forceps, or as a breech delivery, should allow an ample collection of cord blood. After clamping the cord, the volume of fetal blood remaining in the cord and attached placenta has been estimated at 45 ml/kg infant body weight, or approximately 145 ml for a 7 lb (3.2 kg) baby (Hellman, L. M., et al., 1971, Williams Obstetrics, 14th Ed., Appleton-Century-Crofts, New York, p. 216).

Following delivery of the infant, by any method, with or without anesthesia, the infant is held in the plane of the vagina, and the cord is doubly cross-clamped and cut approximately three inches (7–8 cm) from the umbilicus. The infant is removed.

Maintaining usual sterile precautions, the cord is then transected just above the crushed portion in the clamp, and the resulting flow of fetal blood from umbilical vessels is caught in the container provided. An adequate collection can usually be accomplished without milking the cord, and is complete in approximately two minutes, before placental separation has occurred. Care should be taken to avoid contamination by maternal blood, urine, or other fluids in the delivery field. Blood in the container is then transferred to the bag provided for transport to the storage facility or, alternatively, the original container, if equipped with a tight screw cap, can itself be sent to the storage facility without transfer of its contents.

If, following infant delivery, events make collection at that time undesirable, collection can be done after delivery of the placenta (see Section 5.1.1.2.3.6, infra). If maternal infection is suspected, such a placental collection may be preferable. Collection can also be carried out by aspiration from the delivered placenta, in addition to gravity drainage.

In a most preferred embodiment, immediate cord clamping after delivery is carried out, in order to achieve collection of the greatest possible volume of cord blood. Studies have shown that the relative distribution of blood between the infant and placental circuits gradually shifts to the infant's blood circuits with increasing delay in cord clamping after delivery (Yao, A. C., et al., Oct. 25, 1969, Lancet: 871–873).

5.1.1.2.3. Other Circumstances of Birth and Delivery 5.1.1.2.3.1. Premature Birth The cord blood of premature infants may contain an even greater proportion of stem and progenitor cells than full-term cord blood. Consequently, smaller volumes of cord blood from premature infant delivery may give as good a yield of stem and progenitor cells. (The use of stem and progenitor cell assays as described in Sections 5.4.2 and 6.6 can determine the yield). Thus, in general, cord blood collection should be carried out if premature infant survival is anticipated, even though the volume of blood collected may be less than usual. Collection procedures should be the same as for term births.

5.1.1.2.3.2. Multiple Births

Cord blood collections undertaken at the time of multiple births involve additional procedural considerations:

(i) Multiple births are often premature, and volumes of cord blood will be correspondingly smaller. Collections should be made nevertheless, so that the decision o preserve for storage can be made later.

(ii) When births of two or more infants occur, where use of the cord collection is envisioned for later self-reconstitution, it is essential that each cord collection be identified with the proper infant. In cases of doubtful zygosity, blood typing can be done on cord blood an-d postnatal samples.

(iii) The timing of twin cord blood collection can be at the discretion of the obstetrician (after delivery of one twin; or after delivery of both).

(iv) A careful description of the placental relationships should be made (single or double amnions; single, double or fused chorions).

5.1.1.2.3.3. Caesarian Delivery

Cord blood collections at caesarean section can be carried out with the same kit, and with the same procedure, as vaginal delivery. The cut end of the cord is lowered to promote gravity drainage.

At caesarean section, it is strongly preferred that the cord blood collection be made after delivery of the infant, and before placental separation. However, this may not be desirable in some instances, such as where there is brisk hemorrhage, the need to incise or separate an anteriorly implanted placenta, or preoccupation of personnel with other events in the operating field. Thus, in these and similar cases, the placenta can be removed, and cord blood collected from it later.

5.1.1.2.3.4. Complication Delivery

Complications of delivery arising from the condition of the mother or the infant, or both, may require the immediate and urgent attention of the obstetrician and his assistants. Under these circumstances, the delivered placenta can be placed to one side, and collection carried out as soon as feasible.

5.1.1.2.3.5. Abnormal Placenta

For successful cord blood collection, it is preferred that the placenta be intact, or nearly so. Cases of marginal or partial separation can still offer an opportunity for collection, although it may have to be carried out after delivery of the placenta, if clinical circumstances indicate a need for prompt removal. Collections will be disfavored for use if a rupture of fetal circulation has occurred. Samples can be tested later for contamination by maternal blood (see Section 5.1.2, infra). Accurate description of the placental abnormality is preferred.

5.1.1.2.3.6. Collection from the Delivered Placenta

When rapid delivery of the placenta occurs or becomes necessary, and cord blood collection cannot be accomplished prior to placental separation, a sample of sufficient volume can still be obtained after delivery. The placenta and attached cord, still clamped, are placed to one side, but still within the sterile field. Collection is by the same technique described supra in section 5.1.1.2.2. It is preferred, however, that collection be completed within five minutes of delivery, while maintaining sterile procedures.

Cord blood collection prior to placental separation is preferred over collection from the delivered placenta for the following reasons: In a collection from delivered placenta, (i) collection volumes are generally less; (ii) some degree of clotting in the placental circulation may restrict recovery, and (iii) the likelihood of contamination, by maternal blood or other agents, is increased. Therefore, the determination of suitability of the sample collected from a delivered placenta is especially important.

5.1.1.2.3.7. Medical Conditions of the Mother

Given the general prohibition against maternal use of drugs which would adversely affect the fetus, it is unlikely that maternal therapy or medical status in the general sense would adversely affect stem cell retrieval from cord blood collection of a normal infant. In a preferred embodiment, however, specific information should be obtained in regard to drug abuse, vira-diseases capable of vertical transmission, and the influence of acute maternal illness at the time of delivery, since it is possible that these may affect stem cell retrieval from cord blood.

5.1.1.2.3.8. Unplanned Delivery

Despite elaborate plans, delivery may occur inopportunely, sometimes prematurely, and without the immediate services of a physician. Under these circumstances, the following procedures are preferred: (i) cord blood collection should be attempted with the standard kit, described supra; (ii) the placenta, if delivered on an unsterile field, should simply be kept as clean as possible, left with the cord clamped, and collection attempted within 5 minutes; (iii) the cord should be wiped with a cleansing agent (e.g. Betadine), and transected above the clamp, to make the collection; and (iv) circumstances of the delivery should be described with the specimen.

5.1.1.2.4. Recordation of Data

In a preferred embodiment, the data listed in Table I, infra, are obtained at the time of collection in order to ensure the accurate identification and evaluation of the collected blood.

TABLE I

DATA TO BE RECORDED AT THE
TIME OF NEONATAL BLOOD COLLECTION

Date and time of delivery
Full name and address of mother
Hospital identification

TABLE I-continued

DATA TO BE RECORDED AT THE TIME OF NEONATAL BLOOD COLLECTION

Sex of infant
Weight of infant
Birth order (for multiple pregnancies)
Gestational age
Pregnancy complications
Intrapartum complications
Type of delivery
Placental collection (amount of blood collected)
Placental description and weight
Condition of infant 5.1.2. Inspection and Testing of Neonatal Blood In a preferred embodiment, the neonatal blood sample is inspected and tested to ensure its suitability. Appropriate inspections and tests include but are not limited to the procedures described infra.

If the blood collection sample is to be shipped to a processing plant, the blood container and its contents should be inspected for defects such as inadequate closure and leakage. As an option, the collection kit may include a suitably positioned reusable maximum-minimum mercury thermometer to register the range of temperature change during shipment. Clots, opacity of the plasma and visible hemolysis are indications of bacterial contamination or other consequences of faulty handling. Time elapsed since collection can be noted.

The following tests on the collected neonatal blood sample can be performed either routinely, or where clinically indicated:

(i) Bacterial culture: To ensure the absence of microbial contamination, established assays can be performed, such as routine hospital cultures for bacteria under aerobic and anaerobic conditions.

(ii) Diagnostic screening for pathogenic microorganisms: To ensure the absence of specific pathogenic microorganisms, various diagnostic tests can be employed. Diagnostic screening for any of the numerous pathogens transmissible through blood can be done by standard procedures. As one example, the collected blood sample can be subjected to diagnostic screening for the presence of Human Immunodeficiency Virus (HIV), the causative agent of Acquired Immune Deficiency Syndrome (AIDS) (Gallo et al., 1984, Science 224:500–503; Barre-Sinoussi, F., et al., 1983, Science 220:868; Levy, J. A., et al., 1984, Science 225:840). Any of numerous assay systems can be used, based on the detection of virions, viral-encoded proteins, HIV-specific nucleic acids, antibodies to HIV proteins, etc.

(iii) Confirmation of neonatal origin of the blood: Contamination with maternal blood, not necessarily a contraindication to storage and clinical utility, may be suspected from the obstetrical history. Presence of maternal cells, and of adult blood generally, can be revealed by various tests, including but not limited to I typing (Wiener, A. S., et al., 1965, Am. J. Phys. Anthropol. 23(4): 389–396); analysis on a Coulter Channelyzer, which detects size differences between neonatal and maternal blood cells (Daffos, F., et al., 1985, Am. J. Obstet. Gynecol. 153:655–660); staining procedures for hemoglobin such as the Kleinhauer-Betke technique (Betke, K., 1968, Bibl. Haematologica 29:1085) and others (Clayton, E. M., et al., 1970, Obstetrics and Gynecology 35(4):642–645), which detect differences in the types of hemoglobin contained in red blood cells before birth versus in later life; etc.

In a preferred embodiment, I typing can be done by established methods, such as agglutination with anti-i and anti-I antibodies. Erythrocytes of neonates are i strong, c weak; by 18 months of age, erythrocytes are I strong; i weak (Marsh, W. L., 1961, Brit. J. Haemat. 7:200). Thus, the degree of reaction with anti-i or anti-I antibodies is a measure of the proportion of neonatal blood and red cells in a mixture of neonatal and adult blood. The corresponding contamination with maternal stem and progenitor cells would be far less than the total maternal cell contamination since the stem and progenitor cells are rare in adult blood. (Scarcity of stem and progenitor cells in colony assays (see Sections 5.4.2 and 6.6, infra) is another distinction between neo natal and adult blood.)

5.1.3. Optional Procedures

In a preferred embodiment of the invention, whole neonatal blood, as collected, can be cryogenically frozen, thus minimizing cell losses which can be incurred during cell processing protocols. However, cell separation procedures and expansion of stem and progenitor cells in in vitro cultures remain options. Such procedures may be useful, e.g., in reducing the volume of sample to be frozen, and increasing cell count, respectively. The procedures described infra in Sections 5.1.3.1 and 5.1.3.2 should be carefully screened before use, in order to ensure that hematopoietic stem and progenitor cell loss in processing does not endanger the therapeutic efficacy of a collected blood sample in hematopoietic reconstitution.

5.1.3.1. Enrichment for Hematopoietic Stem and Progenitor Cells: Cell Separation Procedures After receiving cord blood or bone marrow samples in anticoagulant (e.g., ACD), the cells can be subjected to physical and/or immunological cell separation procedures. Such procedures enrich for the hematopoietic stem and progenitor cells so that fewer total cells have to be stored and transplanted. However, if cell separation is desired, care should be taken to ensure sufficient recovery of the hematopoietic stem and progenitor cells.

Various procedures are known in the art and can be used to enrich for the stem and progenitor cells of the present invention. These include but are not limited to equilibrium density centrifugation, velocity sedimentation at unit gravity, immune rosetting and immune adherence, counter-flow centrifugal elutriation, T lymphocyte depletion, and fluorescence-activated cell sorting, alone or in combination. Recently, procedures have been reported for the isolation of very highly enriched populations of stem/progenitor cells. Murine CFU-S have been purified by several groups using slightly different procedures (Visser, J. W. M., et al., 1984, J. Exp. Med. 59:1576; Nijhof, W., et al., 1984, Exp. Cell Res. 155:583; Bauman, J. G. J., et al., 1986, J. Cell. Physiol. 128:133; Lord, B. I. and Spooncer, E., 1986, Lymphokine Res. 5:59). Studies using human (Emerson, S. G., et al., 1985, J. Clin. Invest. 76:1286) or murine (Nicola, N. A., et al., 1981, Blood 58:376) fetal liver cells have yielded highly enriched progenitor cells with up to 90% of them being colony forming cells for multi-, erythroid-, and granulocyte-macrophage lineages. CFU-E have also been very highly enriched (Nijhof, W., et al., 1983, J. Cell Biol. 96:386). Purification of adult mouse marrow CFU-GM with cloning efficiencies of up to 99% in semi-solid medium has been accomplished by pretreatment of mice three days prior to sacrifice with cyclophosphamide, density separation of cells on Ficoll-Hypaque, and counterflow centrifugal elutriation (Williams, D. E., et al., 1987, Exp. Hematol. 15:243). The resulting fraction of cells contained no detectable CFU-GEMM, BFU-E or CFU-MK, but up to 10% of the cells formed CFU-S measured at day 12. These procedures, or modifications thereof, can be used, and are within the scope of the present invention.

Human stem and progenitor cells are present in the non-adherent, low density, T-lymphocyte-depleted fraction of bone marrow, spleen, and (adult and cord) blood cells. In a specific embodiment, low density (density less than 1.077 gm/cm) cells can be separated by use of Ficoll-Hypaque (Pharmacia Fine Chemicals, Piscataway, N.J.) (see Section 6.3.1, infra) or Percol (Broxmeyer, H. E., 1982, J. Clin. Invest. 69:632–642). In this procedure, the mature cells of the granulocytic series, which are not needed for transplantation, are removed in the dense fraction which goes to the bottom of the tube. An adherence/nonadherence separation protocol can also be used for enrichment of hematopoietic stem and progenitors; protocols which can be used are described in Section 6.3.2, infra, and in Broxmeyer, H. E., et al., 1984, J. Clin. Invest. 73:939–953, which is incorporated by reference herein.

If desired, autologous plasma can be removed for use in the freezing process. In particular, the blood or marrow samples can be allowed to settle at unit gravity in a test tube. The setting process can be hastened by addition of sterile-pyrogen-free Dextran Sulphate. After approximately 15 minutes, the upper layer containing the nucleated cells in plasma can be removed and centrifuged (e.g., 200–400×g). The nucleated cells pellet to the bottom of the tube and the plasma is removed and stored in a tube at 4° C. The nucleated cells are washed, counted and, if desired, further separated (e.g., by use of a density "cut" procedure with Ficoll-Hypaque or Percol).

In order to enrich hematopoietic stem and progenitor cells, it is also possible to use cell separation procedures that entail immunological recognition of cells. Stem and progenitor cells can be isolated by positive or negative selection using antibodies that recognize antigenic determinants on the surface of cells. One means is to separate the cells by using monoclonal antibodies which recognize cell surface determinants on these cells, in conjunction with separation procedures such as fluorescence-activated cell sorting or panning (Broxmeyer, H. E., et al., 1984, J. Clin. Invest. 73:939–953). At present, there are no known antigenic determinants that are absolutely specific for human hematopoietic stem and progenitor cells. However, these cells do contain antigenic determinants that are not present on all other cells, which can be used in antibody selection protocols for enrichment purposes; such antigens include but are not limited to those described infra.

Within the human system, several antigens have been found on stem/progenitor cells. The first antigenic system studied intensively was that of the MHC class II antigens, especially HLA-DR. This has been found on CFU-GEMM, BFU-E, and CFU-GM (Lu, L., et al., 1983, Blood 61:250; Winchester, R. J., et al., 1977, Proc. Natl. Acad. Sci. U.S.A. 74:4012; Busch, F. W., et al., 1987, Blut 54:179). Several investigators have suggested that HLA-DR are not found, or are present at a low density on cells earlier than CFU-GEMM (Moore, M. A. S., et al., 1980, Blood 55:682; Keating, A., et al., 1984, Blood 64:1159) but others have not agreed (e.g., Falkenberg, J. H. F., et al., 1985, J. Exp. Med. 162:1359). This discrepancy may be due to the existence of specific subsets of early progenitors. In fact, the expression of HLA-DR is higher during the S-phase of the cell cycle of hematopoietic progenitor cells (Broxmeyer, H. E., 1982, J. Clin. Invest. 69:632; Cannistra, S. A., et al., 1985, Blood 65:414). Day 14 CFU-GM express higher levels of HLA-DR than day 7 CFU-GM, and among day 7 CFU-GM, monocyte progenitors express more HLA-DR than do the granulocyte progenitors (Griffin, J. D., et al., 1985, Blood 66:788). Expression of HLA-DR decreases and is lost during early myeloid precursor cell states and it has been suggested that HLA-DR antigens might play a role in myeloid development (Winchester, R. J., et al., 1977, supra).

Groups of antibodies have been used to distinguish different progenitors of the granulocyte-macrophage lineage (Ferrero, D., et al., 1983, Proc. Natl. Acad. Sci. U.S.A. 80:4114). Type 1 CFU-GM contribute all of the peripheral blood CFU-GM, as well as a small number of bone marrow CFU-GM. They express surface antigens recognized by S3-13 and S17-25 antibodies, but not by R1B19 and WGHS-29-1 antibodies. Type 2 CFU-GM are present only in the marrow and react with S3-13, R1B19, and WGHS-29-1. Culture of type 1 CFU-GM in liquid culture generates type 2 CFU-GM. These antibodies have also been used to characterize CFU-GM from patients with chronic myeloproliferative disorders (Robak, T., et al., 1985, Leukemia Res. 9:1023; Ferrero, D., et al., 1986, Cancer Res. 46:975).

Other antigens on human stem/progenitor cells include those reactive with the My10 (Leary, A. G., et al., 1987, Blood 69:953; Strauss, L. C., et al., 1986, Exp. Hematol. 14:879), 3C5 (Katz, F. E., et al., 1985, Leukemia Res. 9:191; Katz, F. E., et al., 1986, Leukemia Res. 10:961), RFB-1 (Bodger, M. P., et al., 1983, Blood 61:1006), 12-8 (Andrews, R. G., et al., 1986, Blood 67:842), and L4F3 (Andrews, R. G., et al., 1986, Blood 68:1030) antibodies. The antigen recognized by L4F3 is on CFU-GM, CFU-MK, BFU-E, and CFU-GEMM, but is apparently absent from cells which generate these progenitors in suspension culture (id.). L4F3 reacts with most blast cells from patients with acute myelogenous leukemia, and treatment of cells from such patients with L4F3 has allowed the growth of normal progenitor cells in vitro (Bernstein, I. D., et al., 1987, J. Clin. Invest. 79:1153).

The antigen recognized by another antibody, My11, is expressed on CFU-GM, but not on BFU-E or CFU-GEMM (Strauss, L.C., et al., 1986, Exp. Hematol. 14:935). Receptors for various lectins are also expressed on stem/progenitors (Nicola, N. A., et al., 1980, J. Cell Physiol. 103:217, Reisner, Y., et al., 1982, Blood 59:360; Reisner, Y., et al., 1978, Proc. Natl. Acad. Sci. U.S.A. 75:2933; Aizawa, S., and Tavassoli, M., 1986, Int. J. Cell Cloning 4:464).

Some success in enriching adult human bone marrow progenitor cells has been reported based on the use of monoclonal antibodies and cell sorting. In some studies, cells have been sorted only on positive versus negative populations (Katz, F. E., et al., 1986, Leukemia Res. 10:961). Recently, My10 and HLA-DR antibodies were used in association with two color sorting to obtain highly enriched progenitor cell populations from human marrow (Lu, L., et al., 1987, J. Immunol. 139(6):1823–1829).

In specific embodiments, antibodies which are currently available and can be used in enrichment protocols include My-10, 3C5, or RFB-1. These antibodies can be used alone or in combination with procedures such as panning (Broxmeyer, H. E., et al., 1983, J. Clin. Invest. 73:939–953) or fluorescence activated cell-sorting (FACS) (Williams, D. E., et al., 1985, J. Immunol. 135:1004; Lu, L., et al., 1986, Blood 68(1):126–133) to isolate those cells containing surface determinants recognized by the monoclonal antibodies.

In another embodiment, enrichment, if desired, can proceed by the use of monoclonal antibodies to major histocompatibility (MHC) class II antigens (especially HLA-DR) and to My10 (Lu, L., et al., 1987, J. Immunol. 139(6): 1823–1829.

T lymphocyte depletion can also be used to enrich for hematopoietic stem or progenitor cells. In this procedure, T lymphocytes are selectively removed from the cell-population by pretreating cells with a monoclonal antibody (ies), that recognize a T cell antigen, plus complement. Such a procedure has been described previously (Broxmeyer, H. E., et al., 1984, J. Clin. Invest. 73:939–953).

Another method that can be used is that of separating the stem and progenitor cells by means of selective agglutination using a lectin such as soybean (Reisner, Y., et al., 1980, Proc. Natl. Acad. Sci. U.S.A. 77:1164). This procedure can be a viable alternative for separation and enrichment of stem and progenitor cells without removal of possibly necessary accessory cells (Reisner, Y., et al., 1983, Blood 61(2):341–348; Reisner, Y., et al., 1982, Blood 59(2):360–363).

Theoretically, only one early stem cell is needed for repopulation of the entire hematopoietic system. There is laboratory evidence that under ideal conditions and when the microenvironment nurturing the stem and progenitor cells in the recipient animal is not affected, a single stem cell can entirely repopulate the defective hematopoietic system of a mouse and rescue it from the lethal complications of anemia (Boggs, D. R., et al., 1982, J. Clin. Invest. 70:242–253). Doubtless, under clinical conditions in man it would generally require more than a single stem cell to rescue the hematopoietic system. Moreover, the presence of accessory or helper cells (non-stem/progenitor cells that influence the growth of stem/progenitor cells), in addition to stem and progenitor cells, may be required (Spooncer, F., et al., 1985, Nature (London) 316:62–64), especially if the microenvironment of the host is injured by treatments such as irradiation or chemotherapy. Thus, while there are ways to separate hematopoietic stem and progenitor cells from other cord blood cells (Leary, A. G., et al., 1984, J. Clin. Invest. 74:2193–2197) and these and other methods could be used to isolate and store pure or highly enriched preparations of these cells for transplantation, caution should be used in attempts at transplanting patients with purified preparations of stem and progenitor cells.

5.1.3.2. In Vitro Cultures of Hematopoietic Stem and Progenitor Cells

An optional procedure (either before or after cryopreservation) is to expand the hematopoietic stem and progenitor cells in vitro. However, care should be taken to ensure that growth in vitro does not result in the production of differentiated progeny cells at the expense of multipotent stem and progenitor cells which are therapeutically necessary for hematopoietic reconstitution. Various protocols have been described for the growth in vitro of cord blood or bone marrow cells, and it is envisioned that such procedures, or modifications thereof, may be employed (see Section 6.9 infra; Smith, S. and Broxmeyer, H. E., 1986, Br. J. Haematol. 63:29–34; Dexter, T. M., et al., 1977, J. Cell. Physiol. 91:335; Witlock, C. A. and Witte, O. N., 1982, Proc. Natl. Acad. Sci. U.S.A. 79:3608–3612). Various factors can also be tested for use in stimulation of proliferation in vitro, including but not limited to interleukin-3 (IL-3), granulocyte-macrophage (GM)-colony stimulating factor (CSF), IL-1 (hemopoietin-1), IL-4 (B cell growth factor), IL-6, alone or in combination.

5.2. Cryopreservation

The freezing of cells is ordinarily destructive. On cooling, water within the cell freezes. Injury then occurs by osmotic effects on the cell membrane, cell dehydration, solute concentration, and ice crystal formation. As ice forms outside the cell, available water is removed from solution and withdrawn from the cell, causing osmotic dehydration and raised solute concentration which eventually destroy the cell. (For a discussion, see Mazur, P., 1977, Cryobiology 14:251–272.)

These injurious effects can be circumvented by (a) use of a cryoprotective agent, (b) control of the freezing rate, and (c) storage at a temperature sufficiently low to minimize degradative reactions.

Cryoprotective agents which can be used include but are not limited to dimethyl sulfoxide (DMSO) (Lovelock, J. E. and Bishop, M. W. H., 1959, Nature 183:1394–1395; Ashwood-Smith, M. J., 1961, Nature 190:1204–1205), glycerol, polyvinylpyrrolidine (Rinfret, A. P., 1960, Ann. N. Y. Acad. Sci. 85:576), polyethylene glycol (Sloviter, H. A. and Ravdin, R. G., 1962, Nature 196:548), albumin, dextran, sucrose, ethylene glycol, i-erythritol, D-ribitol, D-mannitol (Rowe, A. W., et al., 1962, Fed. Proc. 21:157), D-sorbitol, i-inositol, D-lactose, choline chloride (Bender, M. A., et al., 1960, J. Appl. Physiol. 15:520), amino acids (Phan The Tran and Bender, M. A., 1960, Exp. Cell Res. 20:651), methanol, acetamide, glycerol monoacetate (Lovelock, J. E., 1954, Biochem. J. 56:265), and inorganic salts (Phan The Tran and Bender, M. A., 1960, Proc. Soc. Exp. Biol. Med. 104:388; Phan The Tran and Bender, M. A., 1961, in Radiobiology, Proceedings of the Third Australian Conference on Radiobiology, Ilbery, P. L. T., ed., Butterworth, London, p. 59). In a preferred embodiment, DMSO is used, a liquid which is nontoxic to cells in low concentration. Being a small molecule, DMSO freely permeates the cell and protects intracellular organelles by combining with water to modify its freezability and prevent damage from ice formation. Addition of plasma (e.g., to a concentration of 20–25%) can augment the protective effect of DMSO. After addition of DMSO, cells should be kept at 0° C. until freezing, since DMSO concentrations of about 1% are toxic at temperatures above 4° C.

A controlled slow cooling rate is critical. Different cryoprotective agents (Rapatz, G., et al., 1968, Cryobiology 5(1):18–25) and different cell types have different optimal cooling rates (see e.g., Rowe, A. W. and Rinfret, A. P., 1962, Blood 20:636; Rowe, A. W., 1966, Cryobiology 3(1):12–18; Lewis, J. P., et al., 1967, Transfusion 7(1):17–32; and Mazur, P., 1970, Science 168:939–949 for effects of cooling velocity on survival of marrow-stem cells and on their transplantation potential). The heat of fusion phase where water turns to ice should be minimal. The cooling procedure can be carried out by use of, e.g., a programmable freezing device or a methanol bath procedure.

Programmable freezing apparatuses allow determination of optimal cooling rates and facilitate standard reproducible cooling. Programmable controlled-rate freezers such as Cryomed or Planar permit tuning of the freezing regimen to the desired cooling rate curve. For example, for marrow cells in 10% DMSO and 20% plasma, the optimal rate is 1 to 3° C./minute from 0° C. to −80° C. In a preferred embodiment, this cooling rate can be used for the neonatal cells of the invention. The container holding the cells must be stable at cryogenic temperatures and allow for rapid heat transfer for effective control of both freezing and thawing. Sealed plastic vials (e.g., Nunc, Wheaton cryules) or glass ampules can be used for multiple small amounts (1–2 ml), while larger volumes (100–200 ml) can be frozen in polyolefin bags (e.g., Delmed) held between metal plates for better heat transfer during cooling. (Bags of bone marrow cells have been successfully frozen by placing them in −80° C. freezers which, fortuitously, gives a cooling rate of approximately 3° C./minute).

In an alternative embodiment, the methanol bath method of cooling can be used. The methanol bath method is well-suited to routine cryopreservation of multiple small items on a large scale. The method does not require manual control of the freezing rate nor a recorder to monitor the rate. In a preferred aspect, DMSO-treated cells are precooled on ice and transferred to a tray containing chilled methanol which is placed, in turn, in a mechanical refrigerator (e.g., Harris or Revco) at −80° C. Thermocouple measurements of the methanol bath and the samples indicate the desired cooling rate of 1 to 3° C./minute. After at least two hours, the specimens have-reached a temperature of −8° C. and can be placed directly into liquid nitrogen (−196° C.) for permanent storage.

After thorough freezing, cells can be rapidly transferred to a long-term cryogenic storage vessel. In a preferred embodiment, samples can be cryogenically stored in liquid nitrogen (−196° C.) or its vapor (−165° C.). Such storage is greatly facilitated by the availability of highly efficient liquid nitrogen refrigerators, which resemble large Thermos containers with an extremely low vacuum and internal super insulation, such that heat leakage and nitrogen losses are kept to an absolute minimum.

In a particular embodiment, the cryopreservation procedure described in Section 6.4 infra is envisioned for use. The sterilized storage cryules preferably have their caps threaded inside, allowing easy handling without contamination. Suitable racking systems are commercially available and can be used for cataloguing, storage, and retrieval of individual specimens.

Considerations and procedures for the manipulation, cryopreservation, and long-term storage of hematopoietic stem cells, particularly from bone marrow or peripheral blood, is largely applicable to the neonatal and fetal stem cells of the invention. Such a discussion can be found, for example, in the following references, incorporated by reference herein: Gorin, N. C., 1986, Clinics In Haematology 15(1):19–48; Bone-Marrow Conservation, Culture and Transplantation, Proceedings of a Panel, Moscow, Jul. 22–26, 1968, International Atomic Energy Agency, Vienna, pp. 107–186.

Other methods of cryopreservation of viable cells, or modifications thereof, are available and envisioned for use (e.g., cold metal-mirror techniques; Livesey, S. A. and Linner, J. G., 1987, Nature 327:255; Linner, J. G., et al., 1986, J. Histochem. Cytochem. 34(9):1123–1135; see also U.S. Pat. No. 4,199,022 by Senkan et al., U.S. Pat No. 3,753,357 by Schwartz, U.S. Pat No. 4,559,298 by Fahy; and Section 2.3, supra).

5.3. Recovering Stem and Progenitor Cells from the Frozen State 5.3.1. Thawing Frozen cells are preferably thawed quickly (e.g., in a water bath maintained at 37–41° C.) and chilled immediately upon thawing. In particular, the vial containing the frozen cells can be immersed up to its neck in a warm water bath; gentle rotation will ensure mixing of the cell suspension as it thaws and increase heat transfer from the warm water to the internal ice mass. As soon as the ice has completely melted, the vial can be immediately placed in ice (see Section 6.5, infra).

5.3.2. Optional Procedures

In a preferred embodiment of the invention, the neonatal blood sample as thawed can be infused for hematopoietic reconstitution. Thus, it is envisioned that whole neonatal blood, cryopreserved and thawed, can be infused for therapy. However, several procedures, relating to processing of the thawed cells are available, and can be employed if deemed desirable. Such procedures are discussed infra.

It may be desirable to treat the cells in order to prevent cellular clumping upon thawing. To prevent clumping, various procedures can be used, including but not limited to, the addition before and/or after freezing of DNase (Spitzer, G., et al., 1980, Cancer 45:3075–3085), low molecular weight dextran and citrate, hydroxyethyl starch (Stiff, P. J., et al., 1983, Cryobiology 20:17–24), etc.

The cryoprotective agent, if toxic in humans, should be removed prior to therapeutic use of the thawed neonatal stem and progenitor cells. In an embodiment employing DMSO as the cryopreservative, it is preferable to omit this step in order to avoid cell loss, since DMSO has no serious toxicity. However, where removal of the cryoprotective agent is desired, the removal is preferably accomplished upon thawing.

One way in which to remove the cryoprotective agent is by dilution to an insignificant concentration. This can be accomplished by addition of medium, followed by, if necessary, one or more cycles of centrifugation to pellet cells, removal of the supernatant, and resuspension of the cells. For example, intracellular DMSO in the thawed cells can be reduced to a level (less than 1%) that will not adversely affect the recovered cells. This is preferably done slowly to minimize potentially damaging osmotic gradients that occur during DMSO removal (see Section 6.5, infra.)

After removal of the cryoprotective agent, cell count (e.g., by use of a hemocytometer) and viability testing (e.g., by trypan blue exclusion; Kuchler, R. J. 1977, Biochemical Methods in Cell Culture and Virology, Dowden, Hutchinson & Ross, Stroudsburg, Pa., pp. 18–19; 1964, Methods in Medical Research, Eisen, H. N., et al., eds., Vol. 10, Year Book Medical Publishers, Inc., Chicago, pp. 39–47) can be done to confirm cell survival.

Other procedures which can be used, relating to processing of the thawed cells, include enrichment for hematopoietic stem and progenitor cells (see Section 5.1.3.1, supra) and expansion by in vitro culture (see Section 5.1.3.2, supra). However, in a preferred embodiment, these steps can be omitted in order to minimize cell loss.

5.4. Examination of Cells Recovered for Clinical Therapy

In a preferred, but not required, aspect of the invention, thawed cells are tested by standard assays of viability (e.g., trypan blue exclusion) and of microbial sterility (see Section 5.1.2, supra), and tested to confirm and/or determine their identity relative to the patient, and for hematopoietic function.

5.4.1. Identity Testing

Methods for identity testing which can be used include but are not limited to HLA (the major histocompatibility complex in man) typing (Bodmer, W., 1973, in Manual of Tissue Typing Techniques, Ray, J. G., et al., eds., DHEW Publication No. (NIH) 74–545, pp. 24–27), and DNA fingerprinting, which can be used to establish the genetic identity of the cells. DNA fingerprinting (Jeffreys, A. J., et al., 1985, Nature 314:67–73) exploits the extensive restriction fragment length polymorphism associated with hypervariable minisatellite regions of human DNA, to enable identification of the origin of a DNA sample, specific to each individual (Jeffreys, A. J., et al., 1985, Nature 316:76; Gill, P., et al., 1985, Nature 318:577; Vassart, G., et al., 1987, Science 235:683), and is thus preferred for use.

In a specific embodiment of the invention in which the cells recovered for therapy are to be used in an autologous system, the cells should match exactly the recipient patient from whom they originally came.

5.4.2. Assays for Stem and Progenitor Cells

Any of numerous assays for hematopoietic stem or progenitor cells may be used (see Section 2.1). Examples of specific assays are described in Section 6.6 and subsections, infra. Modifications of the assays therein described are also envisioned for use. For example, various factors, alone or in combination, can be tested for stimulation of colony formation upon inclusion in the culture mixture (see Broxmeyer, H. E., 1986, Int. J. Cell Cloning 4:378–405; Lu, L. and Broxmeyer, H. E., 1983, Exp. Hematol. 11(8):721–729; Lu, L. and Broxmeyer, H. E., 1985, Exp. Hematol. 13:989–993); such factors include but are not limited to oxygen tension, E-type prostaglandins, interleukin-3 (IL-3), granulocyte-macrophage (GM)-colony stimulating factor (CSF), granulocyte (G)-CSF, macrophage (M)-CSF (CSF-1), erythropoietin, IL-1, IL-4 (B cell growth factor), hemin (ferric chloride protoporphyrin IX), and media conditioned by various cell types. Culture assay methods may thus be changed to employ more efficient conditions for colony growth. In addition to in vitro colony forming assays, a stem cell assay for CFU-S (colony forming unit-spleen) can be done. In this assay, cells considered to be multipotential stem cells with self-renewal capacity can be measured by counting the number of colonies (nodules) on the spleen(s) of lethally-irradiated mice that have been inoculated with a composition containing the cells.

In a particular embodiment, low density Ficoll-Hypaque-separated cells (density less than 1.077 gm/cm$^3$), which include the stem and progenitor cells, are plated, usually $0.5–2.0×10^5$ per plate, for recognition of S (stem).cells, and progenitor cells of the CFU-GEMM (multipotent) and CFU-GM and BFU-E (more differentiated) categories.

5.5 Hematopoietic Reconstitution

The neonatal hematopoietic stem and progenitor cells of the present invention can be used therapeutically for hematopoietic reconstitution, with either syngeneic or allogeneic hosts. The neonatal cells can be introduced into a patient for repopulation of the blood and other hematopoietic organs in the treatment or prevention of various diseases or disorders, as described infra in Section 5.6. Introduction of the neonatal cells can occur by any method known in the art, with systemic infusion of cells being the preferred route.

In a preferred embodiment of the invention, the neonatal cells are autologous (self) cells, i.e., the cells were originally derived from the host recipient. Such an embodiment avoids the immunosuppressive regimens (e.g., irradiation, chemotherapy) which are often necessary in allogeneic transplants in order to avoid debilitating graft versus host or host versus graft disease.

5.6. Therapeutic Uses

Reconstitution of the hematopoietic system (or immune system) with the neonatal stem and progenitor cells of the present invention can be therapeutically valuable for a large number of diseases and disorders.

In a preferred embodiment involving the use of autologous neonatal cells, the infusion of previously cryopreserved neonatal hematopoietic stem and progenitor cells for hematopoietic reconstitution at any time after birth can not only be applied in the treatment of diseases which are presently known to be curable by allogeneic bone marrow transplantation, but also offers therapeutic potential for a number of additional diseases which presently are not considered likely to benefit from allogeneic marrow transplantation. This is due to the fact that allogeneic marrow transplantation (except for the few patients who are already immunologically incompetent) requires pretransplantation conditioning of the recipient with intensive cytoreduction with irradiation or chemotherapy for the purpose of eliminating the host (recipient) immune system in order to allow the transplanted marrow cells to engraft. This pretransplantation cytoreduction in combination with allogeneic HLA-identical marrow transplantation can result in a number of serious transplantation-induced complications such as life-threatening infections, long-lasting immunodeficiencies, and frequently, graft-versus-host disease.

Disorders that can be treated by infusion of stem cells include but are not limited to five broad categories. First are diseases resulting from a failure or dysfunction of normal blood cell production and maturation (i.e., aplastic anemia and hypoproliferative stem cell disorders). The second group are neoplastic, malignant diseases in the hematopoietic organs (e.g., leukemia and lymphomas). The third group of disorders comprises those of patients with a broad spectrum of malignant solid tumors of non-hematopoietic origin. Stem cell infusion in these patients serves as a bone marrow rescue procedure, which is provided to a patient following otherwise lethal chemotherapy or irradiation of the malignant tumor. The fourth group of diseases consists of autoimmune conditions, where the stem cells serve as a source of replacement of an abnormal immune system. The fifth group of diseases comprises a number of genetic disorders which can be corrected by infusion of hematopoietic stem cells, preferably syngeneic, which prior to transplantation have undergone gene therapy. Particular diseases and disorders which can be treated by hematopoietic reconstitution with neonatal stem and progenitor cells include but are not limited to those listed in Table II, and described infra.

TABLE II

DISEASES OR DISORDERS WHICH CAN BE TREATED BY HEMATOPOIETIC RECONSTITUTION WITH NEONATAL STEM AND PROGENITOR CELLS

I. Diseases resulting from a failure or dysfunction of normal blood cell production and maturation
    hyperproliferative stem cell disorders
    aplastic anemia
        pancytopenia
        agranulocytosis
        thrombocytopenia
        red cell aplasia
        Blackfan-Diamond syndrome
        due to drugs, radiation, or infection
        idiopathic
II. Hematopoietic malignancies
    acute lymphoblastic (lymphocytic) leukemia
    chronic lymphocytic leukemia
    acute myelogenous leukemia
    chronic myelogenous leukemia
    acute malignant myelosclerosis
    multiple myeloma
    polycythemia vera
    agnogenic myelometaplasia
    Waldenstrom's macroglobulinemia
    Hodgkin's lymphoma
    non-Hodgkins's lymphoma
III. Immunosuppression in patients with malignant, solid tumors
    malignant melanoma
    carcinoma of the stomach
    ovarian carcinoma
    breast carcinoma
    small cell lung carcinoma
    retinoblastoma
    testicular carcinoma TABLE II-continued DISEASES OR DISORDERS WHICH CAN BE
TREATED BY HEMATOPOIETIC RECONSTITUTION
WITH NEONATAL STEM AND PROGENITOR CELLS glioblastoma
       rhabdomyosarcoma
       neuroblastoma
       Ewing's sarcoma
       lymphoma
IV. Autoimmune diseases
       rheumatoid arthritis
       diabetes type I
       chronic hepatitis
       multiple sclerosis
       systemic lupus erythematosus
V. Genetic (congenital) disorders
       anemias
           familial aplastic
           Fanconi's syndrome
           Bloom's syndrome
           pure red cell aplasia (PRCA)
           dyskeratosis congenita
           Blackfan-Diamond syndrome
           congenital dyserythropoietic syndromes I–IV
           Chwachmann-Diamond syndrome
           dihydrofolate reductase deficiencies
           formamino transferase deficiency
           Lesch-Nyhan syndrome
           congenital spherocytosis
           congenital elliptocytosis
           congenital stomatocytosis
           congenital Rh null disease
           paroxysmal nocturnal hemoglobinuria
           G6PD (glucose-6-phosphate dehydrogenase) variants 1, 2, 3
           pyruvate kinase deficiency
           congenital erythropoietin sensitivity deficiency
           sickle cell disease and trait
           thalassemia alpha, beta, gamma
           met-hemoglobinemia
       congenital disorders of immunity
           severe combined immunodeficiency disease (SCID)
           bare lymphocyte syndrome
           ionophore-responsive combined immunodeficiency
           combined immunodeficiency with a capping abnormality
           nucleoside phosphorylase deficiency
           granulocyte actin deficiency
           infantile agranulocytosis
           Gaucher's disease
           adenosine deaminase deficiency
           Kostmann's syndrome
           reticular dysgenesis
           congenital leukocyte dysfunction syndromes
VI. Others
       osteopetrosis
       myelosclerosis
       acquired hemolytic anemias
       acquired immunodeficiencies
       infectious disorders causing primary or secondary
       immunodeficiencies
           bacterial infections (e.g., Brucellosis,
               Listerosis, tuberculosis, leprosy)
           parasitic infections (e.g., malaria, Leishmaniasis)
           fungal infections
       disorders involving disproportions in lymphoid cell sets and
         impaired immune functions due to aging
       phagocyte disorders
           Kostmann's agranulocytosis
           chronic granulomatous disease
           Chediak-Higachi syndrome
           neutrophil actin deficiency
           neutrophil membrane GP-180 deficiency
       metabolic storage diseases
           mucopolysaccharidoses
           mucolipidoses
       miscellaneous disorders involving immune mechanisms
       Wiskott-Aldrich Syndrome
       alpha 1-antitrypsin deficiency

5.6.1. Diseases Resulting from a Failure of Dysfunction of Normal Blood Cell Production and Maturation In this embodiment of the invention, reconstitution of the hematopoietic system with neonatal stem and progenitor cells can be used to treat diseases resulting from a failure or dysfunction of normal blood cell production and maturation, i.e., aplastic anemia and hypoproliferative stem cell disorders. These disorders entail failure of stem cells in bone marrow to provide normal numbers of functional blood cells. The aplastic anemias result from the failure of stem cells to give rise to the intermediate and mature forms of red cells, white cells, and platelets. Red cell production is usually most seriously affected, but a marked decrease in production of other mature blood cell elements is also seen. The large majority of these anemias are acquired during adult life, and do not have any apparent genetic predisposition. About half of these acquired anemias arise in the absence of any obvious cau.;ative factor such as exposure to poisons, drugs or disease processes that impair stem cell function; these are termed idiopathic aplastic anemias. The remaining cases are associated with exposure to an extremely diverse array of chemicals and drugs and can also occur as the consequence of viral infections such as hepatitis, and after pregnancy. Other types of aplastic anemia are termed agranulocytosis or thrombocytopenia to indicate that the major deficiency lies in particular white cells or in platelet production, respectively. Agranulocytosis may be associated with autoimmune syndromes such as systemic lupus erythematosis (SLE) or with infections, particularly neonatal rubella.

The overall mortality of all patients with aplastic anemias, in the absence of stem cell therapy, is high. Approximately 60–75% of individuals suffering from the disorder die within 12 months, in the absence of new stem cells. The overall incidence of these diseases is approximately 25 new cases per million persons per year. Although it is extremely unlikely that a single pathogenic mechanism accounts for all aplastic anemias, it is clear that provision of new hematopoietic stem cells is usually sufficient to allow permanent recovery, since transplantation of patients with aplastic anemia with bone marrow obtained from identical twins (i.e., syngeneic) (Pillow, R. P., et al., 1966, N. Engl. J. Med. 275(2):94–97) or from HLA-identical siblings (i.e., allogeneic) (Thomas, E. D., et al., Feb. 5, 1972, The Lancet, pp. 284–289) can fully correct the disease. However, some patients with aplastic anemia reject the transplanted marrow. This complication is particularly common among patients who have been immunologically sensitized as a result of multiple therapeutic blood transfusions. In a preferred embodiment of the invention employing autologous neonatal stem cells for hematopoietic reconstitution, such a complication can be avoided.

In a specific embodiment of the invention, hematopoietic reconstitution by infusion of neonatal stem cells can be used for the treatment of Fanconi's anemia, an autosomal recessive disease exhibited by congenital malformations associated with bone marrow failure. The stem cell defect is associated with chromosomal instability, and increased risk for malignancy. The disease is always fatal in its natural course. This embodiment of the invention is illustrated by way of example in Section 12, infra, which describes the infusion of neonatal blood comprising hematopoietic stem and progenitor cells into a patient with Fanconi's anemia for treatment of the disease. In a preferred aspect of this embodiment, the patient is conditioned before stem cell infusion, by a conditioning regimen which is modified according to cell sensitivity to alkylating agents and to irradiation (see Gluckman, E., et al., 1983, Brit. J. .Haematol. 54:431–440; Gluckman, E., et al., 1984, Seminars in Haematol. 21(1):20–26; Gluckman, E. and Dutreix, J., 1985, The Cancer Bulletin 37(5):238–242; Gluckman, E., et al., 1980, Brit. J. Haematol. 45:557–564; all incorporated by reference herein). For example, cytogenetic analysis can be used to predict cell sensitivity to alkylating agents (Berger, R., et al., 1980, Brit. J. Haematol. 45:565–568). Tests for radiosensitivity have also been described (Gluckman, E. and Dutreix, J., 1985, The Cancer Bulletin 37(5):238–242; Gluckman, E., et al., 1983, Brit. J. Haematol. 54:431–440). In a particular embodiment, a conditioning regimen using cyclophoshamide and thoraco-abdominal irradiation can be employed.

5.6.2. Hematopoietic Malignancies

Hyperproliferative malignant stem cell disorders which can be treated by hematopoietic reconstitution with neonatal stem and progenitor cells include but are not limited to acute lymphocytic leukemia, chronic lymphocytic leukemia, acute and chronic myelogenous leukemia, multiple myelomas, polycythemia vera, agnogenic myelometaplasia, Waldenstrom's macroglobulinemia, and Hodgkins and non-Hodgkins lymphoma. These leukemias are currently treated by chemotherapy and, when feasible, allogeneic bone marrow transplantation. However, allogeneic HLA identical sibling bone marrow is available only to less than one-third of patients, and this treatment is associated with transplantation-related complications such as immunodeficiency and graft versus host disease. Provision of syngeneic (self) cryopreserved hematopoietic stem cells, according to a preferred embodiment of the invention, would permit hematopoietic reconstitution of patients lacking suitable allogeneic donors and eliminate the risks of graft versus host disease arising from allogeneic marrow transplantation.

5.6.3. Malignant, Solid Tumors of Non-Hematopoietic Origin

Hematopoietic reconstitution can greatly aid in the treatment of patients with malignant, solid tumors undergoing irradiation or chemotherapy, by providing new stem cells. Such tumors include but are not limited to those listed in Table II, supra.

There is increasing evidence that a number of cancers are remarkably sensitive to extremely high doses of normally ineffective anti-neoplastic drugs. These cancers include malignant melanoma, carcinomas of the stomach, ovary, and breast, small cell carcinoma of the lung, and malignant tumors of childhood (including retinoblastoma and testicular carcinoma), as well as certain brain tumors, particularly glioblastoma. However, such intensive high dose chemotherapy is not widely used because it frequently causes hematopoietic failure and death. The provision of new stem cells after intensive chemotherapy has been accomplished by using bone marrow cells obtained from patients before administration of the cytotoxic drugs (Spitzer, G., et al., 1980, Cancer 45:3075–3085). This approach has two major difficulties. First, it has not been routinely possible to obtain sufficient numbers of bone marrow cells from chronically ill patients with cancer. In addition, clinicians have been reluctant to use this approach because of the probability that the patient's bone marrow cells are contaminated by small numbers of neoplastic cells. This is particularly true in the hematologic malignancies, but also pertains to most metastatic cancers. The provision of stem cells according to the present invention, obtained at a time of health, before the onset of cancer, can permit the use of potentially curative intensive chemotherapy without the risk of stem cell failure.

5.6.4. Autoimmune Disorders

Many chronic inflammatory and degenerative diseases are characterized by a continuous immune reaction against the body's own tissues. Such autoimmune disorders include but are not limited to rheumatoid arthritis and other inflammatory osteopathies, diabetes type I, chronic hepatitis, multiple sclerosis, and systemic lupus erythematosus.

Autoimmune disorders are often treated by lymphoid irradiation. Use of the neonatal hematopoietic stem and progenitor cells for hematopoietic reconstitution according to the present invention can be extremely valuable after radiotherapy.

Anti-inflammatory drugs such as steroids retard the inflammatory cells which are activated by autoreactive T cells, but do not prevent T cells which recognize self-proteins from activating new inflammatory cells. A more direct approach to treating autoimmune diseases depends on eradication of T cells by irradiation of the lymphoid tissues, and relying on stem cells from the unirradiated bone marrow to repopulate the patient's hematopoietic system. The rationale is that the formation of new populations of mature T cells from bone marrow stem cells may result in absence of T cells that have reactivity to self-specific antigens. This procedure, called total lymphoid irradiation (TLI), has been used to treat intractable rheumatoid arthritis (Strober, S., et al., 1985, Annals of Internal Medicine 102:441–449, 450–458). These clinical trials showed that in the majority of otherwise intractable cases, joint disease was significantly alleviated for at least 2–3 years. However, the major drawback to such treatment is failure of stem cells in the bone marrow of these elderly patients to efficiently repopulate the hematopoietic sytem, resulting in infections and bleeding disorders. Analogous studies have been made of the effects of TLI as an alternative to cytotoxic drugs for treatment of SLE (Strober, S., et al., 1985, Ann. Internal Med. 102:450). Studies of the use of TLI to treat intractable SLE have also shown that this treatment alleviates disease activity, but is severely limited by failure of bone marrow stem cells to rapidly and efficiently repopulate the hematopoietic system after irradiation. In a preferred aspect of the invention, the availability of an individual's own stem cells, obtained at birth, can allow efficient repopulation of mature T cells in an adult environment, after minimal lymphoid radiotherapy, and can thus render this therapy significantly more effective.

5.6.5. Gene Therapy

Hematopoietic reconstitution with the neonatal stem and progenitor cells of the invention which have undergone gene therapy, i.e., which have stably incorporated a heterologous gene capable of expression by their progeny cells, can be of great value in the treatment of diseases and disorders affecting cells of hematopoietic lineage. In one embodiment, hematopoietic reconstitution with such recombinant stem cells can be used in the treatment of genetic disorders of the hematopoietic system. Such genetic disorders include but are not limited to those listed in Table II, supra. Genetic deficiencies or dysfunctions of hematopoietic cells can be treated by supplying, to a patient, recombinant stem and progenitor cells. In a specific embodiment, patients who have hematopoietic cells which lack a gene or have a mutant gene, can be reconstituted with neonatal stem and progenitor cells that have incorporated a functional counterpart of the deficient gene. In particular, such genes which can be subject to gene therapy include but are not limited to hemoglobin or enzymes which mediate its synthetic pathway (e.g., for treatment of anemias such as beta-thalassemia, sickle-cell disease).

In another specific embodiment, patients with infections by pathogenic microorganisms which occur in or affect a hematopoietic cell lineage can be treated with recombinant neonatal stem and progenitor cells. Such recombinant stem and progenitors can contain a heterologous gene which is expressed as a product which ameliorates disease symptoms, is toxic to the pathogen without significant detriment to the host, or interferes with the pathogen's life cycle, etc. Pathogens which cause infections which may be treated with recombinant stem cells according to this embodiment of the invention include but are not limited to lymphotropic viruses such as Human Immunodeficiency Virus (HIV, the etiological agent of acquired immune deficiency symdrome (AIDS)) (Gallo et al., 1984, Science 224:500–503; Barre-Sinoussi, F., et al., 1983, Science 220:868; Levy, J. A., et al., 1984, Science 225:840); gram-negative bacilli such as Brucella or Listeria; the mycobacterium which cause tuberculosis, or which cause Hansen's disease (leprosy); parasites such as Plasmodium (the etiological agents of malaria), or Leishmania; and fungi (such as those that cause pneumonia and other lethal infections secondary to immunodeficiencies) (for a discussion of many of these disorders, see Harrison's Principles of Internal Medicine, 1970, 6th Edition, Wintrobe, M. M., et al., eds., McGraw-Hill, New York, pp. 798–1044). As a particular embodiment, it is possible to construct recombinant neonatal stem or progenitor cells that express a sequence which is "anti-sense" to the nucleic acid of a hematopoietic cell pathogen. Such a sequence, which is complementary to the pathogen's RNA or DNA, can hybridize to and inactivate such RNA or DNA, inhibiting the function or expression of the nucleic acid and disrupting the pathogen's life cycle. As a particular example, recombinant neonatal hematopoietic cells can be used in the treatment of AIDS, a disorder which is caused by HIV, apparently by infection of $T4^+$ lymphocytes (Dagleish et al., 1984, Nature 312:763–766; Klatzmann et al., 1984, Nature 312:767–768). Recombinant neonatal stem and progenitor cells which express an anti-sense nucleic acid that is complementary to a critical region (e.g., the long-terminal repeat or polymerase sequence) of the HIV genome (Wain-Hobson et al., 1985, Cell 40:9–17) can be used for hematopoietic reconstitution for the treatment of AIDS.

Numerous techniques are known in the art for the introduction of foreign genes into cells and may be used to construct the recombinant neonatal hemapoietic stem and progenitor cells for purposes of gene therapy, in accordance with this embodiment of the invention. The technique used should provide for the stable transfer of the heterologous gene sequence to the stem cell, so that the heterologous gene sequence is heritable and expressible by stem cell progeny, and so that the necessary developmental and physiological functions of the recipient cells are not disrupted. Techniques which may be used include but are not limited to chromosome transfer (e.g., cell fusion, chromosome-mediated gene transfer, micro cell-mediated gene transfer), physical methods (e.g., transfection, spheroplast fusion, microinjection, electroporation, liposome carrier), viral vector transfer (e.g., recombinant DNA viruses, recombinant RNA viruses) etc. (described in Cline, M. J., 1985, Pharmac. Ther. 29:69–92, incorporated by reference herein).

5.6.6. Miscellaneous Disorders Involving Immune Mechanisms

Hematopoietic reconstitution with the neonatal hematopoietic stem and progenitor cells of the present invention can be used to treat patients with various miscellaneous disorders involving immune mechanisms. Disorders resulting from inefficient function, lack of function, or dysfunction, of an hematopoietic cell lineage can be alleviated by replacement of the hematopoietic cell progeny with those derived from neonatal stem and progenitor cells of normal function. In a specific embodiment, a hemolytic disorder can be treated (for a discussion of hemolytic disorders, see e.g., 1985, Cecil, Textbook of Medicine, Wyngaarden, J. B. and Smith, L. H., eds., 17th Ed., W. B. Saunders Co., pp. 900–915). Hemolytic disorders acquired during adult life account for the large majority of this form of anemia, and reflect the destruction of red cells by lymphocyte products. Stem cell replacement therapy with the neonatal cells of the invention can provide a new source of red cells, and, in an embodiment employing autologous cells, can replace destructive lymphocytes with newly formed cells which are unlikely to generate an immune response against the recipient's red cells. In another specific embodiment, patients whose immune system is compromised e.g., as a result of irradiation or chemotherapy, can be treated by hematopoietic reconstitution with neonatal hemapoietic stem and progenitor cells (see Section 5.6.3). In yet another embodiment, disorders involving disproportions in lymphoid cell sets and impaired immune functions due to aging can be treated by reconstitution with the neonatal cells of the invention. Genetic disorders of metabolism which result in pathologic accumulations of metabolic products in the marrow (e.g., osteopetrosis, metabolic storage diseases) are also among the many disorders envisioned for treatment.

In addition, immune deficiencies which are the primary or secondary result of infection by pathogenic microorganisms can be treated by hematopoietic reconstitution with the stem cells of the invention. In this embodiment, neonatal stem cells can serve as a source of cells of the hematopoietic cell lineage which are needed by the patient. For example, immune deficiencies caused by microorganisms which are intracellular pathogens of hematopoietic cells, can be treated by the provision of new hematopoietic cells, supplied by infused neonatal stem cells. Microorganisms causing immune deficiencies which may be treated according to this embodiment of the invention include but are not limited to gram-negative bacilli such as Brucella or Listeria, the mycobacterium which are the etiological agents of tuberculosis or of Hansen's disease (leprosy), parasites such as Plasmodium (the etiological agents of malaria) or Leishmania, and fungi (such as those that cause pneumonia and other lethal infections secondary to immunodeficiencies) (for a discussion of many of these disorders, see Harrison's Principles of Internal Medicine, 1970, 6th Edition, Wintrobe, M. M., et al., eds., McGraw-Hill, New York, pp. 798–1044).

5.7 Generation and Use of Hematopoietic Stem and Progenitor Cell Progeny

In another method of the invention, progeny cells of hematopoietic stem and progenitor cells of fetal or neonatal blood can be generated in vitro; the differentiated progeny cells thus generated can be therapeutically useful. For example, in one embodiment of this aspect of the invention, hematopoietic stem cells and/or CFU-GEMM progenitor cells, before or after cryopreservation and thawing, can be induced to differentiate into platelets. Such platelets can be used, for example, for infusion into a patient with thrombocytopenia. In another embodiment, granulocytes can be generated in vitro prior to infusion into a patient. One or more of the hematopoietic progeny cells can be generated in vitro, allowing for the in vitro production of blood components. In a preferred embodiment, the generation of differentiated blood components is accompanied by expansion of the hematopoietic stem and progenitor cell pool, in order to allow for production of a greater quantity of differentiated cells. Various growth factors can be used to promote expansion and/or differentiation of hematopoietic stem and progenitor cells, such as cytokines (growth factors) including but not limited to G-CSF, CSF-1, IL-3, IL-5, tumor necrosis factor-α, and γ-interferon. The blood components which are thus produced have uses which are not limited to therapeutic uses in vivo. For example, such progeny cells can be used in vitro, e.g., for the production and isolation of hematopoietic cell products such as growth factors, antibodies, etc.

6. EXAMPLES

6.1. Collection of Human umbilical Cord and Placental Blood

Neonatal blood was collected from human umbilical cords by gravity drainage and/or by needle aspiration from delivered placentas. Data for the volumes obtained in one series of collections from individual births is shown in FIG. 1, and demonstrates that volumes of 50 ml or more can be obtained. Data from another series of collections is shown in FIG. 2, with the collections from individual births identified by method of collection and delivery type, as either: gravity flow, vaginal delivery; gravity flow, Caesarian section; placental aspiration, vaginal delivery; or placental aspiration, Caesarian section. The data show that the majority of the collections had a total volume of greater than 30 ml although many contained less than 50 ml. In recent collections, we have been able to obtain volumes approximately twice as large as shown in FIG. 2 (e.g., 99 ml blood from a neonate, after a 36 week gestation) by using needle aspirations from the delivered placenta, at the root of the placenta and in the distended surface veins, combined with cord drainage.

Cord blood collections were done essentially as described in Section 5.1.1 and subsections, supra, and as detailed infra.
Cord blood collection kits consisted of:
wide-mouth bottle (200 ml) (Corning, Corning, N.Y.), Cat. No. 25625–200; VWR, South Plainfield, N.J., Cat. No. 28199-756)
wrap (operating room drape sheet)
For collections by needle aspiration, 60 cc syringes B–D Luerlok (VWR, Cat. No. BD5663) and 18 gauge needles 1½ inch (VWR, Cat. No. BD5196) were used.
Collection bottles were sterilized before collection by beta-irradiation with 2.5 megarads from a tungsten source (Dynamatron Accelerator, Radiation Dynamics, Inc., Melville, N.Y.). Syringes and needles were autoclaved. (Alternatively, the syringes and needles were sterilized with ethylene oxide.)
Twenty ml of CPD (citrate-phosphate-dextrose) was added 30 to each cord blood collection container, as an anti-coagulent. CPD was prepared according to the following:

| | |
|---|---|
| Trisodium citrate (dihydrate) | 28.8 g |
| Citric acid (monohydrate) | 3.2 g |
| Sodium dihydrogen phosphate (monohydrate) | 2.19 g |
| Dextrose | 25.0 g |

Bring volume to 1,000 ml; pH should be 5.63. Use at 20 ml CPD per up to approximately 120 ml blood.

In selected samples, acid-citrate-dextrose (ACD) (Hurn, B. A. L., 1968, Storage of Blood, Academic Press, New York, p. 137) was used instead of CPD. ACD was prepared according to the following:

| | |
|---|---|
| Trisodium citrate (dihydrate) | 1.65 g |
| Citric acid (monohydrate) | 1.983 g |
| Dextrose (anhydrous) | 6.13 g |
| in a total volume of 250 ml | |

The substitution of ACD for CPD caused no observable differences in the hematopoietic stem and progenitor cell counts which were obtained.

Penicillin and streptomycin were also added to the collected blood. 0.01×cord blood volume, of a solution consisting of 5000 units penicillin per ml and 500 ug streptomycin per ml, was added to each cord blood sample.

Approximately 109 of the human umbilical cord blood samples which were collected were subjected to further analysis as described infra.

6.2. Hematopoietic Stem and Progenitor Cells in Collected Cord Blood

The approximately 109 collected cord blood samples of section 6.1 were sent by overnight mail (in polystyrene mailers; Fisher, Fairhaven, N.J., Cat. No. 03-528-10) to a processing site where they were separated, counted for viable cell numbers, set up for hematopoietic progenitor cell assays (in most cases), frozen away for storage, and in some cases defrosted for assessment of recovery of total nucleated cells and hematopoietic progenitors (see Section 6.7, infra). The progenitor cells evaluated included immature and mature granulocyte-macrophage (day 7 CFU-GM, day 14 CFU-GM), "immature" and "mature" erythroid (BFU-E-$_1$, BFU-E-2), and multipotential cells (see Section 6.6 and subsections, infra for assays of progenitor cells). Table III presents a complete list of the samples received and the numbers of Hematopoietic progenitor cells per sample present in the low density fraction after separation with Ficoll-Hypaque.

TABLE III

HEMATOPOIETIC PROGENITOR CELLS IN HUMAN CORD BLOOD

| Sample | Total Volume (ml) | Total Nucleated Blood Cells (× 10$^{-6}$) | Viable Low Density Blood Cells (%) | Total Viable Low Density Blood Cells (× 10$^{-6}$) | Total Progenitor Cells (Expressed as Colonies × 10$^{-3}$) | | | | Comments |
|---|---|---|---|---|---|---|---|---|---|
| | | | | | CFU-GM (Day 7) | CFU-GM (Day 14) | BFU-E-2 | BFU-E-1 | CFU-GEMM |
| CB-1 | 72.5 | 631 | 93.4 | 112 | 40 | 159 | 116 | 76 | 90 |
| CB-2 | 67.0 | 2492 | 95.5 | 423 | 364 | 668 | 448 | 456 | 541 |

TABLE III-continued

HEMATOPOIETIC PROGENITOR CELLS IN HUMAN CORD BLOOD

| Sample | Total Volume (ml) | Total Nucleated Blood Cells (× 10$^{-6}$) | Viable Low Density Blood Cells (%) | Total Viable Low Density Blood Cells (× 10$^{-6}$) | CFU-GM (Day 7) | CFU-GM (Day 14) | BFU-E-2 | BFU-E-1 | CFU-GEMM | Comments |
|---|---|---|---|---|---|---|---|---|---|---|
| CB-3 | 63.5 | 699 | 94.3 | 103 | 25 | 119 | 803 | 64 | 72 | |
| CB-4 | | | | Sample leaked - not sterile - not set up | | | | | | |
| CB-5 | 32.0 | 246 | 97.2 | 108 | Sample had leaked, was set up - cultures were contaminated | | | | | |
| CB-6 | | | | Not Received | | | | | | |
| CB-7 | 51.0 | 352 | 96.6 | 107 | 6 | 34 | 2 | 6 | 2 | |
| CB-8 | 37.1 | 197 | 95.6 | 45 | 10 | 20 | 6 | 13 | 14 | |
| CB-9 | 53.4 | 374 | 96.0 | 98 | 10 | 163 | 75 | 85 | 61 | |
| CB-10 | 72.4 | 1138 | 96.5 | 149 | 39 | 298 | 128 | 119 | 113 | |
| CB-11 | 55.6 | 862 | 93.9 | 71 | 1 | 23 | 37 | 34 | 21 | |
| CB-12 | 41.5 | 328 | 1.5 | 1 | Cell viability too low - not set up | | | | | |
| CB-13 | 52.0 | 468 | 2.8 | 4 | " | | | | | |
| CB-14 | 72.8 | 910 | 96.4 | 117 | 59 | 115 | 138 | 122 | 103 | Blood had leaked |
| CB-15 | 68.7 | 1637 | 91.1 | 126 | 25 | 76 | 108 | 86 | 53 | " |
| CB-16 | 40.2 | 302 | 92.7 | 28 | 4 | 8 | 5 | 8 | 6 | " |
| CB-17 | 34.1 | 193 | 93.5 | 26 | 0 | 0 | 4 | 9 | 4 | |
| CB-18 | | | | Sample leaked - Not sterile - not set up | | | | | | |
| CB-19 | | | | " | | | | | | |
| CB-20 | | | | " | | | | | | |
| CB-21 | 43.5 | 283 | 93.1 | 25 | 1 | 4 | 1 | 2.5 | 1 | |
| CB-22 | 55.0 | 1430 | 93.7 | 96 | 10 | 52 | 4 | 40 | 23 | Blood leaked |
| CB-23 | 79.8 | 1373 | 94.3 | 362 | 188 | 507 | 362 | 290 | 275 | |
| CB-24 | 68.0 | 952 | 92.7 | 72 | 7 | 33 | 19 | 39 | 37 | |
| CB-25 | 26.5 | 106 | 21.3 | 0.2 | Cells clumped after Ficoll Separation, assay not set up because of low yield | | | | | |
| CB-26 | 40.2 | 181 | 95.3 | 83 | 12 | 46 | 42 | 51 | 32 | |
| CB-27 | 40.0 | 304 | 90.9 | 21 | 0 | 2 | 1 | 2 | 1 | |
| CB-28 | 38.7 | 375 | 93.5 | 7 | 0 | 0 | 0 | 0 | 0 | |
| CB-29 | 38.3 | 383 | 96.7 | 32 | 3 | 12 | 6 | 6 | 9 | |
| CB-30 | 29.5 | 139 | 96.7 | 3 | 0 | 0 | 0 | 0 | 0 | |
| CB-31 | 46.3 | 597 | 95.0 | 81 | 21 | 96 | 47 | 44 | 47 | |
| CB-32 | 21.4 | 64 | 94.4 | 4 | 0.2 | 0.6 | 1 | 1 | 0.2 | |
| CB-33 | 38.4 | 442 | 95.6 | 86 | 21 | 72 | 72 | 46 | 48 | |
| CB-33 | 41.0 | 426 | 97.6 | 98 | 33 | 90 | 92 | 71 | 49 | |
| CB-34 | 26.6 | 420 | 81.4 | 42 | 18 | 51 | 23 | 23 | 18 | |
| CB-35 | 35.5 | 579 | 95.7 | 61 | 28 | 79 | 39 | 40 | 27 | |
| CB-36 | 56.4 | 812 | 87.9 | 48 | 30 | 74 | 59 | 64 | 39 | |
| CB-37 | 56.0 | 610 | 96.7 | 109 | 52 | 135 | 115 | 129 | 85 | |
| CB-38 | 21.0 | | | 11 | Cells clumped + hemolysis - not set up | | | | | |
| CB-39 | 22.5 | 18 | 97.7 | 2 | 1 | 3 | 2 | 1 | 1 | |
| CB-40 | 56.6 | 849 | 95.6 | 64 | 31 | 60 | 33 | 33 | 9 | |
| CB-41 | 114.0 | 1493 | 96.0 | 375 | 15 | 97 | 157 | 172 | 52 | |
| CB-42 | 86.0 | 2649 | 95.6 | 326 | 0 | 46 | 124 | 85 | 19 | |
| CB-43 | 52.5 | 383 | 73.5 | 24 | 35 | 86 | 49 | 23 | 36 | |
| CB-44 | 13.0 | 39 | 51.5 | 1 | low yield + low viability - not set up | | | | | |
| CB-45 | 14.4 | 37 | 52.6 | 1 | " | | | | | |
| CB-46 | 27.6 | 419 | 96.7 | 48 | 14 | 20 | 33 | 30 | 19 | |
| CB-47 | 31.6 | 436 | 95.4 | 94 | 17 | 19 | 53 | 66 | 21 | |
| CB-48 | 28.7 | 330 | 65.8 | 6 | 10 | 37 | 8 | 7 | 5 | samples, through a mistake, were in transit for 48 hours before receipt |
| CB-49 | 25.6 | 276 | 60.5 | 6.5 | 12 | 38 | 7 | 6 | 5 | |
| CB-50 | 85.0 | 994 | 88.5 | 85 | 59 | 114 | 51 | 65 | 41 | |
| CB-51 | 24.5 | 245 | 92.4 | 51 | 27 | 73 | 35 | 37 | 20 | |
| CB-52 | 23.0 | 262 | 93.2 | 15 | 16 | 47 | 19 | 18 | 13 | |
| CB-53 | 50.5 | 1353 | 95.4 | 320 | 256 | 653 | 506 | 448 | 186 | |
| CB-54 | 67.0 | 791 | 92.2 | 191 | 38 | 130 | 72 | 95 | 50 | |
| CB-55 | 118.4 | 1219 | 86.2 | 223 | 143 | 343 | 107 | 196 | 85 | |
| CB-56 | 49.5 | 807 | 95.6 | 40 | 18 | 49 | 24 | 35 | 17 | |
| CB-57 | 49.4 | 217 | 92.8 | 43 | 16 | 32 | 20 | 17 | 5 | |
| CB-58 | 41.8 | 719 | 95.2 | 139 | 36 | 164 | 100 | 50 | 33 | |
| CB-59 | 34.8 | 602 | 98.1 | 92 | 55 | 121 | 50 | 31 | 11 | |
| CB-60 | 29.5 | 540 | 81.0 | 109 | 35 | 59 | 30 | 76 | 37 | |
| CB-61 | 25.8 | 655 | 90.0 | 68 | 16 | 30 | 31 | 43 | 26 | |
| CB-62 | 29.3 | 735 | 59.5 | 75 | 13 | 52 | 64 | 67 | 43 | |
| CB-63 | 26.3 | 686 | 72.4 | 45 | 3 | 40 | 18 | 18 | 6 | |
| CB-64 | 132 | 2218 | 96.4 | 464 | 56 | 213 | 343 | 306 | 139 | |
| CB-65 | | | | fungal contamination - not set up | | | | | | |
| CB-66 | 102 | 2029 | 81.3 | 349 | 153 | 272 | 237 | 230 | 126 | |
| CB-67 | 78.8 | 843 | 93.3 | 251 | 80 | 120 | 171 | 161 | 105 | |

TABLE III-continued

HEMATOPOIETIC PROGENITOR CELLS IN HUMAN CORD BLOOD

| Sample | Total Volume (ml) | Total Nucleated Blood Cells ($\times 10^{-6}$) | Viable Low Density Blood Cells (%) | Total Viable Low Density Blood Cells ($\times 10^{-6}$) | Total Progenitor Cells (Expressed as Colonies $\times 10^{-3}$) | | | | Comments |
|---|---|---|---|---|---|---|---|---|---|
| | | | | | CFU-GM (Day 7) | CFU-GM (Day 14) | BFU-E-2 | BFU-E-1 | CFU-GEMM |
| CB-68 | 117.5 | 1739 | 71.5 | 265 | 111 | 265 | 223 | 170 | 143 |
| CB-69 | | | | | not received | | | | |
| CB-70 | 40.5 | 251 | 91.2 | 38 | 4 | 5 | 4 | 6 | 2 |
| CB-71 | 40.5 | 713 | 93.3 | 75 | 16 | 21 | 37 | 25 | 15 |
| CB-72 | 43.7 | 717 | 91.6 | 61 | 8 | 17 | 23 | 18 | 5 |
| CB-73 | 61.2 | 1206 | 70.9 | 178 | 50 | 78 | 110 | 78 | 28 |
| CB-74 | 62 | 1376 | 75.1 | 223 | 67 | 134 | 156 | 165 | 89 |
| CB-75 | 60 | 1194 | 73.1 | 174 | 42 | 139 | 111 | 125 | 63 |
| CB-76 | 81.5 | 1002 | 90.2 | 115 | 11 | 106 | 57 | 80 | 16 |
| CB-77 | 130.0 | 3570 | 97.7 | 798 | 287 | 1085 | 527 | 606 | 255 |
| CB-78 | 80.0 | 736 | 93.5 | 66 | Cells frozen away but colony assay not set up | | | | |
| CB-79 | 69.8 | 845 | 84.5 | 100 | | | " | | |
| CB-80 | 52.2 | 767 | 88.4 | 32 | | | " | | |
| CB-81 | 127 | 2032 | 89.6 | 325 | | | " | | |
| CB-82 | 55 | 599 | 84.5 | 13 | Cells frozen away but colony assay not set up | | | | |
| CB-83 | 85.7 | 1465 | 93.8 | 143 | 66 | 357 | 177 | 146 | 120 |
| CB-84 | 45.7 | 334 | 97.4 | 109 | 65 | 89 | 50 | 41 | 30 |
| CB-85 | 60.8 | 1660 | 93.5 | 360 | 209 | 338 | 518 | 418 | 187 |
| CB-86 | 67.2 | 1579 | 92.6 | 650 | 182 | 260 | 351 | 494 | 234 |
| CB-87 | 53.0 | 1420 | 89.8 | 117 | 58 | 117 | 94 | 58 | 42 |
| CB-88 | 80.0 | 968 | 98.2 | 198 | 99 | 340 | 20 | 36 | 4 |
| CB-89 | 66.5 | 818 | 96.5 | 340 | 122 | 231 | 68 | 61 | 14 |
| CB-90 | 33.5 | 188 | 91.5 | 44 | 8 | 17 | 3 | 9 | 0 |
| CB-91 | 87.0 | 1105 | 94.2 | 237 | 19 | 137 | 52 | 43 | 5 |
| CB-92 | 51.0 | 398 | 90.0 | 49 | 31 | 100 | 50 | 61 | 46 |
| CB-93 | 56.2 | 663 | 96.6 | 143 | 54 | 77 | 51 | 69 | 23 |
| CB-94 | 58.2 | 652 | 88.5 | 130 | 60 | 94 | 60 | 78 | 55 |
| CB-95 | 57.7 | 710 | 85.5 | 113 | 41 | 68 | 72 | 50 | 43 |
| CB-96 | 36.5 | 150 | 91.9 | 20 | 4 | 5 | 12 | 10 | 6 |
| CB-97 | 66.2 | 496 | 96.1 | 53 | 8 | 20 | 29 | 27 | 23 |
| CB-98 | 49.0 | 157 | 95.6 | 23 | 1 | 4 | 10 | 10 | 5 |
| CB-99 | 38.5 | 239 | 93.9 | 72 | 7 | 22 | 37 | 39 | 23 |
| CB-100 | 72.0 | 1058 | 95.5 | 294 | Cells frozen away but colony assays not set up | | | | |
| CB-101 | 28.0 | 134 | 96.1 | 33 | | | " | | |
| CB-102 | 61.3 | 760 | 70.1 | 203 | | | " | | |
| CB-103 | 33.9 | 193 | 80.7 | 6 | | | " | | |
| CB-104 | 96.5 | 1911 | 87.2 | 283 | | | " | | |
| CB-105 | 54.0 | 1620 | 91.4 | 159 | | | " | | |
| CB-106 | 78.0 | 3838 | 92.0 | 204 | | | " | | |
| CB-107 | 64.2 | 1669 | 89.2 | 198 | | | " | | |
| CB-108 | 39.0 | 214 | 54.2 | 12 | | | " | | |
| CB-109 | 49.3 | 458 | 93.6 | 49 | | | " | | |
| CB-110 | 57.5 | 724 | 92.2 | 147 | | | " | | |
| CB-111 | 52.0 | 502 | 92.1 | 56 | 8 | 46 | 25 | 36 | 30 |

From receipt of the samples until the cells were frozen, 16 hours were spent in processing the cells. (This time period included cell separation on Ficoll-Hypaque, counting the cells, setting up the progenitor cell assays, and freezing the cells).

As shown in Table III, significant total numbers of progenitors cells were obtained even with the overnight transit time plus 16 hour processing. Even among the samples in transit for 48 hours, viable progenitor cells were observed. There was variability among donors in the observed number of progenitor cells. It should be noted that the values shown in Table III represent remaining progenitor cells after loss of progenitors due to cell separation procedures (see Table IV, infra).

6.3. Enrichment for Human Hematopoietic Stem and Progenitor Cells: Cell Separation Procedures In a preferred embodiment of the invention, whole neonatal blood can be cryogenically preserved, and used for hematopoietic reconstitution after thawing, in order to avoid cell losses associated with cell separation procedures. However, it is envisioned that cell separation procedures can be used if desired, e.g., to minimize blood storage volumes. Thus, in the examples sections herein, cell separation procedures are described which can be used to enrich for neonatal hematopoietic stem cells in collected blood. Many of the procedures relate to the enrichment of stem cells derived from adult bone marrow or adult blood, however, it is envisioned that the same procedures, or modifications there-of, are equally applicable to the neonatal hematopoietic stem cells of the present invention.

Human stem and progenitor cells are present in the non-adherent, low density, T-lymphocyte-depleted fraction of bone marrow, spleen, and (adult and cord) blood cells. Purification or enrichment for the stem and progenitor cells has been carried out by Ficoll-Hypaque density separation, adherence/non-adherence separation, and positive selection by antibody binding.

6.3.1. Density Separations

Enrichment for human hematopoietic stem and progenitor cells has been carried out by isolation of low density (density less than 1.077 gm/cm$^3$) cells separated by Ficoll-Hypaque (Pharmacia Fine Chemicals, Piscataway, N.J.).

The following protocol is used for samples of bone marrow or peripheral blood:

1. Obtain sample of bone marrow or peripheral blood.
   Bone Marrow—sample should be 1–5 ml containing heparin. Place in sterile 17×100 mm tube. Add 2–3 ml of sterile DPBS (phosphate-buffered saline without magnesium or calcium). Mix well.
   Whole Blood—Dilute sample at least 1:1 with McCoy's 5A medium or DPBS. Adjust volume to a multiple of 20 ml.
2. Bone Marrow—spin for 10 minutes at approximately 400×g (1500 rpm; Beckman TJ-6R rotor) at 4° C.
   Whole Blood—Go to next step.
3. Bone Marrow—Remove buffy coat and wash once with DPBS. Resuspend to a final volume of 20–40 ml (if 1–2 pulls of 2 ml each, resuspend to 20 ml; if 3–5 pulls, resuspend to 40 ml). Count cells; adjust volume to a maximum of 6×10$^7$ cells per 20 ml.
   Whole Blood—Go to next step.
4. Bone Marrow—With a 10 ml pipet, carefully layer 20 ml of buffy coat suspension onto 15 ml of Ficoll-Hypaque in a 50 ml polypropylene tube.
   Whole Blood—With a 10 ml pipet, carefully layer 20 ml of blood suspension onto 15 ml Ficoll-Hypaque in a 50 ml polypropylene tube.
5. Using a balance, carefully adjust weight of tube(s) with lank(s).
6. With slow acceleration, centrifuge sample(s) at 400×g (1500 rpm) for 30 minutes at 4° C. Turn brake off.
7. Carefully remove the low density band and place it in a lean sterile tube. Dilute at least 1:10 with McCoy's 5A medium or DPBS.
8. Wash cells twice by centrifugation at 400×g for 10 minutes at 40° C. Resuspend to 50 ml and repeat.
9. Final resuspension should be to 10–15 ml with McCoy's media.
10. Perform cell count.

The following modification of the above procedure has been used for cord blood separations (and was used in obtaining the data shown in Tables III and IV):

1. Obtain cord blood, aseptically, using a 60 cc syringe containing 3000–4000 units of preservative-free sodium heparin or ACD as an anticoagulant.
2. Perform low density cell separation using Ficoll-Hypaque density gradient, by diluting cord blood with sterile DPBS (phosphate buffered saline without Mg$^{++}$, Ca$^{++}$), pH 7.0, at a ratio of 1:3 (cord blood: PBS). Layer 20 ml of blood suspension on 15 ml of Ficoll-Hypaque in a 50 ml polypropylene centrifuge tube (FIG. 3). Centrifuge at 4° C., 400×g, for 30 minutes.
3. Collect and pool all low density cell bands (FIG. 4) from each individual donor. Make sure that very little Ficoll-Hypaque is collected with cells, or the cells may not pellet through the collected Ficoll. Dilute the cell suspensions 1:1; if "X" ml of cells were collected, dilute with "X" ml of DPBS in order to dilute collected Ficoll sufficiently to allow cells to pellet. Pellet cells by centrifugation at 4° C., 200×g, for 10 minutes.
4. Aspirate and discard supernatant from each pellet. If several tubes were used, pool identical donor pellets after resuspending each pellet with 5 ml of DPBS. Pellet cells by centrifugation at 4° C., 200×g, for 10 minutes.
5. Aspirate and discard supernatant. Resuspend pellet in 10 ml of DPBS using a 10 ml pipet and gentle up-down aspirations. Bring volume to 50 ml with DPBS. Pellet cells by centrifugation at 4° C., 200×g for 10 minutes.
6. Resuspend in RPMI-1640 medium supplemented with 5% autologous plasma or heat-inactivated fetal calf serum (FCS). Perform cell counts and viability. Keep cell suspension chilled to 4° C.

The effect of various density separation procedures on the yield of progenitor cells in the human cord blood collected (described in Section 6.1, supra) was assessed. We have compared the number of progenitors in whole blood, no separation treatment, to that of whole blood in which the mature erythrocytes were lysed by treatment with ammonium chloride (NH$_4$Cl), low density cells after Ficoll-Hypaque separation (density less than 1.077 gm/cm$^3$), heavy density cells after Ficoll-Hypaque separation, and heavy density cells after treatment with NH$_4$Cl to lyse the erythrocytes (Table IV, Exp. 1).

TABLE IV

COMPARISON OF HEMATOPOIETIC PROGENITOR CELLS OBTAINED WITH DIFFERENT CELL SEPARATION PROCEDURES

| | Progenitor Cells × 10$^{-3}$ | | | | |
|---|---|---|---|---|---|
| Separation Procedure | CFU-GM day 7 | CFU-GM day 14 | BFU-E-2 | BFU-E-1 | CFU-GEMM |
| Exp #1 | | | | | |
| None (Whole Blood) | 167 | 220 | 330 | 356 | 356 |
| Whole Blood + NH$_4$Cl | 55 | 112 | 43 | 39 | 43 |
| Low Density (Ficoll) | 35 | 87 | 49 | 23 | 36 |
| Heavy Density (Ficoll) | 49 | 104 | 71 | 82 | 153 |
| Heavy Density + NH$_4$Cl | 17 | 40 | 17 | 14 | 11 |
| Exp #2 | | | | | |
| None (Whole Blood) | 561 | 1020 | 612 | 484 | 408 |
| Whole Blood Sedimented with Methyl Cellulose | 157 | 388 | 212 | 286 | 111 |
| Low Density (Ficoll) | 256 | 653 | 506 | 448 | 186 |
| Heavy Density (Ficoll) | 3 | 8 | 8 | 14 | 5 |

TABLE IV-continued

COMPARISON OF HEMATOPOIETIC PROGENITOR CELLS OBTAINED WITH DIFFERENT CELL SEPARATION PROCEDURES

| | Progenitor Cells × $10^{-3}$ | | | | |
|---|---|---|---|---|---|
| Separation Procedure | CFU-GM day 7 | CFU-GM day 14 | BFU-E-2 | BFU-E-1 | CFU-GEMM |
| Exp #3 | | | | | |
| SampleCB-57 | | | | | |
| Whole Blood Sedimented with Methyl Cellulose | 6 | 12 | 11 | 12 | 6 |
| Low Density (Ficoll) | 35 | 59 | 30 | 76 | 37 |
| SampleCB-58 | | | | | |
| Whole Blood Sedimented with Methyl Cellulose | 5 | 14 | 14 | 17 | 7 |
| Low Density (Ficoll) | 16 | 30 | 31 | 43 | 26 |
| SampleCB-59 | | | | | |
| Whole Blood Sedimented with Methyl Cellulose | 6 | 21 | 31 | 39 | 17 |
| Low Density (Ficoll) | 13 | 52 | 64 | 67 | 43 |
| SampleCB-60 | | | | | |
| Whole Blood Sedimented with Methyl Cellulose | 2 | 9 | 5 | 4 | 0.4 |
| Low Density (Ficoll) | 3 | 40 | 18 | 18 | 6 |

As shown in Table IV, Exp. 1, there are many more progenitors detected in the unseparated blood than in the low density Ficoll preparation. This difference is not due to loss of cells into the dense fraction of Ficoll, which contains mainly mature neutrophilic granulocytes. Lysing whole blood erythrocytes also resulted in a lower yield of progenitors. In experiment number 2, we compared whole blood, whole blood that was sedimented with methyl cellulose to remove erythrocytes, and low and high density Ficoll separated cells. The results demonstrated that whole blood contained the most progenitors, some of which were lost from the fraction of cells obtained after sedimentation of the erythrocytes with methyl cellulose. As seen in both experiments 2 and 3 of Table IV, sedimenting cells with methyl cellulose was inferior to the low density fraction of Ficoll with respect to numbers of progenitors. While the Ficoll separation removed mature granulocytes and erythrocytes from the progenitor cell fraction, some progenitors were also lost, relative to whole blood, using this procedure.

6.3.2. Adherence/Non-Adherence Separation

An adherence/non-adherence separation protocol for enrichment of hematopoietic stem and progenitor cells is as follows:

1. In a 60 mm Corning tissue culture dish, seed 10–15×$10^6$ low density cells in up to 3 ml of McCoy's 5A (supplemented) media with 10% fetal calf serum (heat-inactivated).
2. Incubate for 1.5 hours at 37° C. in an atmosphere of 5% $CO_2$.
3. Gently swirl plate to loosen non-adherent cells. Pipet into sterile centrifuge tube. Carefully rinse dish with 3 ml McCoy's media and pool the media.
4. Add 1 ml McCoy's media to the dish, and gently remove the cells with a sterile rubber policeman. Remove the cells and place them in a sterile centrifuge tube. Rinse the dish with 3 ml media and pool media.
5. Pellet cells by centrifugation at 400×g for 10 minutes at 4° C. Aspirate the supernatant and resuspend the cells in media.
6. Repeat step 5.
7. Perform cell count.

6.4. Cryopreservation of Cord Blood Stem and Progenitor Cells

The following protocol has been used for cryopreservation of viable hematopoietic stem and progenitor cells derived from human cord and placental blood:

1. Pellet low density, Ficoll-separated cells by centrifugation at 4° C., 200×g for 10 minutes.
2. Check viable cell count by trypan blue exclusion (Kuchler, R. J., 1977, Biochemical Methods in Cell Culture and Virology, Dowden, Hutchinson & Ross, Stroudsburg, Pa., pp. 18–19) and manual cell counting using a hemocytometer.
3. Gently resuspend cells to a concentration of 4×$10^6$ viable cells/ml, using a mixture of cold (4° C.) 50% autologous plasma/RPMI-1640 or 50% heat-inactivated FCS/RPMI, and place the suspension on ice.
4. In a cryovial containing 1 ml of a chilled, sterile cryoprotective medium of 20% DMSO/RPMI-1640, carefully layer a 1 ml portion of the aforementioned cell suspension on top of the cryoprotective medium.
5. Approximately 10 minutes prior to freezing, slowly invert the 1:1 mixture to promote mixing, then place it on ice to allow equilibrium between the cells and the cryoprotective medium. NOTE: The "layered" tube should not remain unfrozen for very,long, so freezing should preferably be done within 20–30 minutes after exposure of cells to DMSO/RPMI solution.
6. Place the vials in a freezing rack, which in turn is placed in a 4° C. methanol bath, just deep enough to cover the cell suspension (FIG. 4). This is then placed in the bottom (to ensure proper temperature) of a −80° C. freezer for at least 2 hours and less than 24 hours.
7. After cells reach the frozen state, carefully and quickly transfer them to a long term liquid nitrogen containment vessel. A cryogenic storage vessel which can be used is the LR1000 refrigerator (Union Carbide Corp., Indianapolis, Ind.) which accommodates up to 40,000 cryules.

6.5. Cell Thawing

The following protocol has been used for thawing of cryopreserved cord blood stem and progenitor cells:

1. Remove vial of frozen cells from liquid nitrogen. Immediately thaw cell suspension by gently agitating the vial in a 37° C. water bath until just a small amount of ice remains.
2. Aseptically, begin to add drop-wise, a chilled mixture of 50% autologous serum/RPMI-1640 medium or 50% FCS/RPMI-1640 medium with a slight mixing between each drop, until the suspension volume is doubled.
3. Transfer this suspension to a larger centrifuge tube (12–15 ml) and continue to add, drop-wise, 50% serum/RPMI mixture with mixing between every other drop until the volume reaches 6–7 ml. Diluent may now be added, drop-wise, with mixing at every 0.5 ml increment until the volume reaches 9–10 ml. (NOTE: The reason for stepwise addition of diluent is to prevent osmotic shock to the cells as DMSO is diluted in the cell suspension.)
4. Pellet cells by centrifugation at 4° C., 200×g, for 10 minutes. Aspirate the supernatant.
5. Slowly add, drop-wise, 1 ml of chilled 20% autologous serum/RPMI-1640 mixture to the pellet. "Resuspend" the pellet by gently "flicking" the tube with a finger. After the pellet is resuspended (clumps may remain), resuspend it further by gently aspirating up and down with a 1 ml pipet.
6. Add an additional 4 ml chilled 20% autologous serum/RPMI, dropwise, with mixing between every drop; then add 0.5 ml as volume increases, as previously described.
7. Pellet cells by centrifugation at 4° C., 200×g, for 10 minutes. Aspirate the supernatant.
8. Resuspend with 2–5 ml of chilled 20% serum/RPMI mixture.
9. Perform cell counts (by use of a hemocytometer) and viability testing (by trypan blue exclusion).

Loss of cells due to clumping during the stepwise removal of DMSO can be diminished by including DNase (20 U per $2 \times 10^6$ cells) or low molecular weight dextran and citrate (to reduce the pH to 6.5).

6.6. Human Hematopoietic Stem and Progenitor Cell Assays

Assays which can be used to quantitatively assess human hematopoietic stem and progenitor cells are described in the following examples sections. The assays for granulocyte-macrophage (CFU-GM), erythroid (BFU-E), and multipotential (CFU-GEMM) progenitor cells (Sections 6.6.1 and 6.6.2) were used to derive part of the data for human cord blood cells that is presented in Table III, supra.

6.6.1. CFU-GM Assay

The following assay has been used to quantify CFU-GM:
1. Obtain a suspension of cells (cord blood, bone marrow, spleen, cell line, etc.) at a known cell concentration. The cell suspension concentration should be at least 10 fold greater than the final concentration desired in the plate.
2. Depending on the number of plates to be plated, the volume of the culture mixture will vary. As an example, a 10 ml suspension can be made, as described:

In a 17×10 mm polystyrene tube, combine the following components except for the Agar (0.6%) and cells.*

|  | 10 ml |
|---|---|
| Agar (0.6% w/v) (bacto-agar, Difco Corp.) | 5 ml (50%) |
| **2X McCoys 5A | 2 ml (20%) |
| FCS (heat inactivated) | 1 ml (10%) |
| ***Stimulator | 1 ml (10%) |
| *Cells | 1 ml (10%) |

*The cells are added just before adding the melted Agar, in order to avoid allowing the cells to sit in 2X McCoys for very long. Since the Agar has been boiled, care should be taken to allow it to cool sufficiently.
**This volume may vary if the cells are more concentrated than desired. Example: if cells were to be plated at a <u>final</u> cell concentration of $1 \times 10^5$ cells/ml, and the stock cell suspension was $5 \times 10^5$ cells/ml instead of $1 \times 10^6$ cells/ml, 0.2 ml cells would be used, plus 0.8 ml Of 2x McCoys to achieve a 1 ml volume. In general, whatever volume is lacking after adding the other components, is made up with 2x McCoy's. (See Section 6.6.1.1, infra for the preparation of McCoy's medium).
***Colony formation can be stimulated by factors present in medium conditioned by the 5637 urinary bladder carcinoma cell line (see Section 6.6.1.2 infra), which was used routinely, or medium conditioned by the PHAL cell line (phytohemagglutinin-stimulated leukocytes from patients with hemochromatosis; Lu, L. and Broxmeyer, H. E., 1985, Exp. Hematol. 13:989–993), or by purified growth factors. Growth factors which may be tested for human colony stimulation include but are not limited to interleukin-3 (IL-3), granulocyte-macrophage (GM)-colony stimulating factor (CSF), granulocyte (G)-CSF, macrophage (M)-CSF (also referred to as CSF-1), erythropoietin, IL-1, IL-4 (also called B-cell growth factor) and E-type prostaglandins. (These molecules are available in purified form from various companies, e.g., Cetus, Immunex, and Amgen.) For murine cell assays, pokeweed mitogen spleen cell conditioned media may be used (see Section 6.6.1.3, infra).

3. After the Agar has sufficiently cooled, add the appropriate volume of cells and 0.6% Agar.
4. Place a cap on the tube, and mix the suspension well. A vortex may be used, but with caution.
5. With an appropriate pipet, place 1 ml of the culture suspension into a 10×35 mm dish, containing colony stimulating factors if so desired. After all the dishes have been plated, allow them to solidify.
6. Label the tray of plates and place it in the appropriate incubator. Incubation is conducted in a humidified atmosphere of 5% $CO_2$ at low oxygen tension (5% 02) for 7 days and 14 days. Low oxygen tension enhances the detection of CFU-GM, BFU-E, and CFU-GEMM cells.
7. Remove plates from the incubator and score by observation of colonies under an inverted or stereoscopic microscope. Colonies scored at 7 and 14 days represent maturation stages of CFU-GM cells. (Day 7 CFU-GM represent a later or more mature progenitor of the granulocyte-macrophage lineage, while day 14 CFU-GM represent an earlier progenitor of the granulocyte-macrophage lineage).

6.6.1.1. Preparation of McCoy's 5A Medium

The following procedure was used to prepare 1×X McCoy's 5A Medium:
1. 1 envelope McCoy's 5A medium (Gibco #430–1500) $NaHCO_3$ 2.2 gm Bring to 1 liter with double-distilled $H_2O$; pH to 7.0–7.2.
2. Filter-sterilize by use of a 0.2 um filter and peristaltic pump (positive pressure).
3. If medium is to be used for growth or incubation, it is supplemented with the following:

| Per Liter of Media | |
| --- | --- |
| 8 ml | MEM essential amino acids (Gibco #320-1130) |
| 4 ml | MEM non-essential amino acids (Gibco #32-1140) |
| 10 ml | MEM sodium pyruvate (Gibco #320-1360) |
| 4 ml | MEM Vitamins (Gibco #320-1120) |
| 10 ml | Penicillin-Streptomycin (Gibco #600-5140) |
| 15 ml | Serine/Asparagine/Glutamine mixture (see recipe infra) |

To prepare 2×McCoy's 5A medium (for plating), follow the same procedure as for 1×, except bring the volume only to 500 ml instead of 1 liter. Add the same volume of supplements.

The Serine/Asparagine/Glutamine mixture is prepared according to the following:

| | |
| --- | --- |
| L-asparagine (Sigma #A-0884) | 800 mg |
| L-serine (Sigma #S-4500) | 420 mg |
| L-glutamine (Gibco #320-5030) | 200 ml |

1. Dissolve serine and asparagine in 450 ml double-distilled $H_2O$), bring the volume to 500 ml and filter-sterilize through a 0.2 um filter
2. Add to this sterile mixture 200 ml of L-glutamine. Mix well and aliquot into 7.5 ml/tube. Store at −20° C.

6.6.1.2. Preparation of Human 5637 Urinary Bladder Carcinoma Cell Line Conditioned Medium The following procedure can be used to obtain medium conditioned by the human 5637 urinary bladder carcinoma cell line:
1. Thaw and start cells from frozen stocks, per "Quick Thaw" protocol of Section 6.5, supra. Grow 5637 cells to confluence in a 150 $cm^2$ flask containing 50 ml of the following medium:
   RPMI 1640
   glutamine (2 mM)
   penicillin-streptomycin (10 ml/liter at 1000 units/ml)
   10% fetal bovine serum (heat-inactivated)
2. Incubate in an atmosphere of 5% $CO_2$, with normal $O_2$, for 3–5 days; check daily.
3. Split the cells 1:20 into 20×150 $cm^2$ flasks with 50 ml RPMI 1640 media (as above).
4. Incubate for 7 days in 5% $CO_2$, normal $O_2$.
5. At 3–5 days, if desired, select 1 flask of cells to prepare for freezing as a stock supply of cells. Freeze $10^6$ cells/vial (1 ml) for liquid nitrogen storage, per the protocol described in Section 6.4, supra.
6. At 7 days, collect cell medium into 20×50 cc centrifuge tubes. Spin down cells and cell debris by centrifugation for 10 minutes at greater than or equal to 500×g.
7. Pool the medium, filter-sterilize it using a 0.2 um filter, and aliquot into 100 ml bottles. Store frozen at less than 0° C. (usually −20° C. or −80° C.).
8. Assay stimulation activity of the medium by the CFU-GM assay described in Section 6.6.1, e.g., using human marrow cells.

6.6.1.3. Preparation of Murine Pokeweed Mitogen Spleen Cell Conditioned Medium

The following procedure can be used to obtain murine pokeweed mitogen spleen cell conditioned medium (PWMSCM), a crude source of growth factors for use in hematopoietic colony stimulation for mouse cells.

1. Obtain a single cell suspension of CBA/J mouse spleen cells at a known cell concentration of greater than or equal to $20 \times 10^6$ cells/ml. (Mice should be 5–7 weeks old).
2. Make a large volume of cell growth suspension as follows:

| | |
| --- | --- |
| CBA/J spleen cells | $2 \times 10^6$ cells/ml |
| Heat-inactivated FCS | 10% |
| Pokeweed mitogen (Gibco #670-5360) | 0.333% (1:300) |
| Iscove's modified Dulbecco's media* + 3.024 gm $NaHCO_3$ (Gibco #78-5220) | Remainder |

*Preparation described infra in Section 6.6.2.3.

3. After mixing the above ingredients, place 50 ml of the mixture in a 50 $cm^2$ tissue culture flask, and incubate for 7 days at 37° C. in an atmosphere of 5% $CO_2$.
4. After seven days, collect the conditioned media and remove the cells by centrifugation at greater than or equal to 500×g at 4° C. for 10–15 minutes.
5. Carefully remove the conditioned media from the tubes, and filter-sterilize the media by passage through a 0.45 um filter. Store the conditioned media in 50 ml polyethylene tubes at −20° C.

6.6.2. BFU-E-2 and BFU-E-1/CFU-GEMM Assay

The following assays have been used to quantify BFU-E-2 and BFU-E-1/CFU-GEMM. BFU-E-1 and BFU-E-2 are erythroid progenitor cells that are operationally defined, and are not proven to be physiologically distinct. The BFU-E-1 is operationally defined as an early erythroid progenitor cell capable of producing a colony of erythroid progeny cells in semi-solid medium, upon stiumlation by erythropoietin, hemin (optional), and a burst-promoting factor. The BFU-E-2 is operationally defined as a more mature erythroid progenitor cell, capable of producing a colony of erythroid progeny cells in semi-solid medium, upon stimulation by erythropoietin and by hemin (optional). BFU-E-1 colonies tend to be larger than BFU-E-2 colonies.

For the BFU-E/CFU-GEMM assay, Iscove's modified Dulbecco's medium (IMDM) was used, with methyl cellulose as the semi-solid support medium. (This was in contrast to the CFU-GM assay, where McCoy's medium was used, with bacto-agar as the semi-solid support medium.)

The procedure was the following:
1. Obtain a single cell suspension of known concentration of the appropriate type of cells.
2. Depending on the number of plates plated, the volume of the culture mixtures will vary. As an example, we will make a 3 ml mixture. In order to increase the mixture volume, simply increase component volumes proportionately. In a 17×100 mm tube, mix the following components:

| | 3 ml |
| --- | --- |
| Methyl cellulose (2.1%) | 1.4 ml |
| Glutamine (200 mM, Gibco) | 30 ul (2 mM) |
| 2-mercaptoethanol ($10^{-2}$ M) (7 ul into 10 ml McCoy's 5A) | 10 ul ($5 \times 10^{-5}$ M) |
| *Hemin (4 mM) | 75 ul (0.1 mM) |
| **Erythropoietin (20 units/ml) | 0.15 ml (1 unit/ml) |
| FCS (not heat-inactivated) | 0.9 ml (30%) |
| Cells (at least 10 X desired) | 0.3 ml |

|  |  |
|---|---|
| ***Iscove's Modified Dulbecco's Medium (IDMD) | 3 ml |
| | 0.135 ml |
| ***GM Stimulator (if desired) | 0.01 ml |

*Preparation described infra; Lu, L. and Broxmeyer, H. E., 1983, Exp. Hematol. 11(8):721–729.
**Note that there are different types of erythropoietin which can be used; as an example, Hyclone erythropoietin has been used in murine cell assays, and Toyobo erythropoietin has been used in human cell assays. Purified recombinant erythropoietin is commercially available (e.g., Amgen, Thousand Oaks, CA) and may be used.
***GM stimulators include but are not limited to various factors which can be tested for colony stimulation, as described for the CFU-GM assay. The volume of the GM stimulator, and thus of the IMDM, may vary with the type of stimulator used (e.g., mouse = PWMSCM; Human = 5637 CM or PHALCM). Also note that IMDM is strictly a compensation for the remaining volume of 3 ml.

3. Mix suspension thoroughly by vortexing and inversion of tubes.
4. After allowing bubbles to rise from the mixture, place 1 ml mixture in each of two 10×35 mm culture plates containing erythropoietin, hemin, and colony stimulating factors, if so desired. Rotate the plates so that the mixture coats the surface of the plates.
5. Place these 2 plates in a large 15×100 mm petri dish along with a 10×35 mm humidifying dish containing about 1 ml of $H_2O$. Replace the lid of the large dish.
6. Place the petri dish in an appropriate incubator for 14 days. Conditions of incubation are the same as described for the CFU-GM assay of Section 6.6.1.
7. Remove plates from the incubator and score by observation of colonies under an inverted or stereoscopic microscope.

In some cultures, the GM stimulator/burst-promoting activity (e.g., medium conditioned by 5637 cells or PHALCM) can be omitted; under these conditions, the assay detects a more mature population of BFU-E (BFU-E-2) cells and few or no CFU-GEMM cells.

6.6.2.1. Preparation of 2.1% Methyl Cellulose

The 2.1% methylcellulose, for use in the BFU-E/CFU-GEMM assay, was prepared as follows:

| Stock solution: | |
|---|---|
| 2.1% Methocel (Dow Chemical Co.) | 21 grams |
| Boiling water | 500 ml |
| 2x IMDM | 500 ml |

Procedure:

The gram weight of methyl cellulose is put into a sterile 3 liter Erlenmeyer flask (having a sterile stopper) containing a sterile magnetic flea on a large magnetic stirrer. To prevent as little frothing as possible, stirring is initiated while 500 ml of sterile boiling distilled $H_2O$ is gently poured down the sides of the flask. Stirring continues at room temperature until the flask gradually cools (this may take an hour). When the flask is no longer hot to the touch, 500 ml of 2×IMDM, which had been allowed to come to room temperature, is added to the flask without frothing. The flask is stoppered and transferred to the cold room (4° C.) where stirring continues for 48 hours. The solution is then sterilely aliquoted into sterile 100 ml bottles. The bottles are stored frozen for up to 6 months (protected from light).

6.6.2.2. Preparation of Hemin

The hemin, for use in the BFU-E/CFU-GEMM assay, was prepared as follows:

| | |
|---|---|
| 260 mg | Hemin (Eastinan Kodak #2203) |
| 4 ml | 0.5 M NaOH |
| 5 ml | Tris buffer, 1 M, pH 7.8 (approximately 9.5 parts acid to 3 parts base) |

Bring to 100 ml with double-distilled $H_2O$.

1. Dissolve hemin in NaOH completely before adding Tris buffer and $H_2O$.
2. After adjusting the volume to 100 ml, filter-sterilize by passage through an 0.45 um filter, and store in 2–3 ml aliquots at −20° C.

6.6.2.3. Preparation of Iscove's Modified Dulbecco's Medium

1×Iscove's Modified Dulbecco's Medium (IMDM), for use in the BFU-E/CFU-GEMM assay, was prepared as follows:

1. Measure out 5% less water (deionized, distilled) than desired total volume of medium, using a mixing container that is as close to the final volume as possible.
2. Add powder medium (Gibco Laboratories, Formula No. 78-5220), to water with gentle stirring at room temperature (do not heat water).
3. Rinse out the inside of the package, to remove all traces of the powder.
4. Add 3.024 grams of $NaHCO_3$ per liter of medium.
5. Dilute to the desired volume with water. Stir until dissolved.
6. Do not adjust pH. Keep container closed until medium is filtered.
7. Sterilize immediately by Nalgene filtration.

To prepare 1 liter of 2× liquid medium, follow the above procedure, except use 2 envelopes of powder instead of one, and 6.048 gm $NaHCO_3$.

6.6.3. Stem Cell Colony Forming Unit Assay

The assay used for stem cell (S-cell) quantitation does not directly assay self-renewal, but instead assays for the ability to generate secondary multilineage colonies on replating. This assay is done essentially the same as the BFU-E/CFU-GEMM assays, except that cultures are scored after 21–28 days of incubation rather than after 14 days (for BFU-E and CFU-GEMM). The drug 4-hydroperoxycyclo-phosphamide (4HC) appears to spare immature progenitors at the expense of mature progenitors, and may be useful for pretreating cells before assay. Factors which can be tested for increasing the self-renewal ability of S-cells in vitro (thus increasing assay efficiency) include but are not limited to hemin, oxygen tension (Smith, S. and Broxmeyer, H. E., 1986, Brit. J. Haematol. 63:29–34), superoxide dismutase, glucose oxidase, IL-3, GM-CSF, G-CSF, M-CSF, erythropoietin, IL-1, IL-4, etc.

6.6.4. Assay of the Proliferative Status of Stem and Progenitor Cells

The proliferative status of stem and progenitor cells can be measured by a high specific activity tritiated thymidine ($^3$HTdr) kill (or suicide) technique, carried out as follows:

1. In two small 12×75 mm polystyrene tubes, place the appropriate volume of stock cell suspension containing 2–3 times the number of cells required for plating. (For bone marrow, 2–3×10$^6$ cells and for spleen, 15–20×10$^6$ cells. For cord blood: 2–3×10$^6$ (approx.) cells.) Label them a and b.
2. Pellet the cells by centrifugation at 200–400×g at 4° C. for 10 minutes.

3. Carefully remove and discard the supernatant.
4. Add 0.5 ml of McCoy's 5A medium supplemented as prescribed in Section 6.6.1.1, supra, and with FCS at 10% v/v.
5. To tube b, add 50 uCi of $^3$HTdr (New England Nuclear, #NET-027X Thymidine, [methyl-$^3$H]-20.0 Ci/mmol; 5.0 mCi/5.0 ml $H_2O$). As a control, to tube a, add 50 ul of McCoy's 5A medium.
6. Place cap back on tubes and gently vortex in order to resuspend cells.

6.7. Recovery After Freeze-Thawing of Human Hematopoietic Progenitor Cells Derived from Cord Blood The results of progenitor cell assays after freeze-thawing were compared to results of the same assays obtained before freeze-thawing, in order to assess the recovery of hematopoietic progenitor cells from human cord blood after the freeze-thawing process. Eight cord blood samples, obtained as described in Section 6.1, supra, and separated by use of Ficoll-Hypaque, were analyzed. The results are shown in Table V.

TABLE V

RECOVERY OF CORD BLOOD HEMATOPOIETIC PROGENITOR CELLS AFTER FREEZE-THAWING

| Sample | Pre-/Post-Freeze-Storage | No. Viable Cells × 10$^{-6}$ | Total Number of Hematopoietic Progenitor Cells per 4 × 10$^6$ Frozen Cells | | | | |
|---|---|---|---|---|---|---|---|
| | | | CFU-GM Day 7 | CFU-GM Day 14 | BFU-E-2 | BFU-E-1 | CFU-GEMM |
| CB-1 | Pre | 3.7 | 1332 | 5254 | 3848 | 2146 | 3108 |
| | Post | 2.5 | 284 | 2162 | 1680 | 1652 | 1205 |
| | % Survival after Thaw | 67.6 | 21.3 | 41.1 | 43.7 | 77.0 | 38.8 |
| CB-2 | Pre | 3.8 | 3268 | 6004 | 4028 | 4104 | 4864 |
| | Post | 1.4 | 1902 | 2688 | 2361 | 1911 | 990 |
| | % Survival after Thaw | 36.8 | 58.2 | 44.7 | 58.6 | 46.6 | 20.4 |
| CB-3 | Pre | 3.8 | 912 | 4408 | 2964 | 2356 | 2660 |
| | Post | 1.6 | 746 | 2782 | 1702 | 1826 | 742 |
| | % Survival after Thaw | 42.1 | 81.8 | 63.1 | 57.4 | 77.5 | 27.9 |
| CB-10 | Pre | 3.9 | 1014 | 7800 | 3354 | 3120 | 2964 |
| | Post | 1.2 | 1300 | 3175 | 1526 | 829 | 794 |
| | % Survival after Thaw | 30.8 | 128.2 | 40.7 | 45.4 | 26.6 | 26.8 |
| CB-14 | Pre | 3.8 | 1900 | 3724 | 4484 | 3952 | 3344 |
| | Post | 1.1 | 1034 | 2672 | 1194 | 1240 | 892 |
| | % Survival after Thaw | 28.9 | 54.4 | 71.8 | 26.6 | 31.4 | 26.7 |
| CB-15 | Pre | 3.6 | 720 | 2160 | 3096 | 2448 | 1512 |
| | Post | 1.7 | 426 | 2424 | 1170 | 1062 | 740 |
| | % Survival after Thaw | 47.2 | 59.2 | 112.2 | 37.8 | 43.4 | 48.9 |
| CB-16 | Pre | 3.7 | 518 | 1110 | 592 | 1036 | 740 |
| | Post | 0.8 | 112 | 548 | 190 | 280 | 143 |
| | % Survival after Thaw | 21.6 | 21.6 | 49.4 | 67.9 | 27.0 | 19.3 |
| CP-17 | Pre | 3.7 | 0 | 0 | 592 | 1332 | 592 |
| | Post | 0.5 | 190 | 550 | 170 | 360 | 210 |
| | % Survival after Thaw | 13.5 | 100 | 100 | 28.7 | 27.0 | 35.5 |
| Average % Survival after Thaw: | | 36.1 | 65.6 | 65.4 | 45.8 | 44.6 | 30.5 |
| Range ( ) | | (13.5–67.6) | (21.3–128.2) | (40.7–112.2) | (28.7–67.9) | (26.6–77.5) | (19.3–48.9) |

7. Place the tubes in a tray also containing $H_2O$, in an incubator with an atmosphere of 5% $CO_2$, and a temperature of 37° C., for 20 minutes.
8. Add 0.5 ml (2.5 mg) of ice cold (4° C.) Scolds (nonradioactive) thymidine (Sigma #T-9250) at 5 mg/ml to each tube, and vortex lightly. Add an additional 2 ml of ice cold McCoy's 5A medium to each tube.
9. Pellet cells by centrifugation at 200–400×g at 4° C. for 10 minutes.
10. Aspirate the supernatant into an appropriate container (one used for radioactive disposal), and resuspend the cells with 2 ml cold medium. Repeat step #10.
11. Aspirate the supernatant into an appropriate container. Resuspend with McCoy's 5A containing 10% FCS to a volume where the cell concentration is at least 10 fold greater than the plating concentration.
12. Keep cells on ice until ready to plate.
13. Plate and carry out colony forming assays as described supra in sections 6.6.1 through 6.6.3.

As shown in Table V, the average % survival after freeze-thawing was 36.1, 65.6, 65.4, 45.8, 44.6, and 30.5, respectively, for nucleated cells, day 7 CFU-GM, day 14 CFU-GM, BFU-E-2, BFU-E-1, and CFU-GEMM. There was a range of variability in recovery rates.

It should be noted that the data presented in Table V reflects cell losses incurred during Ficoll-Hypaque separations and procedures for DMSO removal, two steps which are omitted in a preferred embodiment of the invention (NB: DMSO should be removed before colony assays if such are desired to be carried out).

6.8. Calculations of the Reconstituting Potential of Cord Blood

The following discussion demonstrates that individual collections of cord blood (such as described in Section 6.1) contains sufficient hematopoietic stem and progenitor cells to repopulate the hematopoietic system of an individual.

A survey of published reports indicates that the number of CFU-GM infused for autologous bone marrow reconstitution in human patients, can be relied on as an indicator of the potential for successful hematopoietic reconstitution (Spitzer, G., et al., 1980, Blood 55(2): 317–323; Douay et al., 1986, Exp. Hematol. 14:358–365). By standardizing published data by patient weight, and assuming a patient weight of 150 pounds (67.5 kilograms), the calculated number of CFU-GM needed for successful hematopoietic reconstitution using autologous bone marrow cells ranges from $2-425 \times 10^4$, with faster recovery noted using greater than $10 \times 10^4$ CFU-GM.

The data presented in Table III, supra, for 81 cord blood collections, analyzed for day 14 CFU-GM count, shows a range of $0-109 \times 10^4$ CFU-GM per Ficoll-Hypaque-separated individual blood collections. Seventy samples contained greater than or equal to $2 \times 10^4$ CFU-GM, while thirty samples contained greater than or equal to $10 \times 10^4$ CFU-GM. It should be emphasized that this data is derived from Ficoll-Hypaque-separated cells obtained by either gravity drainage from the cord or needle aspiration from the delivered placenta. In a preferred embodiment of the invention, where whole blood is both frozen and infused for therapeutic use, losses due to Ficoll-Hypaque separation can be avoided (see Table IV and Section 6.3.1 infra for data on cell losses incurred during Ficoll-Hypaque separations). In addition, as mentioned in Section 6.1, supra, in recent blood collections, we have been able to obtain volumes approximately twice as large as shown in FIG. 2 or described in Table III, by using needle aspirations from the delivered placenta at the root of the placenta and in the distended surface veins, in combination with cord drainage. Furthermore, an adjustment of the collection protocol to provide for immediate cord clamping upon delivery should result in receipt of greater blood collection volumes (See Yao, A. C., et al., Oct. 25, 1969, Lancet:871–873, wherein collected neonatal blood, obtained by drainage from the umbilical cord and from the delivered placenta, averaged 126.6 ml volume when the umbilical cord was clamped in less than 5 seconds after birth). Thus, although an analysis of the data of Table III should be adjusted for expected losses during freeze-thawing (which losses, however, should not exceed 35%), there should be sufficient cord stem and progenitor cells per collection sample to successfully effect hematopoietic reconstitution.

Furthermore, the reconstituting capacity of cord blood hematopoietic cells may be higher than that of an equal number of bone marrow cells. Colonies derived from cord blood cells are usually larger in size than those derived from adult bone marrow. 6.9. In Vitro Culture Conditions for Hematopoietic Stem and Progenitor Cells Culture conditions for the growth in vitro of hematopoietic progenitor cells from human cord blood have been described in Smith, S. and Broxmeyer, H. E., 1986, British Journal of Hematology, Vol. 63, pp. 29–34, which is incorporated by reference herein in its entirety. Culture media was composed of the following ingredients:

RPMI 1640 media (Gibco Laboratories, Grand Island, N.Y.)

$10^{-6}$ M hydrocortisone (Sigma, St. Louis, Mo.)

5 ug/ml Vitamin $D_3$ (U.S. Biochemical Corp., Cleveland, Ohio)

20% fetal calf serum, heat-inactivated (Hyclone Laboratories, Logan, Utah)

2 gm/l $NaHCO_3$ (Fisher Scientific Co., Fair Lawn, N.J.)

100 U/ml Penicillin 100 ug/ml Streptomycin 0.25 ug/ml Fungizone

Various conditions and factors can be tested for any effect increasing the self-renewal ability of stem cells in vitro. These include but are not limited to oxygen tension (see Smith and Broxmeyer, 1986, Br. J. Hematol. 63:29–34, incorporated by reference herein), superoxide dismutase (Sigma Chemical Co., St. Louis, Mo.), glucose oxidase (Sigma Chemical Co.), and combinations of various colony stimulating factors, namely interleukin-3 (IL-3), granulocyte-macrophage (GM)-colony stimulating factor (CSF), granulocyte (G)-CSF, macrophage (M)-CSF (CSF-1), erythropoietin, IL-1, and IL-4 (B cell growth factor).

6.10. Mouse Dissection Protocols

Mouse bone marrow and spleen are valuable sources of murine hematopoietic stem and progenitor cells for model studies testing new and/or improved protocols for use with the human neonatal stem and progenitor cells of the present invention. Procedures for dissection of mouse bone marrow and spleen are described in Sections 6.10.1, and 6.10.2, respectively. 6.10.1. Bone Marrow Dissection The following procedure can be used to obtain a murine bone marrow cell suspension:

1. Sacrifice mouse as prescribed by cervical-thoracic dislocation.
2. Inside a laboratory hood, soak the mouse with 70% ethanol (to avoid microbial contamination), completely wetting the fur.
3. Snip through the skin, and peel the skin down to the hip by holding the foot with either forceps that have been soaked in 70% ethanol, or with fingers, and pulling the skin with forceps.
4. With sterile (alcohol-treated) forceps and scissors, cut away as much muscle tissue as possible to expose the femur.
5. Remove the tibia from the femur by cutting through the knee cartilage/joint. Discard the tibia.
6. Remove the femur from the body by placing the sharp edge of a scissors on the anterior side of the hip joint, and pulling the femur in the opposite direction against the scissors, so that the scissors fits in the fold. Snip through the joint.
7. Remove the knee end of the femur first, by snipping just the end with a scissors. Remove the hip end from the femur by the same method.
8. With a 10 cc syringe containing 5 ml media (McCoys 5A 1×) and a 27 gauge needle, place the needle in the bone cavity via the hip end of the bone.
9. Flush the marrow from the bone by forcing media into the cavity with the syringe, while holding the bone and syringe over a 17×100 mm tube.
10. After both femurs have been evacuated, break up clumps with a 10 cc syringe and a 23 gauge needle.
11. Pellet the cells by centrifugation at 400×g (1500 rpm in a Beckman TJ-6R rotor) for 10 minutes at 4° C.
12. Aspirate the supernatant and discard it.
13. Resuspend the cells with 10 ml McCoys 5A media and a pipette, and repeat steps 11 and 12.
14. Resuspend the cells with 10 ml McCoy's 5A media with a pipette, and count the cells (with a hemocytometer).

6.10.2. Spleen Dissection

The following procedure can be used to obtain a murine spleen cell suspension:

1. Sacrifice mouse as prescribed by cervical-thoracic dislocation.
2. Inside a laboratory hood, soak the mouse with 70% ethanol (to avoid microbial contamination), completely wetting the fur.
3. Place the mouse on its abdomen and snip through its left side skin with a sterile scissors and forceps.
4. Lift the peritoneum with the forceps, and snip through to the abdominal cavity.

5. With the spleen in view, remove it and place it in a 60×100 mm dish containing 5–7 ml media.
6. Place the spleen in a sterile homogenizing screen, in the dish, and snip it into small pieces.
7. With the plunger of a 10 cc syringe, gently work the tissue through the screen into a dish containing media.
8. Transfer the cell suspension from the dish to a tube. Rinse the plate with 3 ml media and pool.
9. Resuspend small pieces by transferring the cell suspension from the tube to a 10 cc syringe, and passing it through a 23 gauge needle twice.
10. Pellet the cells by centrifugation at 400×g (1500 rpm) for 10 minutes at 4° C.
11. Aspirate the supernatant and discard it.
12. Resuspend the cells with 10 ml McCoy's 5A media and a pipette, and repeat steps 10 and 11.
13. Resuspend the cells with 10 ml McCoy's 5A media, and count the cells (with a hemocytometer).

6.11. Hematopoietic Reconstitution of Adult Mice with Sygeneic Fetal or Neonatal Stem Cells The experiments described in the examples sections infra demonstrate the hematopoietic reconstitution of adult mice with syngeneic or Tla-congenic stem cells of fetal or neonatal blood.

A key reference and source of citations for use in animal model studies, which describes standards for experimental irradiation, of mice and other mammals, at the level causing 100% mortality from hematopoietic failure, and prevention of such mortality by hematopoietic reconstitution (with bone marrow cells), is: Balner, H. Bone Marrow Transplantation and Other Treatment after Radiation Injury, Martinus Nijhoff Medical Division, The Hague, 1977, which is incorporated by reference herein.

6.11.1. Hematopoietic Reconstitution of Lethally-Irradiated Mice With Stem Cells in Blood of the Near-Term Fetus The examples herein described demonstrate that stem cells in blood of the near-term fetus are able to reconstitute the hematopoietic system of lethally-irradiated mice.

The irradiated mice were ten (B6 X A-Tla$^b$)F$_1$ hybrid males, aged seven weeks. The mice were exposed to 862.8 rads at a radiation dose of 107.85 rad/min for 8 minutes with a $^{137}$Cs source. This dose constitutes the LD100/30 days, i.e., the minimum or near-minimal Lethal Dosage causing 100% mortality within a 30-day post-irradiation period. Use of the 30-day survival endpoint is standard because hematopoietic reconstitution is deemed sufficient by that time, and any later mortality is therefore attributable to causes other than hematopoietic failure.

Blood was collected from five near-term (B6-Tla$^a$ X A)F$_1$ hybrid fetuses, delivered by Caesarian section from one mother. In this experiment, near-term fetuses were used instead of neonates in order to ensure microbial sterility. The genetics of donor and recipient mice provides complete histocompatibility except for a segment of chromosome 17 bearing the Tla marker gene. All mice were maintained previously and throughout on acidified drinking water to eradicate pseudomonas and similar infective organisms.

As a restorative treatment, three mice each received 0.17 ml heparinized whole fetal blood (made up to a total volume of approximately 0.2 ml by adding M199 medium with penicillin and streptomycin added) by intravascular injection into a peri-orbital vein of the eye, within two hours of irradiation. The results (Table VI) demonstrated the resultant survival of mice reconstituted with fetal blood stem cells, in contrast to the observed death of mice which had undergone no restorative treatment.

TABLE VI

HEMATOPOIETIC RECONSTITUTION OF LETHALLY-IRRADIATED ADULT MICE WITH STEM CELLS IN BLOOD OF THE NEAR-TERM FETUS

| Group | Day of Death | 30-day Survival Rate* |
|---|---|---|
| (1) Treated | 14 | 2/3** |
| (2) Controls: no restorative treatment but conditions otherwise identical | 11, 12, 12, 13, 13, 15, 15 | 0/7 |

*All 30-day survivors were normally healthy over prolonged periods of observation, displaying the typical post-irradiation graying of the coat, and would doubtless have experienced an approximately normal life-span, as is typical of reconstitution with syngeneic or near-syngeneic cell donors.
**Later typing for the Tla marker by cytotoxicity assay of thymocytes (Schlesinger, M., et al., 1965, Nature 206:1119–1121; Boyse, E. A., et al., 1964, Methods in Medical Research 10:39) established repopulation by donor cells of the injected blood.

6.11.2. Hematopoietic Reconstitution of Mice with a Lesser Volume of Near-Term Fetal Blood But not With Adult Blood The examples herein described demonstrate that a defined volume of near-term fetal blood contains adequate hematopoietic stem cells to effectively reconstitute the hematopoietic system of lethally-irradiated mice, while the same volume of adult blood will not effect successful reconstitution.

The irradiated mice were 20 (B6 x A-Tla$^b$)F$_1$ hybrid males aged 7 weeks, and 10 (B6 x A-Tla$^b$)F$_1$ females aged 7 weeks. The mice were exposed to 862.8 rads at a radiation dose of 107.85 rad/min for 8 minutes with a $^{137}$Cs source (LD100/30 days).

Blood was collected from eight near-term (B6-Tla$^b$ x A)F$_1$ hybrid fetuses, delivered by Caesarian section from one mother. In this experiment, near-term fetuses were used instead of neonates in order to ensure microbial sterility. The genetics of donor and recipient mice provides complete histocompatibility except for a segment of chromosome 17 bearing the Tla marker gene. All mice were maintained previously and throughout on acidified drinking water to eradicate pseudomonas and similar infective organisms.

As a restorative treatment, 10 mice received 0.02 ml heparinized whole fetal blood per mouse (made up to a total volume of 0.22 ml by adding M199 medium with penicillin and streptomycin added), and 10 mice each received 0.02 ml adult whole blood identically treated, by intravascular injection into a peri-orbital vein of the eye, within 2 hours of irradiation. Control mice received no restorative treatment. The results (Table VII) demonstrated that stem cells in a defined volume of fetal blood can successfully reconstitute the hematopoietic system, while cells in an equal volume of adult blood cannot.

TABLE VII

SUCCESSFUL HEMATOPOIETIC RECONSTITUTION WITH A DEFINED VOLUME OF NEAR-TERM FETAL BLOOD BUT NOT WITH ADULT BLOOD

| Group | Day of Death | 30-day Survival Rate* |
|---|---|---|
| (1) Treated with fetal blood | 10, 12, 12, 14, 14 | 5/10** |
| (2) Treated with adult blood | 11, 11, 12, 12, 12, 13, 14, 14, 15, 15 | 0/10 |

TABLE VII-continued

SUCCESSFUL HEMATOPOIETIC RECONSTITUTION
WITH A DEFINED VOLUME OF NEAR-TERM
FETAL BLOOD BUT NOT WITH ADULT BLOOD

| Group | Day of Death | 30-day Survival Rate* |
|---|---|---|
| (2) Controls: no restorative treatment but conditions otherwise identical | 9, 10, 10, 11, 11, 12, 12, 12, 15, | 0/10 |

*All 30-day survivors were normally healthy over prolonged periods of observation, displaying the typical post-irradiation graying of the coat, and would doubtless have experienced an approximately normal life-span, as is typical of reconstitution with syngeneic or near-syngeneic cell donors.
**Later typing for the Tla marker by cytotoxicity assay of thymocytes (Schlesinger, M., et al., 1965, Nature 206:1119–1121; Boyse, E. A., et al., 1964, Methods in Medical Research 10:39) established repopulation by donor cells of the injected blood.

6.11.3. Hematopoietic Reconstitution With Blood of Newborn Mice in Volumes as Low as Ten Microliters The examples herein described demonstrate that the stem cells in a volume of neonatal blood as low as 10 microliters can reconstitute the hematopoietic system of lethally-irradiated mice.

The irradiated mice were 20 (B6 x A-Tla$^b$)F$_1$ hybrid males aged 8–12 weeks. The mice were exposed to 862.8 rads at a radiation dose of 107.85 rad/min for 8 minutes with a $^{137}$Cs source (LD100/30 days).

Blood was collected by cervical section from eighteen (B6-Tla$^a$ x A)F$_1$ hybrid neonates, less than 24 hours old. As a restorative treatment, 5 mice received 0.04 ml heparinized whole neonatal blood per mouse (made up to a total volume of approximately 0.2 ml by adding M199 medium with penicillin and streptomycin added), (Group 1); 5 mice each received 0.02 ml (Group 2); 5 mice each received 0.01 ml (Group 3); and 5 mice received no further treatment (Group 4, radiation control). Treatment was by intravascular injection into a peri-orbital vein of the eye.

The genetics of donor and recipient mice provides complete histocompatibility except for a segment of chromosome 17 bearing the Tla marker gene. All mice were maintained previously and throughout on acidified drinking water to eradicate pseudomonas and similar infective organisms.

The results in Table VIII show that stem cells in extremely small neonatal blood volumes (down to 10 ul) were able to reconstitute the hematopoietic system.

TABLE VIII

SUCCESSFUL HEMATOPOIETIC RECONSTITUTION
WITH NEONATAL BLOOD VOLUMES
AS LOW AS TEN MICROLITERS

| Group | Day of Death | 30-day Survival Rate* |
|---|---|---|
| (1) Treated with 0.04 ml neonatal blood | 12 | 4/5** |
| (2) Treated with 0.02 ml neonatal blood | 14, 18 | 3/5 |
| (3) Treated with 0.01 ml neonatal blood | 12, 12, 14, 14 | 1/5 |
| (4) Controls: no restorative treatment but conditions otherwise identical | 5, 6, 9, 10, 11 | 0/5 |

TABLE VIII-continued

SUCCESSFUL HEMATOPOIETIC RECONSTITUTION
WITH NEONATAL BLOOD VOLUMES
AS LOW AS TEN MICROLITERS

| Group | Day of Death | 30-day Survival Rate* |
|---|---|---|

*All 30-day survivors were normally healthy over prolonged periods of observation, displaying the typical post-irradiation graying of the coat, and would doubtless have experienced an approximately normal life-span, as is typical of reconstitution with syngeneic or near-syngeneic cell donors.
**Later typing for the Tla marker by cytotoxicity assay of thymocytes (Schlesinger, M., et al., 1965, Nature 206:1119–1121; Boyse, E. A., et al., 1964, Methods in Medical Research 10:39) established repopulation by donor cells of the injected blood.

6.11.4. Hematopoietic Reconstitution With Blood of Newborn Mice in Volumes of 10 or 15 Microliters The examples herein described demonstrate that the stem cells in a volume of neonatal blood as low as 10 or 15 microliters can reconstitute the hematopoietic system of lethally-irradiated mice.

The irradiated mice were 15 male and 5 female (B6 x A-Tla$^b$)F$_1$ hybrids aged 10–12 weeks. The mice were exposed to 862.8 rads at a radiation dose of 107.85 rad/min for 8 minutes with a $^{137}$Cs source (LD100/30 days).

Blood was collected by cervical section from fourteen (B6 x A-Tla$^b$)F$_1$ hybrid neonates, less than 24 hours old. As a restorative treatment, 10 mice received 0.015 ml heparinized whole neonatal blood per mouse (made up to a total volume of approximately 0.2 ml by adding M199 medium with penicillin and streptomycin added), (Group 1); 5 mice each received 0.01 ml (Group 2); and the 5 female mice received no further treatment (Group 3, radiation control). Treatment was by intravascular injection into a peri-orbital vein of the eye. The donor and recipient mice were genetically identical, and thus completely histocompatible. All mice were maintained previously and throughout on acidified drinking water to eradicate pseudomonas and similar infective organisms.

The results shown in Table IX reveal that stem and progenitor cells in neonatal blood volumes of 10 or 15 microliters were able to reconstitute the hematopoietic system.

TABLE IX

SUCCESSFUL HEMATOPOIETIC RECONSTITUTION
WITH NEONATAL BLOOD VOLUMES
OF 10 OR 15 MICROLITERS

| Group | Day of Death | 30-day Survival Rate* |
|---|---|---|
| (1) Treated with 0.15 ml neonatal blood | 12, 12, 12 13, 13, 13 | 4/10 |
| (2) Treated with 0.01 ml neonatal blood | 12, 16 | 3/5 |
| (4) Controls: no restorative treatment but conditions otherwise identical | 12, 13, 14, 17, 22 | 0/5 |

*All 30-day survivors were normally healthy over prolonged periods of observation, displaying the typical post-irradiation graying of the coat, and would doubtless have experienced an approximately normal life-span, as is typical of reconstitution with syngeneic or near-syngeneic cell donors.

6.12. Hematopoetic Reconstitution for Treatment of Fanconi's Anemia

In the example herein, we describe a procedure which was carried out to effect the hematopoietic reconstitution of a patient by allogeneic peripheral blood stem cell infusion, for treatment of the genetic anemia Fanconi's syndrome.

The patient was a 5 year old white male child with Fanconi's anemia. The patient was first noted to be pancytopenic at 24 months of age. He was subsequently confirmed to have Fanconi's anemia by diepoxybutane-induced chromosomal breakage assay (Auerbach, A. D., et al., 1979, Am. J. Hum. Genet. 31(1):77–81). The patient had undergone no interventional therapy other than Danazol administration. He had undergone transfusions on two occasions (once with red cells and once with platelets).

The source of neonatal blood for the hematopoietic reconstitution was a female sibling, who was compatible with the patient for HLA and red cell antigens. By study of the in utero sibling's fibroblasts obtained at amniocentesis, the sibling was found to be a four antigen match. The chromosome breakage test (Auerback, A. D., et al, 1979, Am. J. Hum. Genet. 31(1):77–81) demonstrated that the female sibling did not suffer from Fanconi's anemia.

Approximately 150 ml neonatal blood was collected from the umbilical cord and placenta of the sibling at birth, and was diluted 1:1 in sterile pyrogen-free saline containing DMSO to a final concentration of 10% DMSO. The blood was then shipped under sterile conditions by overnight mail to a processing site, where it was frozen slowly, in transplantation bags, in a time-freezing apparatus, and was stored in liquid nitrogen.

Prior to freezing, a sample of the diluted blood was assayed to determine hematopoietic progenitor cell counts as described in Section 6.6, supra. The results are shown in Table X.

TABLE X

HEMATOPOIETIC PROGENITOR CELLS IN DONOR NEONATAL BLOOD

| Before Freezing | Cord Blood | Placental Blood | Total |
|---|---|---|---|
| Total Nucleated Cells | $1.05 \times 10^9$ | $1.42 \times 10^8$ | $1.2 \times 10^9$ |
| Granulocyte-Macrophage Progenitors (CFU-GM) | $2.23 \times 10^5$ | $0.13 \times 10^5$ | $2.46 \times 10^5$ |
| Erythroid Progenitors (BFU-E) | $3.72 \times 10^5$ | $0.25 \times 10^5$ | $3.97 \times 10^5$ |
| Multipotential Progenitors (CFU-GEMM) | $3.57 \times 10^4$ | $0.28 \times 10^4$ | $0.39 \times 10^4$ |

After a test freeze-thaw on a sample of the neonatal blood (1 month frozen), recovery of viable hematopoietic progenitor cells was as follows (as assessed by in vitro hematopoietic progenitor cell colony assays as described in Section 6.6): 100% of CFU-GM, 45% of BFU-E, and 75% of CFU-GEMM.

The patient was conditioned for hematopoietic reconstitution by methods similar to those which have been used for conditioning nonconstitutional aplastic anemia (Gluckman, E., et al., 1984, in Aplastic Anaemia, Stem Cell Biology and Advances in Treatment, Young, N. S., et al., eds., Alan R. Liss, Inc., New York, pp. 325–333; incorporated by reference herein) except that dosages of chemoradiotherapy were decreased. The patient was administered cytoxin® (cyclophosphamide) intravenously at a dosage of 5 mg/kg/day at six, five, four, and three days prior to neonatal blood infusion, for a total of 20 mg/kg. One day prior to infusion, the patient was subjected to thoraco-abdominal irradiation with 500 rads and administered Cyclosporin A.

The frozen blood sample was shipped, under liquid nitrogen, to the site of patient treatment, where it was thawed in a water bath. Approximately 300 ml of the thawed blood sample was infused intravenously into the patient for treatment of the Fanconi's anemia.

6.13. Flowchart: Description of a Service

In a particular embodiment of the invention, the isolation and preservation of neonatal hematopoietic stem and progenitor cells is envisioned as a service offered to each prospective cell donor, which can comprise the steps listed below. The description is meant for illustrative purposes only, in no way limiting the scope of the invention.

1. Contact

Initial contact is made between an expectant mother (client) and the obstetrician, who arranges the service.

2. Blood Collection

In the obstetrical ward, after the infant has been delivered and separated from the cord in the usual way, blood is drawn from the cord into a specially designed receptacle, which is sealed and placed in a customized shipping container, together with a data-form, completed by a member of the obstetrical team, giving details of the birth.

3. Transport

Once daily, an overnight freight carrier collects the shipping containers from the obstetrical wards, and transports them to processing headquarters by 10:30 A.M. the following day.

4. Registration

Upon receipt at headquarters, each container is catalogued. The blood enters the laboratory for processing (optional).

5. Blood Processing (optional)

The cells are separated, and the white cells, which include the stem and progenitor cells, are retained for storage.

6. Testing

The separated cells undergo routine testing (see Section 5.1.2, supra). In exceptional cases, special testing may be indicated to determine whether the sample is contaminated, e.g., by maternal blood. Samples may be rejected for reason of contamination or other causes.

7. Packaging and Labeling

Cells from each accepted sample are dispensed into standard freezing vials (cryules) and labeled in conventional and computer-generated characters.

The cells of each individual are allocated to four cryules, two of which are assigned for storage to one freezer and two to another, independently-serviced, freezer. A fifth cryule contains cells set aside for testing of identity, viability, and function, when withdrawal of cells is required for therapy.

Labels are printed by computer, using a special printer, on silk, which withstands immersion in liquid nitrogen. The label data include the registration number, in machine readable and human readable characters, date of freezing, cryule number (1–4, 5) and freezer assignment (A and B).

8. Freezing and Storage

The cryules are subjected to slow freezing, and assigned to two separately maintained liquid nitrogen refrigerators.

9. Permanent Records

The entire preparative history is entered into the permanent records, including location within cryostorage modules.

For example, data input for each donor for maintenance in the computer records can comprise:

Registration number
Name
Sex
Date of birth
Place of birth (hospital identification)
Birth certificate number
Name of mother
Date of receipt of cells
Date of freezing
Freezer positions
Obstetrical data
  (a) special circumstances of birth
  (b) if twin, registration number of co-twin
  (c) any health disorder of the mother
Test results
  (a) differential cell counts
  (b) bacterial cultures
  (c) other tests performed 10. Notification to Client The client is notified of the registration number, for preservation with child's documents, and is asked for information not available at the time of birth (given name, birth number), for inclusion in permanent records.

11. Withdrawal of Cells for Clinical Use

Requests for cells for treatment of the donor are made on behalf of the donor by a suitably accredited physician affiliated with an appropriate hospital unit. Cells are withdrawn from the cell bank and matched for identity with the recipient. The cells are also tested for viability and microbial contamination, and quantified in terms of stem cell, progenitor cell, and other categories. Further tests are conducted as required. Cells and an accompanying report are delivered to the medical institution designated by the physician. An appropriate notation is entered in the permanent records.

It is apparent that many modifications and variations of this invention as hereinabove set forth may be made without departing from the spirit and scope thereof. The specific embodiments described are given by way of example only and the invention is limited only by the terms of the appended claims.

What is claimed is:

1. A method for treating a human patient in need of hematopoietic reconstitution comprising introducing into the human patient a composition comprising a cryoprotective agent and human neonatal or fetal hematopoietic stem cells derived from the umbilical cord blood or placental blood of a human collected at birth of said human so as to provide hematopoietic reconstitution.

2. The method according to claim 1 in which the composition further comprises human neonatal or fetal hematopoietic progenitor cells derived from the blood.

3. The method according to claim 1 in which the composition comprises whole neonatal or fetal blood.

4. The method according to claim 1 in which the patient has a failure or dysfunction of normal blood cell production and maturation.

5. The method according to claim 4 in which the patient has anemia.

6. The method according to claim 1 in which the patient has a hematopoietic malignancy.

7. The method according to claim 6 in which the hematopoietic malignancy is a leukemia.

8. The method according to claim 6 in which the hematopoietic malignancy is a lymphoma.

9. The method according to claim 1 in which the patient has an autoimmune disease.

10. The method according to claim 1 in which the patient has a genetic disorder.

11. The method according to claim 1 in which the patient is immunodeficient.

12. The method according to claim 11 in which the immunodeficiency is by reason of irradiation.

13. The method according to claim 11 in which the immunodeficiency is by reason of chemotherapy.

14. The method according to claim 11 in which the immunodeficiency is by reason of infection by a pathogenic microorganism.

15. The method according to claim 11 in which the patient has a malignant solid tumor.

16. The method according to claim 1 in which the patient has Fanconi's anemia.

17. The method according to claim 1 in which the patient has a hypoproliferative stem cell disorder.

18. The method according to claim 1 in which the patient is infected by a pathogen.

19. A method for treating a human patient in need of hematopoietic reconstitution comprising:
  (a) obtaining human neonatal or fetal blood components comprising hematopoietic stem cells derived from the umbilical cord blood or placental blood of a human collected at birth of said human;
  (b) cryopreserving the blood components;
  (c) thawing the blood components; and
  (d) introducing the blood components into the human patient so as to provide hematopoietic reconstitution.

20. The method according to claim 19 in which the stem cells are autologous to the patient.

21. The method according to claim 19 in which the stem cells are syngeneic to the patient.

22. The method according to claim 19 in which the stem cells are allogeneic to the patient.

23. The method according to claim 19 in which the blood components comprise whole blood.

24. The method according to claim 19 in which the blood components are isolated by collection from an umbilical cord.

25. The method according to claim 19 in which the blood components are isolated by collection from a placenta.

26. The method according to claim 19 in which the patient is immunodeficient.

27. The method according to claim 19 in which the immunodeficiency is by reason of irradiation.

28. The method according to claim 19 in which the immunodeficiency is by reason of chemotherapy.

29. The method according to claim 19 in which the immunodeficiency is by reason of infection by a pathogen.

30. The method according to claim 26 in which the patient has a malignant solid tumor.

31. The method according to claim 19 in which the patient has anemia.

32. The method according to claim 31 in which the patient has Fanconi's anemia.

33. The method according to claim 19 in which the patient has a hypoproliferative stem cell disorder.

34. The method according to claim 19 in which the patient has a hematopoietic malignancy.

35. The method according to claim 34 in which the hematopoietic malignancy is a leukemia.

36. The method according to claim 34 in which the hematopoietic malignancy is a lymphoma.

37. The method according to claim 19 in which the patient has an autoimmune disease.

38. The method according to claim 19 in which the patient has a hemolytic disorder.

39. The method according to claim 19 in which the patient has a genetic disorder.

40. A method for treating a human patient in need of hematopoietic reconstitution comprising:

(a) obtaining human neonatal or fetal blood components comprising hematopoietic stem and progenitor cells derived from the umbilical cord blood or placental blood of a human collected at birth of said human;

(b) cryopreserving the blood components;

(c) thawing the blood components; and (d) introducing the blood components into the human patient so as to provide hematopoietic reconstitution.

41. The method according to claim 40 in which the stem and progenitor cells are autologous to the host.

42. The method according to claim 40 in which the stem and progenitor cells are syngeneic to the host.

43. The method according to claim 40 in which the stem and progenitor cells are allogeneic to the host.

44. The method according to claim 40 in which the host has Fanconi's anemia.

45. The method according to claim 40 in which the blood components are isolated by collection from an umbilical cord.

46. A method for treating a human patient in need of hematopoietic reconstitution comprising introducing into the human patient a composition comprising human neonatal or fetal hematopoietic stem cells derived from the umbilical cord blood or placental blood of a human collected at birth of said human, in which the stem cells have been previously cryopreserved, so as to provide hematopoietic reconstitution.

47. The method according to claim 1 in which the stem cells are from the umbilical cord blood or placental blood of a single human collected at the birth of said human.

48. A method for treating a human patient in need of hematopoietic reconstitution comprising (a) thawing cryopreserved blood components comprising human neonatal or fetal hematopoietic stem cells derived from the umbilical cord blood or placental blood of a human collected at birth of said human; (b) and introducing the thawed blood components into the human patient so as to provide hematopoietic reconstitution.

49. A method for storing human neonatal or fetal hematopoietic stem cells derived from the blood, said method comprising cryopreserving human neonatal or fetal blood components containing human neonatal or fetal hematopoietic stem cells from the umbilical cord blood or placental blood of a single human collected at the birth of said human, such that the cells remain viable, in which said cells are present in an amount sufficient to effect hematopoietic reconstitution of a human adult.

50. The method of claim 49, wherein said blood components comprise whole blood.

51. The method of claim 49, wherein said cryopreserving comprises adding a cryoprotective agent to said cells.

52. The method of claim 51, wherein said cryoprotective agent is dimethyl sulfoxide.

53. The method of claim 49, 50, 51 or 52, wherein said cryopreserving comprises storing said cells in liquid nitrogen or its vapor.

54. The method of claim 49, 50, 51 or 52, further comprising adding an anticoagulant to said cells.

55. The method of claim 49, 50, 51 or 52, further comprising enriching the cells by a cell separation procedure.

56. The method of claim 49, 50, 51 or 52, further comprising growing the cells *in vitro*.

* * * * *

US006569427C1

(12) EX PARTE REEXAMINATION CERTIFICATE (5828th)

United States Patent
Boyse et al.

(10) Number: US 6,569,427 C1
(45) Certificate Issued: Jul. 24, 2007

(54) ISOLATION AND PRESERVATION OF FETAL AND NEONATAL HEMATOPOIETIC STEM AND PROGENITOR CELLS OF THE BLOOD

(75) Inventors: Edward A. Boyse, Tucson, AZ (US); Hal E. Broxmeyer, Indianapolis, IN (US); Gordon W. Douglas, New York, NY (US)

(73) Assignee: PharmaStem Therapeutics, Inc., Wayne, PA (US)

Reexamination Request:
No. 90/007,458, Mar. 10, 2005
No. 90/007,633, Jul. 18, 2005

Reexamination Certificate for:
Patent No.: 6,569,427
Issued: May 27, 2003
Appl. No.: 08/442,277
Filed: May 16, 1995

Related U.S. Application Data

(63) Continuation of application No. 07/950,356, filed on Sep. 24, 1992, now abandoned, which is a continuation of application No. 07/269,926, filed on Nov. 10, 1988, now Pat. No. 5,192,553, which is a continuation-in-part of application No. 07/119,746, filed on Nov. 12, 1987, now Pat. No. 5,004,681.

(51) Int. Cl.
*A61K 35/14* (2006.01)
*C12N 5/06* (2006.01)

(52) U.S. Cl. .................. 424/93.7; 424/529; 424/530; 424/531; 435/372

(58) Field of Classification Search ............... None
See application file for complete search history.

(56) References Cited

U.S. PATENT DOCUMENTS 5,004,681 A    4/1991  Boyse et al.

OTHER PUBLICATIONS

Declaration of Dr. Axel R. Zander, U.S. Appl. No. 90/007, 091, Apr. 1, 2005, pp. 9–12.
Plaintiff–Appellant PharmaStem Therapeutics, Inc.'s Initial Brief, United States of Appeals for the Federal Circuit, Case No. 05–1490 and 05–1551, Sep. 16, 2005.
Brief for Defendant–Cross Appellant ViaCell, Inc., United States of Appeals for the Federal Circuit, Case No. 05–1490 and 05–1551, Oct. 31, 2005, pp. 46–55.
Plaintiff–Appellant PharmaStem Therapeutics, Inc.'s Reply and Opposition Brief, United States of Appeals for the Federal Circuit, Case No. 05–1490 and 05–1551, Dec. 8, 2005, pp. 20–23.
Reply Brief for Defendants–Cross Appellants, United States of Appeals for the Federal Circuit, Case No. 05–1490 and 05–1551, Jan. 10, 2006, pp. 12–21.
Douay et al., "Recover of CFU–GM from Cryoperserved Marrow and in vivo Evaluation after Autologous Bone Marrow Transplantation are Predictive of Engraftment," Exp. Hematol. 14:358–365 (1986).

Koike, K., "Cryopreservation of Pluripotent and Committed Hemopoietic Progenitor Cells from Human Bone Marrow and Cord Blood," Acta Paediatrica Japonica 25: 275–283 (1983).
Applebaum et al., "Cure of Malignant Lyphoma in Dogs with Peripheral Blood Stem Cell Transplantation," Transplantation 42:19–22 (1986).
Barnes et al., "Hemopoietic Stem Cells in the Peripheral Blood," the Lancet 2:1138–1141 (1967).
Beaujean et al., "Successful Infusion of 40 Cryopreserved Autologous Bone–Marrows. In vitro Studies of the Freezing Procedure," Biomed. Pharmacother. 38: 348–352 (1984).
Deeg et al., "Fanconi's Anemia Treated by Allogeneic Marrow Transplantation," *Blood* 61: 954–959 (1983).
Douay et al., "Recover of CFU–GM from Cryopreserved Marrow and in vivo Evaluation after Autologous Bone Marrow Transplantation are Predictive of Engraftment," Exp. Hemaol. 14:358–365 (1986).
Ende, M. and Ende, N., "Hematopoietic Transplantation by Means of Fetal (Cord) Blood: a New Method," VA Med. Monthly 99: 276–280 (1972).
Kessinger et al., "Reconstitution of Human Hematopoietic Function with Autologous Cryopreesrved Circulating Stem Cells," Exp. Hematol. 14:192–196 (1986).
Knudtzon, S., "In Vitro Growth of Granutocytic Colonies from Circulating Cells in Human Cord Blood," Blood 43: 356–361 (1974).
Koike, K., "Cryopreservation of Pluripotent and Committed Hemopoietic Progenitor Cells from Human Bone Marrow and Cord Blood," Acta Paediatrica Japonica 25: 275–283 (1983).
Maggio–Price et al., "Changes in Hematopoietic Stem Cells in Bone Marrow of Mice with Plasmodium Berghei Malaria," Blood 66:1080–1085 (1985).
Nakahata, T. and Ogawa, M., "Hemopoietic Colony–forming Cells in Umbilical Cord Blood with Extensive Capability to Generate Mono– and Multipotential Hemopoietic Progenitors," J. Clin. Invest. 70:1324–1328 (1982).
Pillow et al., "Treatment of Bone–marrow Failure by Isogeneic Marrow Infusion," N. Engl. J. Med. 275: 94–97 (1966).

(Continued)

*Primary Examiner*—Padmashri Ponnaluri

(57) ABSTRACT

The present application relates to hematopoietic stem and progenitor cells of neonatal or fetal blood that are cyropreserved, and the therapeutic uses of such stem and progenitor cells upon thawing. In particular, the present invention relates to the therapeutic use of fetal or neonatal stem cells for hematopoietic (or immune) reconstitution. Hematopoietic reconstitution with the cells of the invention can be valuable in the treatment or prevention of various diseases and disorders such as anemias, malignancies, autoimmune disorders, and various immune dysfunctions and deficiencies. In another embodiment, fetal or neonatal hematopoietic stem and progenitor cells which contain a heterologous gene sequence can be used for hematopoietic reconstitution in gene therapy. In a preferred embodiment of the invention, neonatal or fetal blood cells that have been cryopreserved and thawed can be used for autologous (self) reconstitution.

OTHER PUBLICATIONS

Prindull et al., "Haematopoietic Stem Cells (CFUc) in Human Cord Blood," *Acta Paediatr. Scand.* 67: 413–416 (1978).

Reiffers et al., "Successful Autologous Transplantation with Peripheral Blood Hemopoietic Cells in a Patient with Acute Leukemia," *Exp. Hematol.* 14: 312–315 (1986).

Santos G.W., "Bone Marrow Transplantation in Leukemia," Cancer 54: 2732–2740 (1984).

Shiraki et al., "Rectification of Immunological Abnormalities and Lupus Nephritis by the Transfer of Bone Marrow cells," Ann. N.Y. Acad. Sci. 420: 309–314 (1983).

Thomas et al., "Aplastic Anaemia Treated by Marrow Transplantation," *Lancet* 1:284–289 (1972).

Wagemaker et al., "Cure of Murine Thalassemia by Bone Marrow Transplantation without Eradication of Endogenous Stem Cells," Transplantation 42: 248–251 (1986).

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentablity of claims 1–56 is confirmed.

\* \* \* \* \*

(12) EX PARTE REEXAMINATION CERTIFICATE (6448th)
United States Patent
Boyse et al.

(10) Number: US 6,569,427 C2
(45) Certificate Issued: Sep. 16, 2008

(54) ISOLATION AND PRESERVATION OF FETAL AND NEONATAL HEMATOPOIETIC STEM AND PROGENITOR CELLS OF THE BLOOD

(75) Inventors: Edward A. Boyse, Tucson, AZ (US); Hal E. Broxmeyer, Indianapolis, IN (US); Gordon W. Douglas, New York, NY (US)

(73) Assignee: Pharmastem Therapeutics, Inc., Wayne, PA (US)

Reexamination Request:
No. 90/008,628, May 31, 2007

Reexamination Certificate for:
Patent No.: 6,569,427
Issued: May 27, 2003
Appl. No.: 08/442,277
Filed: May 16, 1995

Reexamination Certificate B1 6,569,427 issued Jul. 24, 2007

Related U.S. Application Data

(63) Continuation of application No. 07/950,356, filed on Sep. 24, 1992, now abandoned, which is a continuation of application No. 07/269,926, filed on Nov. 10, 1988, now Pat. No. 5,192,553, which is a continuation-in-part of application No. 07/119,746, filed on Nov. 12, 1987, now Pat. No. 5,004,681.

(51) Int. Cl.
*A61K 35/14* (2006.01)
*C12N 5/06* (2006.01)

(52) U.S. Cl. .................. 424/93.7; 424/529; 424/530; 424/531; 435/372

(58) Field of Classification Search .................. None
See application file for complete search history.

(56) References Cited

U.S. PATENT DOCUMENTS

| | | | |
|---|---|---|---|
| 4,306,556 A | * | 12/1981 | Zelman |
| 4,396,601 A | * | 8/1983 | Salser |
| 4,721,096 A | * | 1/1988 | Naughton |
| 5,004,681 A | | 4/1991 | Boyse et al. |

OTHER PUBLICATIONS

Ende et al (VA Med. Monthly 99: 276–280. 1972).*
Kessinger et al (Exp. Hematol. 14: 192–196, 1986).*
Reiffers et al (Exp. Hematol. 14: 312–315, 1986).*
Vidal (Doctoral Dissertation 1985 translated copy).*
Spitzer (Blood, 55: 317–323, 1980).*
Halbrecht (Lancet, 1263–1265, 1939).*
Deeg (Blood. 61:954–959, 1983).*
Beaujean (Biomed.Pjarmacother 38: 348–352, 1984).*
Shiraki (Ann. N.Y. Acad. Sci. 420: 309–314, 1983).*
Maggio–Price (Blood. 68: 1080–1085, 1985).*
Pillow (N. Engl. J. Med. 275: 94–97, 1966).*
Santos (Cancer 52: 2732–2740, 1984).*
Thomas (Lancet 1: 284–289, 1972).*
Wagemaker (Transplantation. 42: 248–251, 1986).*
Stella (J. Clin. Invest. 1987. 80: 286–93) and Morch (Nucleic Acids Res. 1987, 15: 4123–30).*
*Pfizer et al., v. Teva pharmaceuticals USA*. No. 2007–1271) (Fed. Cir.2008)).*
*Pharmastem Therapeutics, Inc.*v. *Viacell, Inc.*, 491 F.3d 1342 (Fed. Cir. 2007).
Barnes et al., "Hemopoietic stem–cells in the peripheral blood," Lancet 1395–6 (1964).
Chervenick et al., "Quantitative studies of blood and bone marrow neutrophils in normal mice," American Journal of Physiology 215:353–60 (1968).
Koike, "Cryopreservation of pluripotent and committed hempoietic progenitor cells from human bone marrow and cord blood," Acta Paediatrica Japonica 25:275–83 (1983).

* cited by examiner

*Primary Examiner*—Padmashri Ponnaluri

(57) ABSTRACT

The present application relates to hematopoietic stem and progenitor cells of neonatal or fetal blood that are cyropreserved, and the therapeutic uses of such stem and progenitor cells upon thawing. In particular, the present invention relates to the therapeutic use of fetal or neonatal stem cells for hematopoietic (or immune) reconstitution. Hematopoietic reconstitution with the cells of the invention can be valuable in the treatment of prevention of various diseases and disorders such as anemias, malignancies, autoimmune disorders, and various immune dysfunctions and deficiencies. In another embodiment, fetal or neonatal hematopoietic stem and progenitor cells which contain a heterologous gene sequence can be used for hematopoietic reconstitution in gene therapy. In a preferred embodiment of the invention, neonatal or fetal blood cells that have been cryopreserved and thawed can be used for autologous (self) reconstitution.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–56 are cancelled.

* * * * *